US012708619B2

(12) United States Patent
Hayden et al.

(10) Patent No.: US 12,708,619 B2
(45) Date of Patent: Aug. 18, 2026

(54) USE OF PRIDOPIDINE FOR TREATING ANXIETY AND DEPRESSION

(71) Applicant: Prilenia Neurotherapeutics Ltd., Yakum (IL)

(72) Inventors: Michael Hayden, Yakum (IL); Michal Geva, Even-Yehuda (IL)

(73) Assignee: Prilenia Neurotherapeutics Ltd., Yakum (IL)

( * ) Notice: Subject to any disclaimer, the term of this patent is extended or adjusted under 35 U.S.C. 154(b) by 803 days.

(21) Appl. No.: 17/967,415

(22) Filed: Oct. 17, 2022

(65) Prior Publication Data

US 2023/0112948 A1 Apr. 13, 2023

Related U.S. Application Data

(63) Continuation-in-part of application No. 16/591,875, filed on Oct. 3, 2019, now Pat. No. 11,471,449, which is a continuation-in-part of application No. 15/052,368, filed on Feb. 24, 2016, now Pat. No. 10,603,311, application No. 17/967,415 is a continuation-in-part of application No. PCT/IL2022/051082, filed on Oct. 11, 2022, which is a continuation-in-part of application No. 17/498,075, filed on Oct. 11, 2021, now abandoned.

(60) Provisional application No. 62/186,221, filed on Jun. 29, 2015, provisional application No. 62/120,771, filed on Feb. 25, 2015.

(51) Int. Cl.

| | |
|---|---|
| ***A61K 31/451*** | (2006.01) |
| ***A61P 25/00*** | (2006.01) |
| ***A61P 25/22*** | (2006.01) |
| ***A61P 25/24*** | (2006.01) |

(52) U.S. Cl.

CPC ............ *A61K 31/451* (2013.01); *A61P 25/00* (2018.01); *A61P 25/22* (2018.01); *A61P 25/24* (2018.01)

(58) Field of Classification Search

CPC .......... A61P 25/00; A61P 25/22; A61P 25/24; A61K 31/451

See application file for complete search history.

(56) References Cited

U.S. PATENT DOCUMENTS

| | | | |
|---|---|---|---|
| 5,321,012 | A | 6/1994 | Mayer et al. |
| 5,462,947 | A | 10/1995 | Svensson et al. |
| 6,114,319 | A | 9/2000 | Kimura et al. |
| 6,903,120 | B2 | 6/2005 | Sonesson et al. |
| 7,417,043 | B2 | 8/2008 | Sonesson et al. |
| 7,579,474 | B2 | 8/2009 | Sonesson et al. |
| 7,923,459 | B2 | 4/2011 | Gauthier et al. |
| 8,680,042 | B2 | 3/2014 | Bogdanova et al. |
| 8,809,302 | B2 | 8/2014 | Cohen et al. |
| 8,835,438 | B2 | 9/2014 | Ishiyama |
| 9,006,445 | B2 | 4/2015 | Sonesson et al. |
| 9,012,476 | B2 | 4/2015 | Zimmermann et al. |
| 9,139,525 | B2 | 9/2015 | Wikstrom |
| 9,163,011 | B2 | 10/2015 | Lueoend et al. |
| RE46,117 | E | 8/2016 | Sonesson et al. |
| 9,718,805 | B2 | 8/2017 | Besidski et al. |
| 9,796,673 | B2 | 10/2017 | Wu et al. |
| 9,814,706 | B2 | 11/2017 | Zimmermann et al. |
| 10,047,049 | B2 | 8/2018 | Barel et al. |
| 10,130,621 | B2 | 11/2018 | Schmidt et al. |
| 10,322,119 | B2 | 6/2019 | Bassan et al. |
| 10,406,145 | B2 | 9/2019 | Schmidt et al. |
| 2007/0238878 | A1 | 10/2007 | Desmond et al. |
| 2010/0048509 | A1 | 2/2010 | Kovacic et al. |
| 2010/0105736 | A1 | 4/2010 | Wikström |
| 2010/0197712 | A1 | 8/2010 | Carlsson et al. |
| 2011/0206782 | A1 | 8/2011 | Zhang |
| 2013/0065966 | A1 | 3/2013 | Navarro Medrano et al. |
| 2013/0150406 | A1 | 6/2013 | Zimmermann et al. |
| 2013/0197031 | A1 | 8/2013 | Sonesson |
| 2013/0267552 | A1 | 10/2013 | Waters et al. |
| 2014/0088140 | A1 | 3/2014 | Hayden et al. |
| 2014/0088144 | A1 | 3/2014 | Egan |
| 2014/0088145 | A1 | 3/2014 | Hayden et al. |
| 2015/0202302 | A1 | 7/2015 | Licht et al. |
| 2015/0209346 | A1 | 7/2015 | Hayden et al. |
| 2015/0216850 | A1 | 8/2015 | Hayden et al. |
| 2015/0374677 | A1 | 12/2015 | Schmidt |
| 2016/0095847 | A1 | 4/2016 | Sonesson |
| 2016/0166559 | A1 | 6/2016 | Sonesson |
| 2017/0020854 | A1 | 1/2017 | Licht et al. |
| 2017/0266170 | A1 | 9/2017 | Waters et al. |
| 2018/0055832 | A1 | 3/2018 | Hayden et al. |
| 2018/0235950 | A1 | 8/2018 | Sonesson |

(Continued)

FOREIGN PATENT DOCUMENTS

| | | |
|---|---|---|
| WO | WO-1999003470 A1 | 1/1999 |
| WO | WO 2001/046144 A1 | 6/2001 |

(Continued)

OTHER PUBLICATIONS

Bermack, Jordanna E.; Debonnel, Guy. The role of sigma receptors in depression. Journal of pharmacological sciences, 2005, 97.3: 317-336.

Pubchem, U.S. National Library of medicine, (Oct. 11, 2011), Database accession No. CID53379489, XP002775774, 2010.

A multiple-ascending dose study of pridopidine in healthy volunteers (2012). Trial Profile Adis Insight Springer (Table of Contents) (http : //adis insight'. springer .com/trials/700207057).

Agosta, F. et al. (2012). Resting state fMRI in Alzheimer's disease: Beyond the default mode network. *Neurobiology of Aging,* 33(8), 1564-1578.

(Continued)

*Primary Examiner* — Sahar Javanmard

(74) *Attorney, Agent, or Firm* — Mark S. Cohen; PEARL COHEN LLP

(57) ABSTRACT

This invention provides a method of treating depression or anxiety in a human subject by administering a composition comprising pridopidine or a pharmaceutically acceptable salt thereof.

12 Claims, 13 Drawing Sheets

(56) References Cited

U.S. PATENT DOCUMENTS

2019/0015401 A1 1/2019 Sonesson
2019/0046516 A1 2/2019 Russ et al.
2019/0192496 A1 6/2019 Hayden et al.
2019/0209542 A1 7/2019 Licht et al.
2019/0350915 A1 11/2019 Bassan et al.
2020/0030308 A1 1/2020 Schmidt et al.
2021/0220342 A1 7/2021 Hayden et al.
2022/0023280 A1 1/2022 Schmidt et al.
2022/0062255 A1 3/2022 Geva et al.

FOREIGN PATENT DOCUMENTS

WO WO-0146145 A1 * 6/2001 .............. A61P 39/02
WO WO-2001046145 A1 6/2001
WO WO 2005/121092 12/2005
WO WO-2006040155 A1 4/2006
WO WO-2008127188 A1 10/2008
WO WO 2008/155357 12/2008
WO WO-2009074607 A1 6/2009
WO WO 2011/054759 A1 5/2011
WO WO-2011107583 A1 9/2011
WO WO-2012002863 A1 1/2012
WO WO-2012028635 A1 3/2012
WO WO 2013/027188 A1 2/2013
WO WO-2013034622 A1 3/2013
WO WO-2013086425 A1 6/2013
WO WO-2013152105 A1 10/2013
WO WO 2014/195322 A1 12/2014
WO WO-2014205229 A1 12/2014
WO WO-2015112601 A1 7/2015
WO WO-2016003919 A1 1/2016
WO WO 2016/138130 A1 9/2016
WO WO-2016138135 A1 9/2016
WO WO-2017015609 A1 1/2017
WO WO-2017015615 A1 1/2017
WO WO-2017048457 A1 3/2017
WO WO-2017147366 A1 8/2017
WO WO-2018039475 A1 3/2018
WO WO-2018039477 A1 3/2018
WO WO 2020/188558 A1 9/2020
WO WO 2022/107146 A1 5/2022

OTHER PUBLICATIONS

Ammar, I. H. et al. (2011). The effects on motor behaviour and short-term memory tasks in mice following an acute administration of Mitragyna speciosa alkaloid extract and mitragynine. *Journal of Medicinal Plants Research,* 5(24), 5810-5817.
Ates-Alagoz, Z. et al. (2013). NMDA receptor antagonists for treatment of depression. *Pharmaceuticals,* 6(4), 480-499.
Austin, M. P. et al. (2001). Cognitive deficits in depression: possible implications for functional neuropathology. *The British Journal of Psychiatry,* 178(3), 200-206.
Balthazar, M. et al. (2014). Alzheimer as a Default Mode Network Disease: A Grey Matter, Functional and Structural Connectivity Study. Alzheimer's & Dementia, 10(4), p. 391.
Barendse, E. M. et al. (2013). Working memory deficits in high-functioning adolescents with autism spectrum disorders: neuropsychological and neuroimaging correlates. *Journal of Neurodevelopmental Disorders,* 5(1), 1-11.
Bartoszyk, G. D. (1998). Anxiolytic effects of dopamine receptor ligands: I. Involvement of dopamine autoreceptors. *Life Sciences,* 62(7), 649-663.
Bartoszyk, G. D. et al.(1997). EMD 68843, a serotonin reuptake inhibitor with selective presynaptic 5-HT1A receptor agonistic properties. *European Journal of Pharmacology,* 322(2-3), 147-153.
Bech, P. (2022). Rating scales in depression: limitations and pitfalls. *Dialogues in Clinical Neuroscience.* 8(2):207-15.
Bech, P et al. (2001). The sensitivity and specificity of the Major Depression Inventory, using the Present State Examination as the index of diagnostic validity. *Journal of Affective Disorders,* 66(2-3), 159-164.
Bonnelle, V. et al. (2012). Salience network integrity predicts default mode network function after traumatic brain injury. *Proceedings of the National Academy of Sciences,* 109(12), 4690-4695.
Bourne, J. N. et al. (2008). Balancing structure and function at hippocampal dendritic spines. *Annual Review of Neuroscience,* 31, 47.
Brier, M. R. et al. (2014). Network dysfunction in Alzheimer's disease: refining the disconnection hypothesis. *Brain Connectivity,* 4(5), 299-311.
Broekkamp, C. L. et al. (1986). Major tranquillizers can be distinguished from minor tranquillizers on the basis of effects on marble burying and swim-induced grooming in mice. *European Journal of Pharmacology,* 126(3), 223-229.
Bryan, K. J. et al. (2009). Chapter 1—Transgenic mouse models of Alzheimer's disease: behavioral testing and considerations. *Methods of Behavior Analysis in Neuroscience.* 2nd edition.
Buckner, R. L. et al. (2008). The brain's default network: anatomy, function, and relevance to disease. *Annals of the New York Academy of Sciences,* 1124(1), 1-38.
Callizot, N. et al. (2013). Operational dissection of β-amyloid cytopathic effects on cultured neurons. *Journal of Neuroscience Research,* 91(5), 706-716.
Carlsson Research (2006) "Carlsson Research Reports Positive Effects of ACR16 in Huntington Disease Phase II Study" Press Release.
Cognition—Definition of Cognition by Oxford Online Dictionary. *Oxford Univ Press* https://www.oed.com/, Accessed Nov. 1989.
Combs, C. K. et al. (2000). Inflammatory mechanisms in Alzheimer's disease: inhibition of β-amyloid-stimulated proinflammatory responses and neurotoxicity by PPARγ agonists. *Journal of Neuroscience,* 20(2), 558-567.
Connor, K. M. et al. (2000). Psychometric properties of the Social Phobia Inventory (SPIN): New self-rating scale. *The British Journal of Psychiatry,* 176(4), 379-386.
Coyle, J. T. et al. (1983). Alzheimer's disease: a disorder of cortical cholinergic innervation. *Science,* 219(4589), 1184-1190.
Cumming, T. B. et al. (2013). Stroke, cognitive deficits, and rehabilitation: still an incomplete picture. *International Journal of Stroke,* 8(1), 38-45.
Cummings, J. L. et al. (1998). Alzheimer's disease: etiologies, pathophysiology, cognitive reserve, and treatment opportunities. *Neurology,* 51(1 Suppl 1), S2-S17.
Dahlen Patrik (2011). NeuroSearch provides update on the Huntexil® development programme and plans a comprehensive restructuring of the company's operations.
Danysz, W. et al. (2003). The NMDA receptor antagonist memantine as a symptomatological and neuroprotective treatment for Alzheimer's disease: preclinical evidence. *International Journal of Geriatric Psychiatry,* 18(S1), S23-S32.
De Tommaso, M. et al. (2004). Effects of rivastigmine on motor and cognitive impairment in Huntington's disease. *Movement Disorders,* 19(12), 1516-1518.
De Yebenes, J. G. et al. (2011). Pridopidine for the treatment of motor function in patients with Huntington's disease (MermaiHD): a phase 3, randomised, double-blind, placebo-controlled trial. *The Lancet Neurology,* 10(12), 1049-1057.
Detrait, E., et al. (2010). Automation of continuous spontaneous alternation to increase the throughput for in vivo screening of cognitive enhancers. Optimization of the ethovision system for the Y-maze test in mice. *Proceedings of Measuring Behavior* (pp. 141-144).
Dietz, D. M. et al. (2014). ΔFosB induction in prefrontal cortex by antipsychotic drugs is associated with negative behavioral outcomes. *Neuropsychopharmacology,* 39(3), 538-544.
Dubinsky, R. et al. (2010). Third Annual Huntington Disease Clinical Research Symposium. *Neurotherapeutics,* 7(1), 135-147.
Dubois, B. et al. (1996). Cognitive deficits in Parkinson's disease. *Journal of Neurology,* 244(1), 2-8.
Dyhring, T. et al. (2010). The dopaminergic stabilizers pridopidine (ACR16) and (−)-OSU6162 display dopamine D2 receptor antagonism and fast receptor dissociation properties. *European Journal of Pharmacology,* 628(1-3), 19-26.

(56) References Cited

OTHER PUBLICATIONS

Extended European Search Report dated Jul. 6, 2018 issued for the corresponding patent application No. 16756274.3.
Extended European Search Report dated Nov. 12, 2019 issued for the corresponding patent application No. 19191835.8.
Extneded European Search Report dated Jun. 24, 2021 issued for the corresponding patent application No. EP21153340.1.
Ferreri, F. et al. (2011). Current research on cognitive aspects of anxiety disorders. *Current Opinion in Psychiatry,* 24(1), 49-54.
Fioravanti, M. et al. (2012). Cognitive deficits in schizophrenia: an updated metanalysis of the scientific evidence. *BMC Psychiatry,* 12(1), 1-20.
Foroud, T. et al. (1995). Cognitive scores in carriers of Huntington's disease gene compared to noncarriers. *Annals of Neurology: Official Journal of the American Neurological Association and the Child Neurology Society,* 37(5), 657-664.
Francardo, V. et al. (2014). Pharmacological stimulation of sigma-1 receptors has neurorestorative effects in experimental parkinsonism. *Brain,* 137(7), 1998-2014.
Geva, M. et al. (2016). Pridopidine activates neuroprotective pathways impaired in Huntington Disease. *Human Molecular Genetics,* 25(18), 3975-3987.
Ghosh, B. C. et al. (2012). Social cognitive deficits and their neural correlates in progressive supranuclear palsy. *Brain,* 135(7), 2089-2102.
Girardi, A. et al. (2011). Deficits in emotional and social cognition in amyotrophic lateral sclerosis. *Neuropsychology,* 25(1), 53.
Gould, T. J. (2010). Addiction and cognition. *Addiction Science & Clinical Practice,* 5(2), 4.
Grachev, I. D. et al. (2021). Sigma-1 and dopamine D2/D3 receptor occupancy of pridopidine in healthy volunteers and patients with Huntington disease: a [18F] fluspidine and [18F] fallypride PET study. *European Journal of Nuclear Medicine and Molecular Imaging,* 48(4), 1103-1115.
Graveland, G. A. et al. (1985). Evidence for degenerative and regenerative changes in neostriatal spiny neurons in Huntington's disease. *Science,* 227(4688), 770-773.
Grunblatt, E. et al. (1999). Potent neuroprotective and antioxidant activity ofapomorphine in MPTP and 6-hydroxydopamine induced neurotoxicity. *Advances in Research on Neurodegeneration,* 57-70.
Guye, M. et al. (2010). Graph theoretical analysis of structural and functional connectivity MRI in normal and pathological brain networks. *Magnetic Resonance Materials in Physics, Biology and Medicine,* 23(5), 409-421.
Hamilton, M. A. X. (1959). The assessment of anxiety states by rating. *British Journal of Medical Psychology.* 32(1):50-55.
Hart, R. P. et al. (2003). Cognitive impairment in patients with chronic pain: the significance of stress. *Current Pain and Headache Reports,* 7(2), 116-126.
Hironaka, N. et al. (2001). Memory-related acetylcholine efflux from rat prefrontal cortex and hippocampus: a microdialysis study. *Brain Research,* 901(1-2), 143-150.
Huang, Y. C. et al. (2011). Increased prothrombin, apolipoprotein A-IV, and haptoglobin in the cerebrospinal fluid of patients with Huntington's disease. *PloS One,* 6(1), e15809.
Huntington Study Group Hart Investigators. (2013). A randomized, double-blind, placebo-controlled trial of pridopidine in Huntington's disease. *Movement Disorders,* 28(10), 1407-1415.
Jacqmin-Gadda, H. et al. (1997). A 5-year longitudinal study of the Mini-Mental State Examination in normal aging. *American Journal of Epidemiology,* 145(6), 498-506.
Johansson, B. et al. (2012). Placebo-controlled cross-over study of the monoaminergic stabiliser (−)-OSU6162 in mental fatigue following stroke or traumatic brain injury. *Acta Neuropsychiatrica,* 24(5), 266-274.
Johnston, T. H. et al. (2019). Pridopidine, a clinic-ready compound, reduces 3, 4-dihydroxyphenylalanine-induced dyskinesia in Parkinsonian macaques. *Movement Disorders,* 34(5), 708-716.
Jonkers, N. et al. (2000). MK801 influences L-DOPA-induced dopamine release in intact and hemi-parkinson rats. *European Journal of Pharmacology,* 407(3), 281-291.
Julian, L. J. (2011). Measures of anxiety. *Arthritis Care & Research,* 63 Suppl. 11(011).
Kalia, L. V. et al. (2008). NMDA receptors in clinical neurology: excitatory times ahead. *The Lancet Neurology,* 7(8), 742-755.
Kalueff, A. V. et al. (2005). Mouse grooming microstructure is a reliable anxiety marker bidirectionally sensitive to GABAergic drugs. *European Journal of Pharmacology,* 508(1-3), 147-153.
Katz, D. M. (2014). Brain-derived neurotrophic factor and Rett syndrome. *Neurotrophic Factors,* 481-495.
Kawahara, M. et al. (2000). Molecular mechanism of neurodegeneration induced by Alzheimer's β-amyloid protein: channel formation and disruption of calcium homeostasis. *Brain Research Bulletin,* 53(4), 389-397.
Keefe, R. S. et al. (2014). Cognitive effects of pharmacotherapy for major depressive disorder: a systematic review. *The Journal of Clinical Psychiatry,* 75(8), 3169.
Kipps, C. M. et al. (2006). Theory of mind in frontotemporal dementia. *Social Neuroscience,* 1(3-4), 235-244.
Krabbendam, L. et al. (2000). Tardive dyskinesia is associated with impaired retrieval from long-term memory: the Curacao Extrapyramidal Syndromes Study: IV. *Schizophrenia Research,* 42(1), 41-46.
Kreitzer, A. C. et al. (2008). Striatal plasticity and basal ganglia circuit function. *Neuron,* 60(4), 543-554.
Lanctot, K. L., et al. (2004). GABAergic function in Alzheimer's disease: evidence for dysfunction and potential as a therapeutic target for the treatment of behavioural and psychological symptoms of dementia. *The Canadian Journal of Psychiatry,* 49(7), 439-453.
Landwehrmeyer, B. et al. (2011). Effects of the dopaminergic stabilizer pridopidine on motor symptoms in Huntington's disease: a meta-analysis. *Clin Genet,* 80(Suppl 1), 14-69.
Leary, M. R. (1983). Social anxiousness: The construct and its measurement. *Journal of Personality Assessment,* 47(1), 66-75.
Lucas-Jimenez, O et al. (2016). Altered functional connectivity in the default mode network is associated with cognitive impairment and brain anatomical changes in Parkinson's disease. *Parkinsonism & Related Disorders,* 33, 58-64.
Luszczki, J. J. et al. (2005). Pharmacological and behavioral characteristics of interactions between vigabatrin and conventional antiepileptic drugs in pentylenetetrazole-induced seizures in mice: an isobolographic analysis. *Neuropsychopharmacology,* 30(5), 958-973.
Marder, K. et al. (2000). Rate of functional decline in Huntington's disease. *Neurology,* 54(2), 452-452.
Mason, S. L et al. (2010). Cognitive follow up of a small cohort of Huntington's disease patients over a 5 year period. *PloS Currents,* 2.
Maurice, T. et al. (1997). SA4503, A novel cognitive enhancer with $\sigma 1$ receptor agonist properties, facilitates NMDA receptor-dependent learning in mice. *European Journal of Pharmacology,* 328(1), 9-18.
Mckhann, G. et al. (1984). Clinical diagnosis of Alzheimer's disease: Report of the NINCDS-ADRDA Work Group under the auspices of Department of Health and Human Services Task Force on Alzheimer's Disease. *Neurology,* 34(7), 939-944.
Mckhann, G. M. et al. (2011). The diagnosis of dementia due to Alzheimer's disease: Recommendations from the National Institute on Aging-Alzheimer's Association workgroups on diagnostic guidelines for Alzheimer's disease. *Alzheimer's & Dementia,* 7(3), 263-269.
Mevel, K. et al. (2011). The default mode network in healthy aging and Alzheimer's disease. *International Journal of Alzheimer's Disease,* 2011.
Michl, M. et al. (2013). Pridopidine in the pharmacological treatment of Huntington's disease. *Clinical Investigation,* 3(7), 691-699.
Millter M. (2006). Swedish Company Announces Results of Phase II study of Dopamine Stabilizing Compound. Huntington's Disease Advocacy Center 2006 http://www.hdac.org/features/article.php?particleNumber=254.

(56) References Cited

OTHER PUBLICATIONS

Mohan, A. et al. (2016). Focus: the aging brain: the significance of the default mode network (DMN) in neurological and neuropsychiatric disorders: a review. *The Yale Journal of Biology and Medicine,* 89(1), 49.
Mostert, J. P. et al. (2008). Therapeutic potential of fluoxetine in neurological disorders. *CNS Neuroscience & Therapeutics,* 14(2), 153-164.
Nasreddine, Z. S. et al. (2005). The Montreal Cognitive Assessment, MoCA: a brief screening tool for mild cognitive impairment. *Journal of the American Geriatrics Society,* 53(4), 695-699.
NeuroSearch (2012). NeuroSearch A/S reports conclusions from the Multiple Ascending Dose study (MAD) with Huntexil®.
NeuroSearch and Fleming Pederson (2010). NeuroSearch announces positive top-line results from Phase III Huntexil® study in Huntington's disease, the MermaiHD study.
Neurosearch and Patrik Dahlen (2011). NeuroSearch provides update on the Huntexil® development programme and plans a comprehensive restructuring of the company's operations.
Nguyen, L. et al. (2015). Role of sigma-1 receptors in neurodegenerative diseases. *Journal of Pharmacological Sciences,* 127(1), 17-29.
Nilsson, M. et al. (2004). The dopaminergic stabiliser ACR16 counteracts the behavioural primitivization induced by the NMDA receptor antagonist MK-801 in mice: implications for cognition. *Progress in Neuro-Psychopharmacology and Biological Psychiatry,* 28(4), 677-685.
Onaolapo, O. J. et al. (2012). Elevated plus maze and Y-Maze behavioral effects of subchronic, oral low dose monosodium glutamate in swiss albino mice. *J. Pharm. Biol. Sci,* 3, 21-27.
Osterberg, O. (2013). A single-center, randomized, placebo-controlled, double-blind study to evaluate the safety, tolerability, and pharmacokinetics of multiple-ascending doses of pridopidine in healthy volunteers. Neurotherapeutics, vol. 10, No. 1, 175-175.
Osterberg, O. et al. (2012) A single center randomized placebo controlled double-blind study to evaluate the safety. Presented at sixth Annual Huntington Disease Clinical Research Symposium, Seattle Washington USA. *Neurotherapeutics,* 9:1-17.
Parada-Turska, J. et al. (1990). Excitatory amino acid antagonists and memory: effect of drugs acting at N-methyl-D-aspartate receptors in learning and memory tasks. *Neuropharmacology,* 29(12), 1111-1116.
Parent, M. B. et al. (2004). Septohippocampal acetylcholine: involved in but not necessary for learning and memory?. *Learning & Memory,* 11(1), 9-20.
Petrella, J. R. et al. (2011). Default mode network connectivity in stable vs progressive mild cognitive impairment. *Neurology,* 76(6), 511-517.
Pettersson, F. et al. (2010). Synthesis and evaluation of a set of 4-phenylpiperidines and 4-phenylpiperazines as D2 receptor ligands and the discovery of the dopaminergic stabilizer 4-[3-(methylsulfonyl) phenyl]-1-propylpiperidine (huntexil, pridopidine, ACR16). *Journal of Medicinal Chemistry,* 53(6), 2510-2520.
Pike, C. J. et al. (1991). In vitro aging of B-amyloid protein causes peptide aggregation and neurotoxicity. *Brain Research,* 563(1-2), 311-314.
Rabinovich-Guilatt, L. et al. (2016). The effect of mild and moderate renal impairment on the pharmacokinetics of pridopidine, a new drug for Huntington's disease. *British Journal of Clinical Pharmacology,* 81(2), 246-255.
Rapaport, M. H. (2009). Future drugs for the treatment of depression: the need to look beyond monoamine systems. *CNS Spectrums,* 14(S5), 14-16.
Reading, P. J. et al. (2001). Rivastigmine in the treatment of parkinsonian psychosis and cognitive impairment: preliminary findings from an open trial. *Movement Disorders: Official Journal of the Movement Disorder Society,* 16(6), 1171-1174.
Remington's Pharmaceutical Sciences, 17th ed. *Journal of Pharmaceutical Sciences.* (1985). 74(10), 1143-1144.
Rosler, M. et al. (1999). Efficacy and safety of rivastigmine in patients with Alzheimer's disease: international randomised controlled trial Commentary: Another piece of the Alzheimer's jigsaw. *Bmj,* 318(7184), 633-640.
Rung, J. P. et al. (2005). The dopaminergic stabilizers (−)-OSU6162 and ACR16 reverse (+)-MK-801-induced social withdrawal in rats. *Progress in Neuro-Psychopharmacology and Biological Psychiatry,* 29(5), 833-839.
Rung, J. P. et al. (2011). Effects of the dopamine stabilizers (S)-(−)-OSU6162 andACR16 on prolactin secretion in drug-naive and monoamine-depleted rats. *Naunyn-Schmiedeberg's Archives of Pharmacology,* 384(1), 39-45.
Sahlholm, K. et al. (2013). The dopamine stabilizers ACR16 and (−)-OSU6162 display nanomolar affinities at the σ-1 receptor. *Molecular Psychiatry,* 18(1), 12-14.
Sahlholm, K. et al. (2015). Pridopidine selectively occupies sigma-1 rather than dopamine D2 receptors at behaviorally active doses. *Psychopharmacology,* 232(18), 3443-3453.
Sakono, M. et al. (2012). Amyloid oligomer detection by immobilized molecular chaperone. Biochemical engineering journal, 61, 28-33.
Sambataro, F. et al. (2010). Age-related alterations in default mode network: impact on working memory performance. *Neurobiology of Aging,* 31(5), 839-852.
Saunders, J. A. et al. (2012). NMDA antagonist MK801 recreates auditory electrophysiology disruption present in autism and other neurodevelopmental disorders. *Behavioural Brain Research,* 234(2), 233-237.
Seibenhener, M. L. et al. (2015). Use of the open field maze to measure locomotor and anxiety-like behavior in mice. JoVE—*Journal of Visualized Experiments,* (96), e52434.
Seo, J. S. et al. (1997). Effect of MK-801 on the Prevention and Treatment of Tardive Dyskinesia. Korean Journal of Biological Psychiatry, 4(2), 246-250.
Sisodia, S. S. et al. (1990). Evidence that β-amyloid protein in Alzheimer's disease is not derived by normal processing. *Science,* 248(4954), 492-495.
Squitieri, F. et al. (2013). One-year safety and tolerability profile of pridopidine in patients with Huntington disease. *Neurology,* 80(12), 1086-1094.
Squitieri, F. et al. (2015). Profile of pridopidine and its potential in the treatment of Huntington disease: the evidence to date. *Drug Design, Development and Therapy,* 9, 5827.
Stafstrom, C. E. et al. (1997). Acute effects of MK801 on kainic acid-induced seizures in neonatal rats. *Epilepsy Research,* 26(2), 335-344.
Steen, R. G. et al. (2005). Cognitive deficits in children with sickle cell disease. *Journal of Child Neurology,* 20(2), 102-107.
Steimer, T. (2011). Animal models of anxiety disorders in rats and mice: some conceptual issues. *Dialogues in Clinical Neuroscience,* 13(4), 495-506.
Stout, J. C. et al. (2014). HD-CAB: A cognitive assessment battery for clinical trials in Huntington's disease1, 2, 3. *Movement Disorders,* 29(10), 1281-1288.
Strik, J. J. et al. (2001). Sensitivity and specificity of observer and self-report questionnaires in major and minor depression following myocardial infarction. *Psychosomatics,* 42(5), 423-428.
Tedroff, J. et al. (1999). Long-lasting improvement following (−)-OSU6162 in a patient with Huntington's disease. *Neurology,* 53(7), 1605-1605.
Treit, D. (1985). Animal models for the study of anti-anxiety agents: a review. *Neuroscience & Biobehavioral Reviews,* 9(2), 203-222.
Treit, D. et al. (1981). Conditioned defensive burying: a new paradigm for the study of anxiolytic agents. *Pharmacology Biochemistry and Behavior,* 15(4), 619-626.
Trung, J. et al. (2019). Transcranial magnetic stimulation improves cognition over time in Parkinson's disease. *Parkinsonism & Related Disorders,* 66, 3-8.
Van Den Buuse, M. et al. (2005). Importance of animal models in schizophrenia research. *Australian & New Zealand Journal of Psychiatry,* 39(7), 550-557.

(56) References Cited

OTHER PUBLICATIONS

Van Rijckevorsel, K. (2006). Cognitive problems related to epilepsy syndromes, especially malignant epilepsies. *Seizure,* 15(4), 227-234.
Winkler, J. et al. (1995). Essential role of neocortical acetylcholine in spatial memory. *Nature,* 375(6531), 484-487.
Yung-Chi, C. et al. (1973). Relationship between the inhibition constant (KI) and the concentration of inhibitor which causes 50 per cent inhibition (150) of an enzymatic reaction. *Biochemical Pharmacology,* 22(23), 3099-3108.
Zhou, J. et al. (2010). Divergent network connectivity changes in behavioural variant frontotemporal dementia and Alzheimer's disease. *Brain,* 133(5), 1352-1367.
Zuccato, C. et al. (2009). Brain-derived neurotrophic factor in neurodegenerative diseases. *Nature Reviews Neurology,* 5(6), 311-322.

* cited by examiner

18F-Fluspidine
S1R occupancy

Statistics: p-values adjusted for search volume

| set-level | | cluster-level | | | | peak-level | | | | | | | |
|---|---|---|---|---|---|---|---|---|---|---|---|---|---|
| p | c | $p_{FWE-corr}$ | $q_{FDR-corr}$ | $k_E$ | $p_{uncorr}$ | $p_{FWE-corr}$ | $q_{FDR-corr}$ | T | $(Z_{\equiv})$ | $p_{uncorr}$ | mm | mm | mm |
| 0.999 | 6 | 0.022 | 0.008 | 89 | 0.001 | 0.441 | 0.268 | 5.19 | 4.26 | 0.000 | −34 | 18 | 12 |
| | | | | | | 0.999 | 0.591 | 3.98 | 3.48 | 0.000 | −31 | 18 | 0 |
| | | 0.291 | 0.060 | 40 | 0.020 | 0.789 | 0.359 | 4.71 | 3.97 | 0.000 | 35 | 21 | −3 |
| | | 0.628 | 0.114 | 25 | 0.057 | 0.987 | 0.591 | 4.19 | 3.63 | 0.000 | 8 | 27 | 42 |
| | | | | | | 1.000 | 0.591 | 3.89 | 3.42 | 0.000 | 5 | 36 | 39 |
| | | 0.824 | 0.150 | 18 | 0.100 | 0.998 | 0.591 | 3.99 | 3.49 | 0.000 | 32 | 54 | 15 |
| | | 1.000 | 0.498 | 3 | 0.498 | 1.000 | 0.695 | 3.72 | 3.30 | 0.000 | 5 | 36 | 6 |
| | | 0.997 | 0.397 | 6 | 0.331 | 1.000 | 0.720 | 3.62 | 3.23 | 0.001 | −10 | 39 | 6 |

table shows 3 local maxima more than 8.0mm apart

Height threshold: T = 3.43, p = 0.001 (1.000) Degrees of freedom = [1.0, 26.0]
Extent threshold: k = 0 voxels FWHM = 12.9 13.0 12.4 mm mm mm; 4.3 4.3 4.1 {voxel:
Expected voxels per cluster, <k> = 6.850 Volume: 2909304 = 107752 voxels = 1277.0 resels
Expected number of clusters, <c> = 17.36 Voxel size: 3.0 3.0 3.0 mm mm mm; (resel = 77.10 v
FWEp: 6.349, FDRp: Inf, FWEc: 89, FDRc: 89

FIGURE 14 (cont.)

Statistics: p-values adjusted for search volume

| set-level | | cluster-level | | | | peak-level | | | | | | | |
|---|---|---|---|---|---|---|---|---|---|---|---|---|---|
| p | c | $p_{FWE-corr}$ | $q_{FDR-corr}$ | $k_E$ | $p_{uncorr}$ | $p_{FWE-corr}$ | $q_{FDR-corr}$ | T | $(Z_\equiv)$ | $p_{uncorr}$ | mm | mm | mm |
| 0.012 | 47 | 0.393 | 0.071 | 25 | 0.015 | 0.803 | 0.929 | 7.72 | 4.31 | 0.000 | -55 | 24 | 21 |
| | | 0.000 | 0.000 | 143 | 0.000 | 0.825 | 0.929 | 7.62 | 4.29 | 0.000 | -49 | -36 | 51 |
| | | | | | | 0.946 | 0.929 | 6.95 | 4.11 | 0.000 | -61 | -30 | 48 |
| | | | | | | 1.000 | 0.929 | 4.97 | 3.45 | 0.000 | -55 | -36 | 42 |
| | | 0.000 | 0.000 | 453 | 0.000 | 0.850 | 0.929 | 7.51 | 4.26 | 0.000 | -61 | -48 | 18 |
| | | | | | | 0.998 | 0.929 | 6.06 | 3.84 | 0.000 | -55 | -57 | 6 |
| | | | | | | 0.998 | 0.929 | 6.02 | 3.83 | 0.000 | -67 | -9 | 0 |
| | | 0.000 | 0.000 | 140 | 0.000 | 0.994 | 0.929 | 6.24 | 3.90 | 0.000 | -37 | 0 | 9 |
| | | | | | | 1.000 | 0.929 | 4.94 | 3.44 | 0.000 | -40 | 12 | 15 |
| | | | | | | 1.000 | 0.929 | 4.88 | 3.41 | 0.000 | -34 | 18 | 6 |
| | | 0.966 | 0.254 | 10 | 0.103 | 1.000 | 0.929 | 5.48 | 3.64 | 0.000 | 14 | -42 | 6 |
| | | 0.007 | 0.002 | 71 | 0.000 | 1.000 | 0.929 | 5.44 | 3.63 | 0.000 | 14 | -54 | 60 |
| | | | | | | 1.000 | 0.929 | 5.29 | 3.57 | 0.000 | 11 | -48 | 42 |
| | | | | | | 1.000 | 0.929 | 5.15 | 3.52 | 0.000 | 11 | -51 | 51 |
| | | 0.725 | 0.142 | 17 | 0.039 | 1.000 | 0.929 | 5.41 | 3.62 | 0.000 | -25 | -48 | 0 |
| | | | | | | 1.000 | 0.975 | 4.41 | 3.21 | 0.001 | -25 | -60 | -3 |
| | | 0.996 | 0.340 | 7 | 0.166 | 1.000 | 0.929 | 5.35 | 3.60 | 0.000 | -43 | 33 | -18 |
| | | 0.966 | 0.254 | 10 | 0.103 | 1.000 | 0.929 | 5.31 | 3.58 | 0.000 | -40 | 45 | 27 |
| | | 0.990 | 0.315 | 8 | 0.141 | 1.000 | 0.929 | 5.28 | 3.57 | 0.000 | 44 | -75 | -9 |
| | | 0.330 | 0.071 | 27 | 0.012 | 1.000 | 0.929 | 5.08 | 3.49 | 0.000 | 53 | 12 | 6 |
| | | 0.981 | 0.282 | 9 | 0.120 | 1.000 | 0.929 | 5.03 | 3.48 | 0.000 | 29 | -81 | 36 |

table shows 3 local maxima more than 8.0mm apart

Height threshold: T = 4.14, p = 0.001 (1.000) Degrees of freedom = [1.0, 10.0]
Extent threshold: k = 0 voxels FWHM = 12.7 12.8 12.1 mm mm mm; 4.2 4.3 4.0 {voxel
Expected voxels per cluster, <k> = 3.875 Volume: 3233250 = 119750 voxels = 1506.3 resels
Expected number of clusters, <c> = 32.97 Voxel size: 3.0 3.0 3.0 mm mm mm; (resel = 72.90 v
FWEp: 10.723, FDRp: Inf, FWEc: 71, FDRc: 4 Page 1

FIGURE 15 (cont.)

USE OF PRIDOPIDINE FOR TREATING ANXIETY AND DEPRESSION

CROSS REFERENCE TO RELATED APPLICATIONS

This application is a Continuation-in-Part application of U.S. patent application Ser. No. 16/591,875, filed Oct. 3, 2019, which is a Continuation-in-Part application of U.S. patent application Ser. No. 15/052,368, filed Feb. 24, 2016, which claims the benefit of U.S. Provisional Application Ser. No. 62/186,221, filed Jun. 29, 2015, and U.S. Provisional Application Ser. No. 62/120,771, filed Feb. 25, 2015. This application is also a Continuation-in-Part application of International Application No. PCT/IL2022/051082, filed Oct. 11, 2022, which is a Continuation-in-Part application of U.S. patent application Ser. No. 17/498,075, filed Oct. 11, 2021, the entire contents of which are hereby incorporated by reference herein.

Throughout this application, various publications are referred to by first author and year of publication. Full citations for these publications are presented in a References section immediately before the claims. Disclosures of the publications cited in the References section are hereby incorporated by reference in their entireties into this application in order to more fully describe the state of the art as of the date of the invention described herein.

BACKGROUND

Pridopidine (4-[3-(methylsulfonyl)phenyl]-1-propyl-piperidine, ACR16, Huntexil) is a drug under development for the treatment of Huntington's Disease and ALS. Pridopidine selectively and robustly binds and activates the Sigma-1 receptor. The SIR is an endoplasmic reticulum (ER) chaperone protein which is implicated in cellular differentiation, neuroplasticity, neuroprotection and cognitive function in the brain. Recently, transcriptomic analysis of rat striatum showed that pridopidine treatment activates expression of the BDNF, dopamine receptor 1 (D1R), glucocorticoid receptor (GR), and the serine-threonine kinase protein kinase B (Akt)/phosphoinositide 3-kinase (PI3K) pathways, known to promote neuronal plasticity and survival. Pridopidine also enhances secretion of the neuroprotective brain-derived neurotrophic factor (BDNF) in a neuroblastoma cell line, in a S IR-dependent manner (Geva 2016).

Processes of synthesis of pridopidine and a pharmaceutically acceptable salt thereof are disclosed in U.S. Pat. No. 7,923,459. U.S. Pat. No. 6,903,120 claims pridopidine for the treatment of Parkinson's disease, dyskinesias, dystonias, Tourette's disease, iatrogenic and non-iatrogenic psychoses and hallucinoses, mood and anxiety disorders, sleep disorder, autism spectrum disorder, ADHD, Huntington's disease, age-related cognitive impairment, and disorders related to alcohol abuse and narcotic substance abuse.

Alzheimer's disease Alzheimer's disease (AD) is the most common form of dementia, a general term for memory loss and other intellectual abilities serious enough to interfere with daily life. AD accounts for 60 to 80 percent of dementia cases (www.alz.org).

AD is characterized by the loss of synapses and neurons from the brain, and by the accumulation of extracellular protein-containing deposits (referred to as 'senile plaques') and neurofibrillary tangles (Selkoe et al. 2001) The most common early symptom of AD is difficulty remembering newly learned information. As AD advances it leads to increasingly severe symptoms, including disorientation, mood and behavior changes, as well as difficulty speaking, swallowing and walking.

Currently, there is no cure for AD. New effective therapies for AD are needed.

Anxiety

Anxiety disorders are a prevalent and disabling psychiatric condition affecting approximately one in four adults. Patients with anxiety experience substantial physical and emotional discomfort, and demonstrate increased illnesses and substance use. The high prevalence of anxiety disorders and the high functional disability they cause lead to a high economic and social cost. Additionally, currently available treatments often result in poor treatment outcome. Therefore, there is a need for more efficient therapies.

Depression

Depression is a common mood disorder that affects about 10% of the population, and is the leading cause of disability worldwide, creating a substantial social and economic burden. Depression affects thoughts, mood and physical health. It is characterized by low mood, lack of energy, sadness, insomnia, and an inability to enjoy life. Depression is diagnosed based on symptoms, and thus treatment of symptomatic and does not address the underlying biological cause. Thus, despite the availability of different treatments, a high proportion of patients with depression remain non-responsive to treatment. Therefore, novel treatments for depression are an unmet, global need.

DMN (Default Mode Network)

The default mode network (DMN), is a large-scale brain network of interacting brain regions known to have activity highly correlated with each other and distinct from other networks in the brain. The DMN includes brain regions with high degrees of functional connectivity and is active in the brain at rest but becomes deactivated when task performance is initiated. The clinical implications of the DMN in neurological and neuropsychiatric disorders have been, and continue to be, targets of investigation. In disorders including AD, PD, TLE, ADHD, and mood disorders, the DMN has been implicated in neurobiological/neurocognitive pathophysiological models. (Mohan et al., The Significance of the Default Mode Network (DMN) in Neurological and Neuropsychiatric Disorders: A Review. Yale J Biol Med. 2016 Mar. 24; 89(1):49-57. PMID: 27505016; PMCID: PMC4797836.).

DMN (Default Mode Network) plays crucial role in cognitive processing, and dysfunction in the DMN is associated with aberrant behaviors and cognition in various NDDs (F. Sambataro et al, 2010; F. Agosta et al, 2012; Bonnelle V et al, 2012). The DMN is comprised of brain regions known to be involved in cognitive functions: posterior cingulate cortex (PCC), lateral parietal cortex and medial prefrontal cortex (mPFC), and prominent connections to nodes in the medial temporal lobe (MTL) and angular gyrus (Desgranges, B. et al, 2011; Buckner R. L. et al, 2008). Specifically, aberrant DMN connectivity seems to be the most affected network in Dementia due to AD (Balthazar et al, AAN 2014). In AD, the DMN consistently shows reduced connectivity, and has even been shown to predict disease severity and progression (Petrella J R, et al, 2011; Brier M R. et al, 2014).

Impaired DMN connectivity is also described in patients with FTD (Zhou J, et al, 2010; Kipps C M. and Hodges J R., 2006), ALS (Girardi A, et al, 2011), PSP (Ghosh B C, et al, 2012), PD (Lucas-Jimenez et al, 2016), as well as in several neuropsychiatric diseases (Buckner R L et al, 2008).

Functional connectivity is decreased in the DMN in patients with major depressive disorder (MDD) compared to healthy controls. Meta-analysis of 32 studies shows decreased functional connectivity between the mPFC and posterior DMN. Additionally, functional connectivity in the DMN was found to be positively related to symptom severity.

Similarly, anxiety symptoms have also been linked to alterations in the DMN. For example, in social anxiety disorder, reduced functional connectivity is observed between the amygdala and mPFC and PCC.

Additional number of studies identified DMN disturbances in schizophrenia, autism, hyperactivity disorder, epilepsy and multiple sclerosis (M. Guye et al, 2010).

SUMMARY OF THE INVENTION

In some embodiments, this invention provides a method of treating depression or anxiety in a human subject by administering a composition comprising an amount of pridopidine, its analog or a pharmaceutically acceptable salt thereof.

In another embodiment, this invention provides a method of treating depression or anxiety in a human subject by administering a composition comprising an amount of pridopidine, its analog or a pharmaceutically acceptable salt thereof wherein the depression or anxiety is not caused by Huntington's disease.

In another embodiment, this invention provides a method of treating depression or anxiety in a human subject by administering a composition comprising an amount of pridopidine, its analog or a pharmaceutically acceptable salt thereof wherein the depression or anxiety is associated with cognitive deficits.

DETAILED DESCRIPTION OF THE INVENTION

Figure 1A:
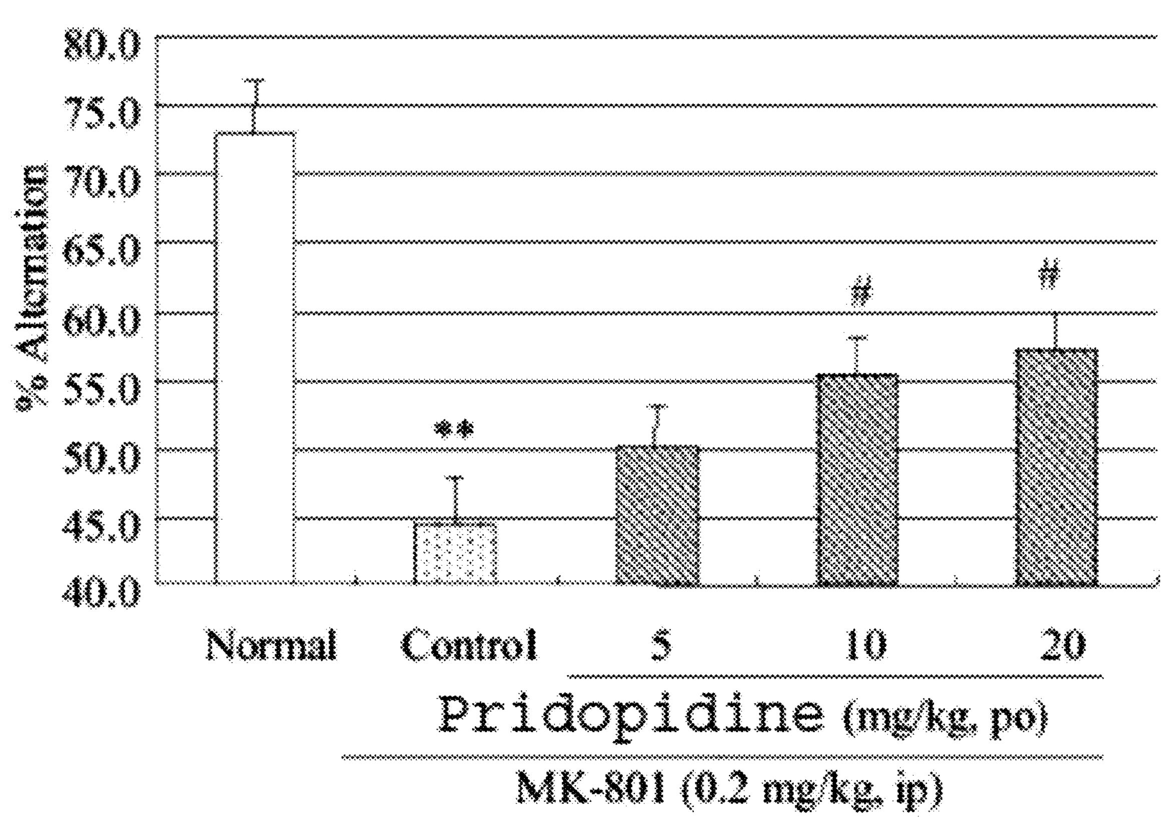
FIGS. 1A and 1B: Effect of pridopidine on the Disruption of Spontaneous Alternation (FIG. 1A) and the Increase in the Number of Total Arm Entries (FIG. 1B) Induced by MK-801 in a Y-maze. Data represents the mean±SEM. **$p<0.01$; statistically significant compared with the normal group (Student's t test). #$p<0.05$; statistically significant compared with the control group (Dunnett's multiple comparison test). Twelve mice were used in each group.

This invention provides a method of improving cognitive function in a subject comprising periodically administering to the subject an amount of pridopidine and/or its analog, or a pharmaceutically acceptable salt thereof effective to improve a cognitive function in the subject. This invention provides a method of improving cognitive function in a human subject comprising administering to the subject an amount of pridopidine and/or its analog, or a pharmaceutically acceptable salt thereof wherein the cognitive function in need for improvement is associated with DMN dysfunction.

In an embodiment, the cognitive function is selected from the group consisting of global cognitive functioning, sustained cognition, memory, language, executive functioning, and attention. In another embodiment, the cognitive function is memory.

In an embodiment, memory is short term memory. In another embodiment, memory is long term memory. In another embodiment, memory is working memory.

In an embodiment, the subject is afflicted with a cognitive deficit. In another embodiment, the subject is prone to or predisposed to have a cognitive deficit.

In an embodiment, the cognitive deficit is a memory deficit.

In an embodiment, the memory deficit is a short-term memory deficit. In another embodiment, the memory deficit is memory loss.

In an embodiment, the memory loss is caused by one or more of age-related changes in memory, mild cognitive impairment, dementia or depression.

In an embodiment, wherein the cognitive deficits comprise memory loss, loss of higher reasoning, forgetfulness, learning disabilities concentration difficulties or decreased intelligence.

In an embodiment, the cognitive deficit is caused by or associated with a disease or disorder.

In an embodiment, the disease or disorder is a disease or disorder associated with NMDA receptor. In another embodiment, the disease or disorder is schizophrenia or autism. In another embodiment, the disease or disorder is epilepsy or an anxiety disorder. In another embodiment, the disease or disorder is amyotrophic lateral sclerosis (ALS). In another embodiment, the disease or disorder is frontotemporal dementia (FTD). In another embodiment, the disease or disorder is mild cognitive impairment (MCI). In another embodiment, the disease or disorder is bipolar disorder. In another embodiment, the disease or disorder is Huntington's disease. In another embodiment, the disease or disorder is selected from the group consisting of major depressive disorder (MDD), Parkinson's disease, Alzheimer's disease, tardive dyskinesia, depression, sickle cell anemia, stroke, chronic pain syndrome, and addiction. In another embodiment, the disease or disorder is selected from the group consisting of mild cognitive impairment, memory loss, memory deficit, a memory deficit related to brain injury or a post-stroke event, a learning deficiency, and behavioral and cognitive problems associated with brain tumors. In another embodiment, the disease or disorder is selected from the group consisting of dementia, dementia associated with Lewy Bodies, age-related cognitive decline, psychosis, attention deficit disorder (ADHD), bipolar disorder, brain injury, mood and affective disorders, Tourette's syndrome, mental retardation, progressive supranuclear palsy, Creutzfeldt-Jacob disease, corticobasal Degeneration, vascular dementia, and Pick's disease. In another embodiment, the disease or disorder is selected from the group consisting of generalized anxiety disorder (GAD), social anxiety disorder (SAD), tardive dyskinesia, depression, sickle cell anemia, chronic pain syndrome, addiction, nicotine addiction, internet addiction, cocaine addiction, tourette's syndrome, mental retardation, corticobasal degeneration, vascular dementia, pick's disease, posttraumatic stress disorder (PTSD), obsessive compulsive disorder, panic disorder (PD), trigeminal pain, trigeminal musculoskeletal pain, phantom limb pain, irritable bowel syndrome, blepharospasm, complex regional pain syndrome, chronic low back pain, autism spectrum disorder (ASD), infantile spasm (IS).

In one embodiment, this invention provides a method of treating a disease or disorder associated with DMN dysfunction comprising administering a pharmaceutical composition comprising pridopidine and/or its analog, or any acceptable salt thereof.

In one embodiment, this invention provides a method of treating depression or anxiety in a subject by administering a composition comprising an amount of pridopidine and/or its analog or a pharmaceutically acceptable salt thereof.

In one embodiment, this invention provides a method of treating depression or anxiety in a subject by administering a composition comprising an amount of pridopidine and/or its analog or a pharmaceutically acceptable salt thereof, wherein the depression or anxiety is not caused by Huntington's disease.

In one embodiment, this invention provides a method of treating depression or anxiety in a subject by administering a composition comprising an amount of pridopidine and/or its analog or a pharmaceutically acceptable salt thereof, wherein the depression or anxiety is not caused by Huntington's disease, and wherein the depression or anxiety is associated with cognitive deficits. In another embodiment, the cognitive deficits comprise memory loss, loss of higher reasoning, forgetfulness, learning disabilities concentration difficulties or decreased intelligence.

In one embodiment, this invention provides a method of treating depression or anxiety in a subject by administering a composition comprising an amount of pridopidine and/or its analog or a pharmaceutically acceptable salt thereof, wherein the anxiety or depression is associated with cognitive deficits. In another embodiment, the cognitive deficits comprise memory loss, loss of higher reasoning, forgetfulness, learning disabilities concentration difficulties or decreased intelligence.

In one embodiment, the method reduces anxiety in the subject. In an embodiment, anxiety is measured by the State-Trait Anxiety Inventory (STAI), the Fear Survey Schedule, Beck Anxiety Inventory (BAI), Brief Fear of Negative Evaluation Scale—BFNE, Clinician Administered PTSD Scale (CAPS), Daily Assessment of Symptoms—Anxiety, Generalized Anxiety Disorder 7 (GAD-7), Hamilton Anxiety Scale (HAM-A), Hospital Anxiety and Depression Scale (HADS-A), Leibowitz Social Anxiety Scale (LSAS), Overall Anxiety Severity and Impairment Scale (OASIS), Panic and Agoraphobia Scale (PAS), Panic Disorder Severity Scale (PDSS), PTSD Symptom Scale—Self-Report Version, Social Phobia Inventory (SPIN), Trauma Screening Questionnaire, Yale-Brown Obsessive Compulsive Scale (Y-BOCS), or the Zung Self-Rating Anxiety Scale.

In one embodiment, anxiety is reduced by at least one unit.

In another embodiment, the method reduces depression in the subject. In an embodiment, depression is measured by Hamilton Rating Scale for Depression (HAM-D), Beck Depression Inventory (BDI), Beck Hopelessness Scale, Centre for Epidemiological Studies—Depression Scale (CES-D), Patient Health Questionnaire, Center for Epidemiological Studies Depression Scale for Children (CES-DC), Clinically Useful Depression Outcome Scale, Diagnostic Inventory for Depression, Edinburgh Postnatal Depression Scale (EPDS), Inventory of Depressive Symptomatology, Geriatric Depression Scale (GDS), Hospital Anxiety and Depression Scale, Kutcher Adolescent Depression Scale (KADS), Major Depression Inventory (MDI), Montgomery-Asberg Depression Rating Scale (MADRS), Mood and Feelings Questionnaire (MFQ), Zung Self-Rating Depression Scale, or Cornell Scale for Depression in Dementia (CSDD).

In one embodiment, depression is reduced by at least one unit.

In another embodiment, the subject is afflicted with an anxiety disorder. In an embodiment, the anxiety disorder is generalized anxiety disorder (GAD), panic disorder, a phobic disorder, social phobia, agoraphobia, or trauma- and stressor-related disorders. In a further embodiment, the trauma- and stressor-related disorder is acute stress disorder (ASD), or posttraumatic stress disorder (PTSD). In another embodiment, the subject is afflicted with a depressive disorder.

In an embodiment, the depressive disorder is major depressive disorder, persistent depressive disorder, premenstrual dysphoric disorder, other depressive disorder, depressive disorder due to another medical condition, substance/medication-induced depressive disorder, perinatal depression, peripartum-onset depression, seasonal affective disorder, or psychotic depression.

The invention also provides pridopidine for use in reducing anxiety and/or depression in a subject. In an embodiment, the subject has been diagnosed with anxiety only. In another embodiment, the subject is experiencing at least one symptom of anxiety, wherein the at least one symptom comprises restlessness, heart palpitations, hyperventilation, heavy sweating, muscle twitching, weakness, lethargy, insomnia, nausea, repetitive behavior, or any combination thereof.

In an embodiment, the subject has been diagnosed with depression only. In another embodiment the subject is experiencing at least one symptom of depression, and wherein the at least one symptom of depression comprises depressed mood, anhedonia, low energy levels, feelings of guilt, psychomotor retardation, agitation, suicidal ideations poor concentration and indecisiveness, or any combination thereof.

In an embodiment, the composition comprising an amount of pridopidine or a pharmaceutically acceptable salt thereof is administered to the human subject once daily or twice daily.

In an embodiment, the composition comprising an amount of pridopidine and/or its analog, or a pharmaceutically acceptable salt thereof is administered to the human subject once daily or twice daily. In an embodiment, the composition comprising an amount of pridopidine and/or its analog, or a pharmaceutically acceptable salt thereof is administered to the human subject once daily. In one embodiment, the composition comprising an amount of pridopidine and/or its analog, or a pharmaceutically acceptable salt thereof is administered more often than once daily. In another embodiment, the composition comprising an amount of pridopidine and/or its analog, or a pharmaceutically acceptable salt thereof is administered 2-4 times a day. In one embodiment, the composition comprising an amount of pridopidine and/or its analog, or a pharmaceutically acceptable salt thereof is administered less than once a day. In another embodiment, the composition comprising an amount of pridopidine and/or its analog, or a pharmaceutically acceptable salt thereof is administered 2-4 times a week.

In an embodiment, the periodic administration continues for at least 3 days, more than 30 days, more than 42 days, 8 weeks or more, at least 12 weeks, at least 24 weeks, more than 24 weeks, or 6 months or more.

In an embodiment, the amount of pridopidine administered is 1 mg/day-315 mg/day, 22.5 mg/day-315 mg/day or 90 mg/day-315 mg/day.

In another embodiment, the amount of pridopidine administered is about 22.5 mg/day, about 45 mg/day, about 67.5 mg/day, about 90 mg/day, about 100 mg/day, about 112.5 mg/day, about 125 mg/day, about 135 mg/day, about 150 mg/day, about 180 mg/day, about 200 mg/day, about 250 mg/day, or about 315 mg/day.

In an embodiment, the composition comprising the amount of pridopidine or pharmaceutically acceptable salt thereof is administered orally. In an embodiment, the composition comprising the amount of pridopidine and/or its analog or pharmaceutically acceptable salt thereof is administered orally. In another embodiment, the composition comprising the amount of pridopidine and/or its analog or pharmaceutically acceptable salt thereof is administered parenterally. In another embodiment, the composition comprising the amount of pridopidine and/or its analog or pharmaceutically acceptable salt thereof is administered intravascularly. In another embodiment, the composition comprising the amount of pridopidine and/or its analog or pharmaceutically acceptable salt thereof is administered paracancerally. In another embodiment, the composition comprising the amount of pridopidine and/or its analog or pharmaceutically acceptable salt thereof is administered transmucosally. In another embodiment, the composition comprising the amount of pridopidine is administered transdermally. In another embodiment, the composition comprising the amount of pridopidine and/or its analog or pharmaceutically acceptable salt thereof is administered intramuscularly. In another embodiment, the composition comprising the amount of pridopidine and/or its analog or pharmaceutically acceptable salt thereof is administered untranasally. In another embodiment, the composition comprising the amount of pridopidine and/or its analog or pharmaceutically acceptable salt thereof is administered intravenously. In another embodiment, the composition comprising the amount of pridopidine and/or its analog or pharmaceutically acceptable salt thereof is administered intradermally. In another embodiment, the composition comprising the amount of pridopidine and/or its analog or pharmaceutically acceptable salt thereof is administered subcutaneously. In another embodiment, the composition comprising the amount of pridopidine and/or its analog or pharmaceutically acceptable salt thereof is administered sublingually. In another embodiment, the composition comprising the amount of pridopidine and/or its analog or pharmaceutically acceptable salt thereof is administered intraperitoneally. In another embodiment, the composition comprising the amount of pridopidine and/or its analog or pharmaceutically acceptable salt thereof is administered intraventricularly. In another embodiment, the composition comprising the amount of pridopidine and/or its analog or pharmaceutically acceptable salt thereof is administered intracranially. In another embodiment, the composition comprising the amount of pridopidine and/or its analog or pharmaceutically acceptable salt thereof is administered intravaginally. In another embodiment, the composition comprising the amount of pridopidine and/or its analog or pharmaceutically acceptable salt thereof is administered by inhalation. In another embodiment, the composition comprising the amount of pridopidine and/or its analog or pharmaceutically acceptable salt thereof is administered rectally. In another embodiment, the composition comprising the amount of pridopidine and/or its analog or pharmaceutically acceptable salt thereof is administered intratumorally.

In some embodiment, the composition for use in the method of this invention comprises pridopidine in combination of at least one of its analog compounds 1-8, or a pharmaceutically acceptable salt thereof:

(Compound 1)

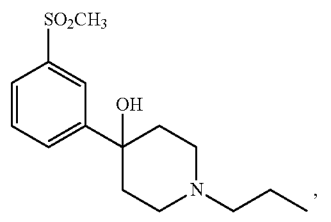

, (Compound 2)

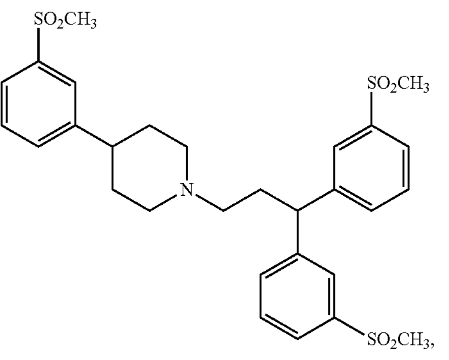

(Compound 3)

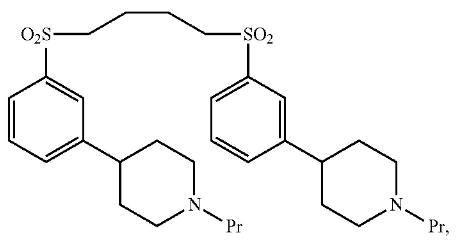

(Compound 4)

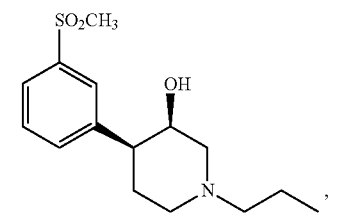

, (Compound 6)

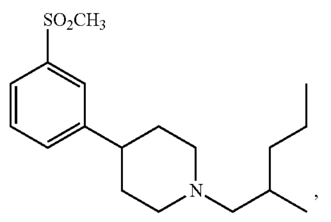

,

-continued (Compound 5)

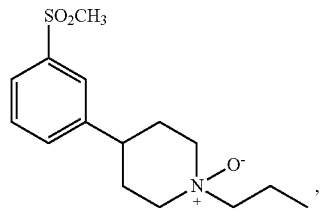

, (Compound 7)

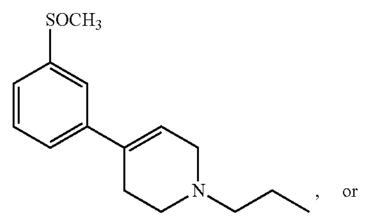

, or (Compound 8)

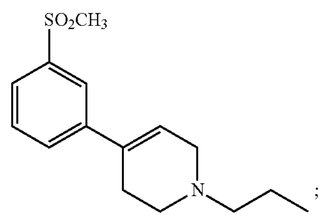

;

In other embodiments, the composition comprising pridopidine or a pharmaceutically acceptable salt thereof and at least one of Compounds 1-8 or pharmaceutically acceptable salt thereof for use in the methods of this invention—comprises a weight ratio between the pridopidine and at least one of compounds 1-8 in the range of 1:0.0001 to 1:0.1. In other embodiments, the weight ratio between the pridopidine or a pharmaceutically acceptable salt thereof and at least one of compounds 1-8 or a pharmaceutically acceptable salt thereof is in the range of 1:0.0005 to 1:0.005. In other embodiments, the weight ratio between the pridopidine or a pharmaceutically acceptable salt thereof and at least one of compounds 1-8 or a pharmaceutically acceptable salt thereof is in the range of 1:0.0005 to 1:0.0035. In other embodiments, the weight ratio between the pridopidine or a pharmaceutically acceptable salt thereof and at least one of compounds 1-8 or a pharmaceutically acceptable salt thereof is in the range of 1:0.005 to 1:0.1. In other embodiments, the weight ratio between the pridopidine or a pharmaceutically acceptable salt thereof and at least one of compounds 1-8 or a pharmaceutically acceptable salt thereof is in the range of 1:0.001 to 1:0.1. In other embodiments, the weight ratio between the pridopidine or a pharmaceutically acceptable salt thereof and at least one of compounds 1-8 or a pharmaceutically acceptable salt thereof is in the range of 1:0.001 to 1:0.005. In other embodiments, the weight ratio between the pridopidine or a pharmaceutically acceptable salt thereof and at least one of compounds 1-8 or a pharmaceutically acceptable salt thereof is in the range of 1:0.001 to 1:0.004.

In some embodiment, the composition for use in the method of this invention comprises an amount of pridopidine or pharmaceutically acceptable salt thereof in combination with at least compound 1 or pharmaceutically acceptable salt thereof. In other embodiments, the composition for use in the method of this invention comprises an amount of pridopidine or pharmaceutically acceptable salt thereof in combination with compound 1 or pharmaceutically acceptable salt thereof. In other embodiments, the composition for use in the method of this invention comprises an amount of pridopidine in combination with compound 1 or pharmaceutically acceptable salt thereof and compound 4 or pharmaceutically acceptable salt thereof. In other embodiments, the composition for use in the method of this invention comprises an amount of pridopidine or pharmaceutically acceptable salt thereof in combination with at least compound 2 or pharmaceutically acceptable salt thereof. In other embodiments, the composition for use in the method of this invention comprises an amount of pridopidine or pharmaceutically acceptable salt thereof in combination with at least compound 3 or pharmaceutically acceptable salt thereof. In other embodiments, the composition for use in the method of this invention comprises an amount of pridopidine or pharmaceutically acceptable salt thereof in combination with at least compound 4 or pharmaceutically acceptable salt thereof. In other embodiments, the composition for use in the method of this invention comprises an amount of pridopidine or pharmaceutically acceptable salt thereof in combination with at least compound 5 or pharmaceutically acceptable salt thereof. In other embodiments, the composition for use in the method of this invention comprises an amount of pridopidine or pharmaceutically acceptable salt thereof in combination with at least compound 6 or pharmaceutically acceptable salt thereof. In other embodiments, the composition for use in the method of this invention comprises an amount of pridopidine or pharmaceutically acceptable salt thereof in combination with at least compound 7 or pharmaceutically acceptable salt thereof. In other embodiments, the composition for use in the method of this invention comprises an amount of pridopidine or pharmaceutically acceptable salt thereof in combination with at least compound 8 or pharmaceutically acceptable salt thereof.

In other embodiments, the analog compounds 1-8 of pridopidine and their methods of preparation may be found in U.S. Pat. Nos. 10,130,621 and 10,406,145 the entire content of each of which is hereby incorporated by reference.

In an embodiment, the pharmaceutically acceptable salt of pridopidine comprises the hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, salicylate, sorbate, stearate, succinate, tartrate or toluene-p-sulphonate salt.

In an embodiment, the pharmaceutically acceptable salt of pridopidine is pridopidine hydrochloride. In another embodiment, the pharmaceutically acceptable salt of pridopidine is pridopidine hydrobromide. In another embodiment, the pharmaceutically acceptable salt of pridopidine is pridopidine nitrate. In another embodiment, the pharmaceutically acceptable salt of pridopidine is pridopidine perchlorate. In another embodiment, the pharmaceutically acceptable salt of pridopidine is pridopidine phosphate. In another embodiment, the pharmaceutically acceptable salt of pridopidine is pridopidine sulphate. In another embodiment, the pharmaceutically acceptable salt of pridopidine is pridopidine formate. In another embodiment, the pharmaceutically acceptable salt of pridopidine is pridopidine acetate. In another embodiment, the pharmaceutically acceptable salt of pridopidine is pridopidine aconate. In another embodiment, the pharmaceutically acceptable salt of pridopidine is pridopidine ascorbate. In another embodiment, the pharmaceutically acceptable salt of pridopidine is pridopidine benzenesulphonate. In another embodiment, the pharmaceutically acceptable salt of pridopidine is pridopidine benzoate. In another embodiment, the pharmaceutically acceptable salt of pridopidine is pridopidine cinnamate. In another embodiment, the pharmaceutically acceptable salt of pridopidine is pridopidine citrate. In another embodiment, the pharmaceutically acceptable salt of pridopidine is pridopidine embonate. In another embodiment, the pharmaceutically acceptable salt of pridopidine is pridopidine enantate. In another embodiment, the pharmaceutically acceptable salt of pridopidine is pridopidine fumarate. In another embodiment, the pharmaceutically acceptable salt of pridopidine is pridopidine glutamate. In another embodiment, the pharmaceutically acceptable salt of pridopidine is pridopidine glycolate. In another embodiment, the pharmaceutically acceptable salt of pridopidine is pridopidine lactate. In another embodiment, the pharmaceutically acceptable salt of pridopidine is pridopidine maleate. In another embodiment, the pharmaceutically acceptable salt of pridopidine is pridopidine malonate. In another embodiment, the pharmaceutically acceptable salt of pridopidine is pridopidine mandelate. In another embodiment, the pharmaceutically acceptable salt of pridopidine is pridopidine methanesulphonate. In another embodiment, the pharmaceutically acceptable salt of pridopidine is pridopidine naphthalene-2-sulphonate. In another embodiment, the pharmaceutically acceptable salt of pridopidine is pridopidine phthalate. In another embodiment, the pharmaceutically acceptable salt of pridopidine is pridopidine salicylate. In another embodiment, the pharmaceutically acceptable salt of pridopidine is pridopidine sorbate. In another embodiment, the pharmaceutically acceptable salt of pridopidine is pridopidine stearate. In another embodiment, the pharmaceutically acceptable salt of pridopidine is pridopidine succinate. In another embodiment, the pharmaceutically acceptable salt of pridopidine is pridopidine tartrate. In another embodiment, the pharmaceutically acceptable salt of pridopidine is pridopidine toluene-p-sulphonate.

In an embodiment, the pharmaceutically acceptable salt of each of the analog compounds of pridopidine (Compound 1-8) comprises the hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, salicylate, sorbate, stearate, succinate, tartrate or toluene-p-sulphonate salt.

In an embodiment, the subject is a human patient.

The invention also provides a package comprising:

a) a pharmaceutical composition comprising an amount of pridopidine and/or its analog or a pharmaceutically acceptable salt thereof and a pharmaceutically acceptable carrier;

b) instructions for use of the pharmaceutical composition to treat a subject afflicted with a disease or disorder associated with a cognitive deficit.

In an embodiment, the disease or disorder is a disease or disorder associated with NMDA receptor. In an embodiment, the cognitive deficit is memory loss.

In an embodiment, the pharmaceutically acceptable salt of pridopidine is pridopidine hydrochloride.

In an embodiment, the amount of pridopidine in the pharmaceutical composition is 1 mg-315 mg, 22.5 mg-315 mg or 90 mg-315 mg. In another embodiment, the amount of pridopidine in the pharmaceutical composition is about 10 mg, about 20 mg, about 22.5 mg, about 30 mg, about 40 mg, about 45 mg, about 50 mg, about 67.5, mg, about 70 mg, about 80 mg, about 90 mg, about 100 mg, about 112.5 mg, about 125 mg, about 135 mg, about 150 mg, about 180 mg, about 200 mg, about 250 mg, about 315 mg, or any ranges thereof.

The invention also provides a therapeutic package for dispensing to, or for use in dispensing to, a subject afflicted with a disease or disorder associated with a cognitive deficit, which comprises:

a) one or more unit doses, each such unit dose comprising an amount of pridopidine and/or its analog, or a pharmaceutically acceptable salt thereof, wherein the amount of said pridopidine and/or its analog in said unit dose is effective, upon administration to said subject, to treat the subject, and b) a finished pharmaceutical container therefor, said container containing said unit dose or unit doses, said container further containing or comprising labeling directing the use of said package in the treatment of said subject.

In an embodiment, the disease or disorder is a disease or disorder associated with NMDA receptor. The invention also provides a pharmaceutical composition comprising an amount of pridopidine and/or its analog, or a pharmaceutically acceptable salt thereof for use in treating a subject afflicted with a disease or disorder associated with a cognitive deficit.

In an embodiment, the pharmaceutical composition is in a solid, a capsule or a tablet form.

In an embodiment, the cognitive deficit is memory loss.

In an embodiment, the pharmaceutically acceptable salt of pridopidine is pridopidine hydrochloride.

In an embodiment, the amount of pridopidine in the pharmaceutical composition is 1 mg-315 mg, 22.5 mg-315 mg or 90 mg-315 mg. In another embodiment, the amount of pridopidine in the pharmaceutical composition is about 10 mg, about 20 mg, about 22.5 mg, about 30 mg, about 40 mg, about 45 mg, about 50 mg, about 67.5, mg, about 70 mg, about 80 mg, about 90 mg, about 100 mg, about 112.5 mg, about 125 mg, about 135 mg, about 150 mg, about 180 mg, about 200 mg, about 250 mg, about 315 mg, or any ranges thereof.

The invention also provides a pharmaceutical composition in a unit dosage form, useful in treating a subject afflicted with a disease or disorder associated with a cognitive deficit, which comprises an amount of pridopidine or a pharmaceutically acceptable salt thereof, wherein the amount of said pridopidine in said composition is effective, upon administration to said subject of one or more of said unit dosage forms of said composition, to treat the subject.

In an embodiment, the disease or disorder is a disease or disorder associated with NMDA receptor. The invention also provides a pharmaceutical composition in a unit dosage form, useful in treating a subject afflicted with a depression or anxiety not caused by Huntington's disease, which comprises an amount of pridopidine and/or its analog or a pharmaceutically acceptable salt thereof, wherein the amount of said pridopidine in said composition is effective, upon administration to said subject of one or more of said unit dosage forms of said composition, to treat the subject.

The invention also provides a pharmaceutical composition in a unit dosage form, useful in treating a subject afflicted with a depression or anxiety associated with a cognitive deficit, which comprises an amount of pridopidine or a pharmaceutically acceptable salt thereof, wherein the amount of said pridopidine in said composition is effective, upon administration to said subject of one or more of said unit dosage forms of said composition, to treat the subject.

The invention also provides a package comprising:

a) a pharmaceutical composition; and b) instructions for use of the pharmaceutical composition to treat a subject afflicted with a disease or disorder associated with a cognitive deficit.

This invention also provides pridopidine and/or its analog, or a pharmaceutically acceptable salt thereof for use in treating a disease or disorder associated with a cognitive deficit.

This invention also provides a use of pridopidine and/or its analog, or a pharmaceutically acceptable salt thereof in the manufacture of a medicament for treating a disease or disorder associated with a cognitive deficit.

For the foregoing and following embodiments, each embodiment disclosed herein is contemplated as being applicable to each of the other disclosed embodiments. For instance, the elements recited in the method embodiments can be used in the pharmaceutical composition, package, and use embodiments described herein and vice versa.

The invention further provides a method of treating a subject afflicted with a disease selected from Alzheimer's disease and mild cognitive impairment (MCI), comprising periodically administering to the subject a pharmaceutical composition comprising an amount of pridopidine and/or its analog, or a pharmaceutically acceptable salt thereof effective to treat the subject.

The invention further provides a method of treating a subject afflicted with a disease selected from Alzheimer's disease and mild cognitive impairment (MCI), comprising periodically administering to the subject a pharmaceutical composition comprising an amount of pridopidine and/or its analog, or a pharmaceutically acceptable salt thereof effective to treat the subject, wherein the disease is associated with DMN dysfunction.

In an embodiment, the amount of pridopidine and/or its analog, is effective to reduce neurotoxicity in the subject. In another embodiment, the amount of pridopidine and/or its analog, is effective to inhibit the progression Alzheimer's disease or MCI in the subject. In a further embodiment, the amount of pridopidine and/or its analog, is effective to reduce one or more symptoms of Alzheimer's disease or MCI in the subject.

In an embodiment, the one or more symptoms are selected from the group consisting of cognitive impairment, function performance impairment, impairment in basic and instrumental activities of daily living, reduced quality of life and psychopathology.

In one embodiment, the one or more symptoms are measured by the Clinician's Interview-based Impression of Change plus Caregiver Input (CIBIC-Plus), Severity Impairment Battery (SIB), Alzheimer's Disease Cooperative Study Clinician's Global Impression of Change (ADCS-CCGIC), Alzheimer's Disease Assessment Scale-Cognitive (ADAS-Cog), Clinical Dementia Rating (CDR), CIBIC Plus-J Score Mental Function Impairment Scale (MENFIS), Mini-mental state exam (MMSE), Mini-cog test, Blessed Information-Memory-Concentration Test (BIMC), Cambridge Neuropsychological Test Automated Battery (CANTAB), Alzheimer's Disease Cooperative Study Activities of Daily Living Inventory (ADCS-ADL) Score, ADCS-ADL-SIV (severe impairment version), Disability Assessment for Dementia (DAD), the Functional Assessment Questionnaire (FAQ), Instrumental Activities of Daily Living (IADL), Physical Self-Maintenance Scale (PSMS) and Progressive Deterioration Scale (PDS), the Neuropsychiatric Inventory (NPI) score, CIBIC Plus-J Score Behavioral Pathology in Alzheimer's Disease Rating Scale (Behave-A D), CIBIC Plus-J Score Mental Function Impairment Scale (MENFIS), the Resource Utilization in Dementia-Lite (RUD-Lite), EuroQol 5-Dimensional Health-Related Quality of Life Scale (EQ-5D), the Clinical Global Impression of Change (CGIC), the Clinical Interview-Based Impression (CIBI), the Global Deterioration Scale (GDS), A Cognitive Assessment Battery for Clinical Trials in Huntington's Disease (HD-CAB), Montreal Cognitive Assessment (MoCA), Stroop Word Reading (SWR) or Symbol Digit Modalities Test (SDMT).

In an embodiment, the periodic administration is oral.

In an embodiment, between 1 mg-315 mg, 22.5-315 mg or 90 mg-315 mg pridopidine is administered to the patient per day. In another embodiment, the amount of pridopidine in the pharmaceutical composition is about 10 mg, about 20 mg, about 22.5 mg, about 30 mg, about 40 mg, about 45 mg, about 50 mg, about 67.5, mg, about 70 mg, about 80 mg, about 90 mg, about 100 mg, about 112.5 mg, about 125 mg, about 135 mg, about 150 mg, about 180 mg, about 200 mg, about 250 mg, about 315 mg, or any ranges thereof In an embodiment, the amount of pridopidine is administered by a unit dose of about 10 mg, about 20 mg, about 22.5 mg, about 30 mg, about 40 mg, about 45 mg, about 50 mg, about 67.5, mg, about 70 mg, about 80 mg, about 90 mg, about 100 mg, about 112.5 mg, about 125 mg, about 135 mg, about 150 mg, about 180 mg, about 200 mg, about 250 mg, about 315 mg, or any ranges thereof.

In an embodiment, the unit dose is administered once daily.

In an embodiment, the unit dose is administered more than once daily. In one embodiment, the unit dose is administered 2-4 times a day. In another embodiment, the unit dose is administered twice per day. In one embodiment, the unit dose is administered less than once a day. In one embodiment, the unit dose is administered 2-4 times per week.

In an embodiment, the pridopidine is in the form of pridopidine hydrochloride.

In an embodiment, the subject is a naïve subject.

In an embodiment, the method further comprises the administration of a drug approved to treat Alzheimer's disease or MCI. In another embodiment, the method further comprises the administration of a psychiatric drug. In an embodiment, the drug approved to treat Alzheimer's disease is donepezil, rivastigmine, galantamine, tacrine, or memantine.

In an embodiment, the method further comprises the administration of a psychiatric drug, an antidepressant drug, anxiolytics, antipsychotic medications or combinations thereof.

In an embodiment, the method further comprises the administration of one or more antidepressants. In another embodiment, the antidepressant is selected from the group consisting of citalopram, fluoxetine, paroxeine, sertraline, and trazodone.

In an embodiment, the method further comprises the administration of one or more anxiolytics. In another embodiment, the anxiolytic is selected from the group consisting of lorazepam and oxazepam.

In an embodiment, the method further comprises the administration of one or more antipsychotic medications. In another embodiment, the antipsychotic medication is selected from the group consisting of aripiprazole, clozapine, haloperidol, olanzapine, quetiapine, risperidone, and ziprasidone. The invention also provides pridopidine, its analog or a pharmaceutically acceptable salt thereof for use in treating a human subject afflicted with Alzheimer's disease.

The Invention provides a method of treating a human subject afflicted with epilepsy, comprising administering to the subject a pharmaceutical composition comprising an amount of pridopidine, its analog or a pharmaceutically acceptable salt thereof.

In an embodiment, the amount of pridopidine, its analog or a pharmaceutically acceptable salt thereof is administered to the human subject once daily. In one embodiment, the amount of pridopidine or a pharmaceutically acceptable salt thereof is administered more often than once daily.

In an embodiment, the amount of pridopidine administered is 1 mg/day-315 mg/day, 22.5 mg/day-315 mg/day or 90 mg/day-315 mg/day.

In an embodiment, the amount of pridopidine is administered orally. In another embodiment, the amount of pridopidine is administered parenterally. In another embodiment, the amount of pridopidine is administered intravascularly. In another embodiment, the amount of pridopidine is administered paracancerally. In another embodiment, the amount of pridopidine is administered transmucosally. In another embodiment, the amount of pridopidine is administered transdermally, In another embodiment, the amount of pridopidine is administered intramuscularly. In another embodiment, the amount of pridopidine is administered untranasally. In another embodiment, the amount of pridopidine is administered intravenously. In another embodiment, the amount of pridopidine is administered intradermally. In another embodiment, the amount of pridopidine is administered subcutaneously. In another embodiment, the amount of pridopidine is administered sublingually. In another embodiment, the amount of pridopidine is administered intraperitoneally. In another embodiment, the amount of pridopidine is administered intraventricularly. In another embodiment, the amount of pridopidine is administered intracranially. In another embodiment, the amount of pridopidine is administered intravaginally. In another embodiment, the amount of pridopidine is administered by inhalation. In another embodiment, the amount of pridopidine is administered rectally. In another embodiment, the amount of pridopidine is administered intratumorally.

In an embodiment, the pharmaceutically acceptable salt of pridopidine is pridopidine hydrochloride.

The invention also provides pridopidine or a pharmaceutically acceptable salt thereof for the manufacture of a medicament for use in treating a subject afflicted with Alzheimer's disease.

The invention also provides a pharmaceutical composition comprising an effective amount of pridopidine or a pharmaceutically acceptable salt thereof for treating Alzheimer's disease.

The invention also provides a pharmaceutical composition comprising pridopidine or a pharmaceutically acceptable salt thereof for use in treating a subject suffering from Alzheimer's disease.

The invention also provides a package comprising:

a) a pharmaceutical composition comprising an amount of pridopidine; and
b) instructions for use of the pharmaceutical composition to treat a subject afflicted with a Alzheimer's disease.

The invention also provides a therapeutic package for dispensing to, or for use in dispensing to, a subject afflicted with Alzheimer's disease, which comprises:

a) one or more unit doses, each such unit dose comprising an amount of pridopidine thereof, wherein the amount of said pridopidine in said unit dose is effective, upon administration to said subject, to treat the subject, and b) a finished pharmaceutical container therefor, said container containing said unit dose or unit doses, said container further containing or comprising labeling directing the use of said package in the treatment of said subject.

The method of reducing neurotoxicity in a human patient afflicted with Alzheimer's disease, comprising periodically administering to the patient a pharmaceutical composition comprising pridopidine or a pharmaceutically acceptable salt thereof effective to treat the subject.

In an embodiment, the subject is a human subject.

The invention also provides a package comprising:

a) a first pharmaceutical composition comprising an amount of pridopidine and a pharmaceutically acceptable carrier;

b) a second pharmaceutical composition comprising an amount of a drug approved to treat Alzheimer's disease and a pharmaceutically acceptable carrier; and c) instructions for use of the first and second pharmaceutical compositions together to treat a subject afflicted with a Alzheimer's disease.

In an embodiment, the drug approved to treat Alzheimer's disease is donepezil, rivastigmine, galantamine, tacrine, or memantine.

The invention also provides a package comprising:

a) a first pharmaceutical composition comprising an amount of pridopidine and a pharmaceutically acceptable carrier;

b) a second pharmaceutical composition comprising an amount of one or more antidepressants, anxiolytics, or antipsychotic medications, and a pharmaceutically acceptable carrier; and c) instructions for use of the first and second pharmaceutical compositions together to treat a subject afflicted with Alzheimer's disease.

In an embodiment, the antidepressant is selected from the group consisting of citalopram, fluoxetine, paroxeine, sertraline, and trazodone.

In an embodiment, the anxiolytic is selected from the group consisting of lorazepam and oxazepam.

In an embodiment, the antipsychotic medication is selected from the group consisting of aripiprazole, clozapine, haloperidol, olanzapine, quetiapine, risperidone, and ziprasidone.

The invention also provides a therapeutic package for dispensing to, or for use in dispensing to, a subject afflicted with Alzheimer's disease, which comprises:

a) one or more unit doses, each such unit dose comprising:
   i) an amount of pridopidine and/or its analog or a pharmaceutically acceptable salt thereof, and
   ii) an amount of a drug approved to treat Alzheimer's disease wherein the respective amounts of said pridopidine and/or its analog and said drug approved to treat Alzheimer's disease in said unit dose are effective, upon concomitant administration to said subject, to treat the subject, and b) a finished pharmaceutical container therefor, said container containing said unit dose or unit doses, said container further containing or comprising labeling directing the use of said package in the treatment of said subject.

In an embodiment, the drug approved to treat Alzheimer's disease is donepezil, rivastigmine, galantamine, tacrine, or memantine.

The invention also provides a therapeutic package for dispensing to, or for use in dispensing to, a subject afflicted with Alzheimer's disease, which comprises:

a) one or more unit doses, each such unit dose comprising:
   i) an amount of pridopidine and/or its analog or a pharmaceutically acceptable salt thereof and
   ii) an amount of one or more antidepressants, anxiolytics, or antipsychotic medications wherein the respective amounts of said pridopidine and said one or more antidepressants, anxiolytics, or antipsychotic medications in said unit dose are effective, upon concomitant administration to said subject, to treat the subject, and b) a finished pharmaceutical container therefor, said container containing said unit dose or unit doses, said container further containing or comprising labeling directing the use of said package in the treatment of said subject.

In an embodiment, the antidepressant is selected from the group consisting of citalopram, fluoxetine, paroxeine, sertraline, and trazodone.

In an embodiment, the anxiolytic is selected from the group consisting of lorazepam and oxazepam.

In an embodiment, the antipsychotic medication is selected from the group consisting of aripiprazole, clozapine, haloperidol, olanzapine, quetiapine, risperidone, and ziprasidone.

Combinations of the above-described embodiments are also within the scope of the invention.

The antipsychotic medication may be used to treat hallucinations, delusions, aggression, agitation, hostility and/or uncooperativeness. The anxiolytic may be used to treat anxiety, restlessness, verbally disruptive behavior and/or resistance. The antidepressant may be used to treat low mood and irritability (www.alz.org).

For the foregoing embodiments, each embodiment disclosed herein is contemplated as being applicable to each of the other disclosed embodiments. In addition, the elements recited in pharmaceutical composition embodiments can be used in the method and use embodiments described herein.

Terms

As used herein, and unless stated otherwise, each of the following terms shall have the definition set forth below.

As used herein, "administering to the subject" means the giving of, dispensing of, or application of medicines, drugs, or remedies to a subject to relieve, cure or reduce the symptoms associated with a disease, disorder or condition, e.g., a pathological condition. Oral administration is one way of administering the instant compounds to the subject.

As used herein, "cognitive function" means an intellectual process by which one becomes aware of, perceives, or comprehends ideas. Cognitive function involves all aspects of perception, thinking, reasoning, and memory, including short term memory.

As used herein, "improving cognitive function" includes slowing, stopping, or reversing the progression of a cognitive deficit, in addition to increasing cognitive function. Areas of cognitive function are described in Fioravanti et al (2012).

As used herein, a "cognitive deficit" is an inclusive term to describe any characteristic that acts as a barrier to cognitive function. Cognitive deficits can include loss of higher reasoning, forgetfulness, learning disabilities, concentration difficulties, decreased intelligence, and other reductions in mental functions. Cognitive deficits may be congenital or caused by environmental factors, brain injuries, neurological disorders, or mental illness. Cognitive impairments and cognitive dysfunctions are also considered cognitive deficits.

As used herein, "short term memory" is the capacity to recognize, recall and regurgitate small amounts of information shortly after its occurrence.

MK-801, or Dizocilpine, is an NMDA receptor antagonist.

As used herein, a "disease or disorder associated with an NMDA receptor" is any disease or disorder related to or resulting from NMDA receptor imbalance or dysfunction. This can include, but is not limited to, diseases or disease symptoms that can be induced or caused by NMDA receptor antagonists such as MK-801, diseases which may be treated by NMDA receptor antagonists such as MK-801, or diseases in which NMDA receptor antagonists such as MK-801 increase or decrease the severity of the symptoms.

As used herein, to "treat" or "treating" encompasses, e.g., inducing inhibition, regression, or stasis of a disorder and/or disease, e.g. depression, or alleviating, lessening, suppressing, inhibiting, reducing the severity of, eliminating or substantially eliminating, or ameliorating a symptom of the disease or disorder. As used herein, "inhibition" of disease progression or disease complication in a subject means preventing, delaying or reducing the disease progression and/or disease complication in the subject. This includes, for example, delaying the progression of one of more symptoms in the subject, including but not limited to delaying the progression of: cognitive impairment, intellectual disability, learning disabilities (e.g., having difficulty learning new skills), developmental delays (e.g., not sitting, walking, or talking at the same time as other children the same age), social and behavior problems (e.g., making eye contact, anxiety, trouble paying attention, hand flapping, acting and speaking without thinking, and being very active), anxiety and hyperactive behavior, hypersensitivity to sensory stimuli, altered gastrointestinal function, autistic symptoms (e.g., shyness, poor eye contact, and social anxiety in mild cases to hand flapping, hand biting and preservative speech in the severely affected), attention deficit and hyperactivity, behavioral disturbances (e.g., irritability, aggression and self-injurious behaviors), seizures, obsessive-compulsive behavior and altered gastrointestinal function.

In some embodiments, symptoms of anxiety include but are not limited to restlessness, heart palpitations, hyperventilation, heavy sweating, muscle twitching, weakness, lethargy, insomnia, nausea, repetitive behavior, or any combination thereof.

In some embodiments, symptoms of depression include but are not limited to depressed mood, anhedonia, low energy levels, feelings of guilt, psychomotor retardation, agitation, suicidal ideations poor concentration, indecisiveness, or any combination thereof.

The methods of the present invention are useful for improving cognitive function in diseases and disorders associated with both cognitive deficits and the NMDA receptor. The following diseases and disorders are associated with cognitive deficits and the NMDA receptor: schizophrenia, autism (Saunders, 2012), epilepsy (van Rijckevorsel 2006, Stafstrom 1997), anxiety disorders (Ferreri 2011, Dietz 2014), major depressive disorder (MDD) (Keefe 2014, Rapaport 2009), Parkinson's disease (Dubois 1997, Jonkers 2000), Alzheimer's disease (U.S. Patent Publication No. 20130065966), tardive dyskinesia (Krabbendam 2000, Seo 1997), Depression (Austin 2001, Zeynep 2013), sickle cell anemia (Steen 2005, U.S. Pat. No. 8,680,042), stroke (Cumming 2013, U.S. Patent Publication No. 20130065966), chronic pain syndrome (Hart 2003, Zeynep 2013), addiction (Gould 2010, U.S. Pat. No. 5,321,012), and Huntington's disease (Foroud 1995, U.S. Patent Publication No. 20130065966).

Other diseases and disorders which may be treated by the methods of this invention include: memory deficit, mild cognitive impairment, memory loss, a memory deficit related to brain injury or a post-stroke event, a learning deficiency, and behavioral and cognitive problems associated with brain tumors.

Additional diseases and disorders which may be treated by the methods of this invention include: dementia, dementia associated with Lewy Bodies, age-related cognitive decline, psychosis, attention deficit disorder (ADHD), bipolar disorder, brain injury, mood and affective disorders, Tourette's syndrome, mental retardation, progressive supranuclear palsy, Creutzfeldt-Jacob disease, vascular dementia, Corticobasal Degeneration, Creutzfeldt-Jakob Disease, and Pick's disease.

As used herein, an "amount" or "dose" of pridopidine as measured in milligrams refers to the milligrams of pridopidine (4-[3-(methylsulfonyl)phenyl]-1-propyl-piperidine) present in a preparation, regardless of the form of the preparation. For example, a unit dose containing "90 mg pridopidine" means the amount of pridopidine base in a preparation is 90 mg, regardless of the form of the preparation. Thus, when in the form of a salt, e.g. pridopidine hydrochloride salt, the weight of the salt form necessary to provide a dose of 90 mg pridopidine would be greater than 90 mg due to the presence of the salt.

As used herein, a "unit dose", "unit doses" and "unit dosage form(s)" mean a single drug administration entity/entities.

As used herein, "about" in the context of a numerical value or range means±10% of the numerical value or range recited or claimed.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat cognitive deficit. The specific effective amount varies with such factors as the particular condition being treated, the physical condition of the patient, the type of mammal being treated, the duration of the treatment, the nature of concurrent therapy (if any), and the specific formulations employed and the structure of the compounds or its derivatives.

As used herein, to "treat" or "treating" encompasses, e.g., inducing inhibition, regression, or stasis of a disorder and/or disease, e.g. AD, or alleviating, lessening, suppressing, inhibiting, reducing the severity of, eliminating or substantially eliminating, or ameliorating a symptom of the disease or disorder.

As used herein, "inhibition" of disease progression or disease complication in a subject means preventing, delaying or reducing the disease progression and/or disease complication in the subject. This includes, for example, delaying the progression of one of more symptoms in the subject, including for example delaying the progression of cognitive impairment, delaying the deterioration in function performance and basic and instrumental activities of daily living, delaying the deterioration of quality of life or delaying the deterioration of psychopathology.

A "symptom" associated with AD includes any clinical or laboratory manifestation associated with AD and is not limited to what the subject can feel or observe. Symptoms of AD include but are not limited to the impairment and/or deterioration in cognition (e.g., memory and behavior, judgment/problem solving, attention, concentration, naming, comprehension, reasoning, language, communication, orientation and praxis), functional performance (e.g., grooming, dressing, walking including balance, bathing, feeding and toileting) basic and instrumental activities of daily living (e.g., shopping, preparing meals, using household appliances, conducting hobbies and interests, keeping appointments and reading), quality of life (e.g., mobility, self-care, daily activities, pain/discomfort, mood, relationships, overall physical condition, anxiety and depression, swallowing), or psychopathology (e.g. paranoid and delusional ideation, hallucinations, activity disturbances, diurnal rhythm disturbances, aggressiveness, affective disorders and anxieties, and phobias).

Various assessment tools are accepted in the field, which serve to evaluate the status of AD patients. For example, Cognition may be evaluated by various assessment tools exemplified by the Clinician Interview-Based Impression of Change, plus carer interview (CIBIC-Plus), Severity Impairment Battery (SIB), Alzheimer's Disease Cooperative Study Clinician's Global Impression of Change (ADCS-CCGIC), Alzheimer's Disease Assessment Scale-Cognitive (ADAS-Cog), Clinical Dementia Rating (CDR), CIBIC Plus-J Score Mental Function Impairment Scale (MENFIS), Mini-mental state exam (MMSE), Mini-cog test, Blessed Information-Memory-Concentration Test (BIMC), and Cambridge Neuropsychological Test Automated Battery (CANTAB). Functional performance and basic and instrumental activities of daily living can be evaluated for example using Alzheimer's Disease Cooperative Study Activities of Daily Living Inventory (ADCS-ADL) Score, ADCS-ADL-SIV (severe impairment version), Disability Assessment for Dementia (DAD), Functional Assessment Questionnaire (FAQ), Instrumental Activities of Daily Living (IADL), Physical Self-Maintenance Scale (PSMS) and Progressive Deterioration Scale (PDS). Psychopathology can be evaluated for example by Neuropsychiatric Inventory (NPI) score, CIBIC Plus-J Score Behavioral Pathology in Alzheimer's Disease Rating Scale (Behave-A D), CIBIC Plus-J Score Mental Function Impairment Scale (MENFIS). Quality of life can be evaluated for example by the Resource Utilization in Dementia-Lite (RUD-Lite), EuroQol 5-Dimensional Health-Related Quality of Life Scale (EQ-5D), including for example Proxy Version (EQ-5D Proxy). In addition, global assessment measures may be used to evaluate the patient's status, indulging for example Clinical Global Impression of Change (CGIC), Clinical Interview-Based Impression (CIBI), Global Deterioration Scale (GDS).

Anxiety Rating Scales

The anxiety rating scales listed herein are known to those skilled in the art. For example, the Beck Anxiety Inventory (BAI) is a measure of anxiety that has 21 items which are summed to obtain a total score from 0-63, in which a score of 0-9 is generally considered to mean normal or no anxiety; a score of 10-18 is generally considered to mean mild to moderate anxiety; a score of 19-29 is generally considered to mean moderate to severe anxiety; and a score of 30-63 is generally considered to mean severe anxiety (Julian 2011). Another anxiety rating scale is the Hospital Anxiety and Depression Scale-Anxiety (HADS-A) which has 7 items (Julian 2011). This scale evaluates common dimensions of anxiety and can be used to detect and quantify magnitude of symptoms of anxiety (Julian 2011). The total score for HADS-A can range from 0 to 21 and the following guidelines are recommended for the interpretation of scores: 0-7 for normal or no anxiety, 8-10 for mild anxiety, 11-14 for moderate anxiety, and 12-21 for severe anxiety (Julian 2011). Other anxiety rating scales are described in Hamilton 1959, Leary 1983, and Connor 2000. As used here, "reducing anxiety by at least one increment" means that the patient's anxiety as measured by at least one of the specific anxiety rating scales is lessened. For example, the STAI is an anxiety rating scale which has two subtest, a State Anxiety Scale (S-Anxiety) and a Trait Anxiety Scale (T-Anxiety) (Julian 2011). The range of scores for each subtest is 20-80 with a higher score indicating greater anxiety (Julian 2011). Therefore, a subject obtains a score of between 40 and 160 after completing the STAI. The subject's anxiety is reduced by at least one increment if the subject's STAI score is reduced by 1 or more points. The patient anxiety may also be measured by one of the following anxiety rating scales: State-Trait Anxiety Inventory (STAI), the Fear Survey Schedule, Beck Anxiety Inventory (BAI), Brief Fear of Negative Evaluation Scale—BFNE, Clinician Administered PTSD Scale (CAPS), Daily Assessment of Symptoms—Anxiety, Generalized Anxiety Disorder 7 (GAD-7), Hamilton Anxiety Scale (HAM-A), Hospital Anxiety and Depression Scale (HADS-A), Leibowitz Social Anxiety Scale (LSAS), Overall Anxiety Severity and Impairment Scale (OASIS), Panic and Agoraphobia Scale (PAS), Panic Disorder Severity Scale (PDSS), PTSD Symptom Scale—Self-Report Version, Social Phobia Inventory (SPIN), Trauma Screening Questionnaire, Yale-Brown Obsessive Compulsive Scale (Y-BOCS), and the Zung Self-Rating Anxiety Scale. Depression Rating Scales The depression rating scales listed herein are known to those skilled in the art. For example, Hamilton Depression Rating Scale (HAM-D) may be used to determine a patient's level of depression. The HAM-D lists 21 items, but scoring is based on the first 17 in which 0-6 is considered normal, 7-17 is considered mild depression, 18-24 is considered moderate depression, and 25 and greater is considered severe depression (Hamilton 1960). Other depression rating scales are described in Bech 2001, Bech 2006, and Strik 2001.

As used here, "reducing depression by at least one increment" means that the patient's depression as measured by at least one of the specific depression rating scales is lessened. For example, in the HAM-D scale discussed above, the subject's depression is reduced by at least one increment if the subject's HAM-D score is reduced by 1 or more points.

The patient's depression may also be measured by one of the following depression rating scales: Hamilton Rating Scale for Depression (HAM-D), Beck Depression Inventory (BDI), Beck Hopelessness Scale, Centre for Epidemiological Studies—Depression Scale (CES-D), Patient Health Questionnaire, Center for Epidemiological Studies Depression Scale for Children (CES-DC), Clinically Useful Depression Outcome Scale, Diagnostic Inventory for Depression, Edinburgh Postnatal Depression Scale (EPDS), Inventory of Depressive Symptomatology, Geriatric Depression Scale (GDS), Hospital Anxiety and Depression Scale, Kutcher Adolescent Depression Scale (KADS), Major Depression Inventory (MDI), Montgomery-Asberg Depression Rating Scale (MADRS), Mood and Feelings Questionnaire (MFQ), Zung Self-Rating Depression Scale, or Cornell Scale for Depression in Dementia (CSDD).

A "biomarker" is a measurable parameter that serves as an indication to the severity, subtype or stage of the disease. Biomarkers for AD include but are not limited to Amyloid Beta (Aβ) 1-42 plasma concentration, change in glucose metabolism in the brain measured for example by Positron Emission Tomography (PET), and change in hyppocampal volume, measured for example by Magnetic Resonance Imaging (MRI). An increased Amyloid Beta (Aβ) 1-42 plasma concentration, reduced glucose metabolism in the brain, and reduced hippocampal volume are considered to be associated with increased severity of the disease.

As used herein, "a subject afflicted with AD" means a subject diagnosed as suffering from AD, including for example subjects diagnosed as suffering from "definite AD", "probable AD" or "possible AD". In an embodiment, the subject is diagnosed as according to the 1984 Criteria, also called the NINCDS-ADRDA Alzheimer's criteria (McKhann et al. 1984). In another embodiment, the subject is diagnosed according to the revised criteria for diagnosis of Alzheimer's disease of the National Institute on Aging-Alzheimer's Association diagnostic guidelines for Alzheimer's disease (McKhann et al. 2011). In another embodiment, the subject is diagnosed according to the DSM-IV criteria. In another embodiment, the subject is diagnosed according to the International Classification of Diseases.

"Adverse event" or "AE" means any untoward medical occurrence in a clinical trial subject administered a medicinal product and which does not have a causal relationship with the treatment. An adverse event can therefore be any unfavorable and unintended sign including an abnormal laboratory finding, symptom, or diseases temporally associated with the use of an investigational medicinal product, whether or not considered related to the investigational medicinal product.

As used herein, a subject at "baseline" is a subject prior to initiating periodic administration of pridopidine.

As used herein, a "naïve subject" or a "naïve patient" with respect to a drug or therapy means that the subject has not previously received the drug or therapy.

A "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

As used herein, the term "pridopidine" refers to pridopidine free base. In certain embodiments, the term "pridopidine" refer to pridopidine free base and at least one of its analogs—compounds 1-8. In certain embodiments, pridopidine and/or its analog also includes any pharmaceutically acceptable salt, such as the HCl salt or tartrate salt. In some embodiments of the invention as described herein, the pridopidine is in the form of its salt. In some embodiments of the invention as described herein, the pridopidine is in the form of a hydrochloride salt. In some embodiments of the invention as described herein, the pridopidine is in the form of pridopidine base As used herein, the term "its analog" refers to an analog of pridopidine represented by compounds 1-8 or a pharmaceutically acceptable salt thereof:

(Compound 1)

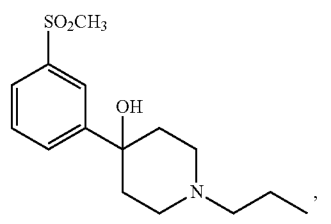

,

-continued (Compound 2)

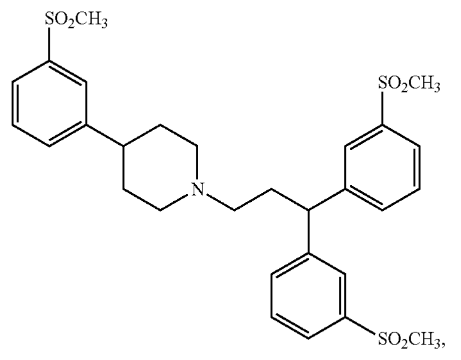

(Compound 3)

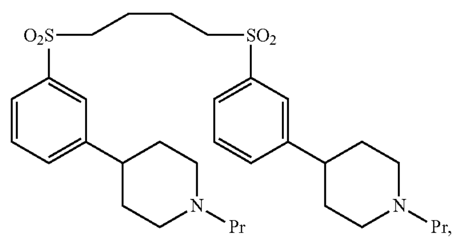

(Compound 4)

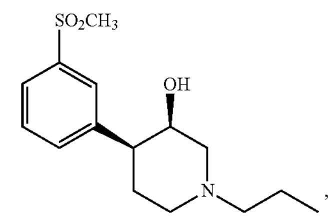

, (Compound 6)

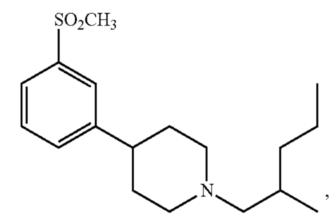

, (Compound 5)

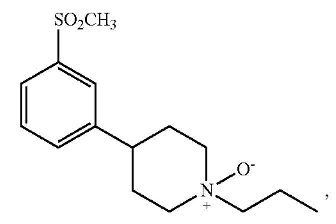

, (Compound 7)

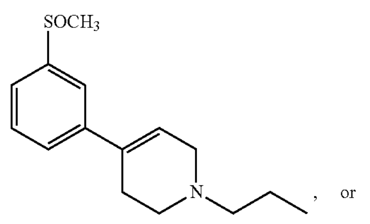

, or

-continued (Compound 8)

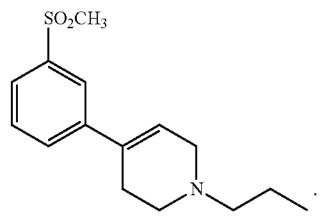

As used herein, "combination" means an assemblage of reagents for use in therapy either by simultaneous or contemporaneous administration. Simultaneous administration refers to administration of an admixture (whether a true mixture, a suspension, an emulsion or other physical combination) of the pridopidine and the second compound. In this case, the combination may be the admixture or separate containers of the pridopidine and the second compound that are combined just prior to administration. Contemporaneous administration refers to the separate administration of the pridopidine and the second compound at the same time, or at times sufficiently close together that an additive or preferably synergistic activity relative to the activity of either the the pridopidine and the second compound alone is observed.

As used herein, "concomitant administration" or administering "concomitantly" means the administration of two agents given in close enough temporal proximately to allow the individual therapeutic effects of each agent to overlap.

As used herein, "add-on" or "add-on therapy" means an assemblage of reagents for use in therapy, wherein the subject receiving the therapy begins a first treatment regimen of one or more reagents prior to beginning a second treatment regimen of one or more different reagents in addition to the first treatment regimen, so that not all of the reagents used in the therapy are started at the same time. For example, adding pridopidine therapy to a patient already receiving donepezil therapy.

A dosage unit as used herein may comprise a single compound or mixtures of compounds thereof.

A dosage unit can be prepared for oral dosage forms, such as tablets, capsules, pills, powders, and granules.

Pharmaceutically Acceptable Salts

The active compounds for use according to the invention may be provided in any form suitable for the intended administration. Suitable forms include pharmaceutically (i.e. physiologically) acceptable salts, and pre- or prodrug forms of the compound of the invention.

In an embodiment, the pharmaceutically acceptable salt of pridopidine comprises the hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, salicylate, sorbate, stearate, succinate, tartrate or toluene-p-sulphonate salt.

In an embodiment, the pharmaceutically acceptable salt of pridopidine is pridopidine hydrochloride. In another embodiment, the pharmaceutically acceptable salt of pridopidine is pridopidine hydrobromide. In another embodiment, the pharmaceutically acceptable salt of pridopidine is pridopidine nitrate. In another embodiment, the pharmaceutically acceptable salt of pridopidine is pridopidine perchlorate. In another embodiment, the pharmaceutically acceptable salt of pridopidine is pridopidine phosphate. In another embodiment, the pharmaceutically acceptable salt of pridopidine is pridopidine sulphate. In another embodiment, the pharmaceutically acceptable salt of pridopidine is pridopidine formate. In another embodiment, the pharmaceutically acceptable salt of pridopidine is pridopidine acetate. In another embodiment, the pharmaceutically acceptable salt of pridopidine is pridopidine aconate. In another embodiment, the pharmaceutically acceptable salt of pridopidine is pridopidine ascorbate. In another embodiment, the pharmaceutically acceptable salt of pridopidine is pridopidine benzenesulphonate. In another embodiment, the pharmaceutically acceptable salt of pridopidine is pridopidine benzoate. In another embodiment, the pharmaceutically acceptable salt of pridopidine is pridopidine cinnamate. In another embodiment, the pharmaceutically acceptable salt of pridopidine is pridopidine citrate. In another embodiment, the pharmaceutically acceptable salt of pridopidine is pridopidine embonate. In another embodiment, the pharmaceutically acceptable salt of pridopidine is pridopidine enantate. In another embodiment, the pharmaceutically acceptable salt of pridopidine is pridopidine fumarate. In another embodiment, the pharmaceutically acceptable salt of pridopidine is pridopidine glutamate. In another embodiment, the pharmaceutically acceptable salt of pridopidine is pridopidine glycolate. In another embodiment, the pharmaceutically acceptable salt of pridopidine is pridopidine lactate. In another embodiment, the pharmaceutically acceptable salt of pridopidine is pridopidine maleate. In another embodiment, the pharmaceutically acceptable salt of pridopidine is pridopidine malonate. In another embodiment, the pharmaceutically acceptable salt of pridopidine is pridopidine mandelate. In another embodiment, the pharmaceutically acceptable salt of pridopidine is pridopidine methanesulphonate. In another embodiment, the pharmaceutically acceptable salt of pridopidine is pridopidine naphthalene-2-sulphonate. In another embodiment, the pharmaceutically acceptable salt of pridopidine is pridopidine phthalate. In another embodiment, the pharmaceutically acceptable salt of pridopidine is pridopidine salicylate. In another embodiment, the pharmaceutically acceptable salt of pridopidine is pridopidine sorbate. In another embodiment, the pharmaceutically acceptable salt of pridopidine is pridopidine stearate. In another embodiment, the pharmaceutically acceptable salt of pridopidine is pridopidine succinate. In another embodiment, the pharmaceutically acceptable salt of pridopidine is pridopidine tartrate. In another embodiment, the pharmaceutically acceptable salt of pridopidine is pridopidine toluene-p-sulphonate.

In an embodiment, the pharmaceutically acceptable salt of each of the analog compounds of pridopidine (Compound 1-8) comprises the hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, salicylate, sorbate, stearate, succinate, tartrate or toluene-p-sulphonate salt.

Such salts may be formed by procedures well known and described in the art.

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In an embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, in multiparticulate, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, PA).

It is understood that where a parameter range is provided, all integers within that range, and tenths thereof, are also provided by the invention. For example, "0.1 mg-40.0 mg" includes 0.1 mg, 0.2 mg, 0.3 mg, 0.4 mg, etc. up to 40.0 mg.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1: Pridopidine Attenuates the MK-801-induced Deficit of Working Memory in Y-maze Mice This Example examines the effect of pridopidine on the deficits of working memory and the increase in total arm entries induced by MK-801 in the mouse Y-maze.

Materials and Methods

Animals: Male ddY mice (Japan SLC Inc., Shizuoka, Japan) aged 5 weeks were used. The mice were maintained with free access to laboratory chow and water. The mice were placed in the experiment room at least 1 h before the experiment.

Drugs: Pridopidine hydrochloride was dissolved in water and administered orally. (+)-MK-801 hydrogen maleate (dizocilpine hydrogen maleate) (commercially available from Sigma-Aldrich (St. Louis, MO, USA)) was dissolved in saline and administered intraperitoneally. The drugs were administered at a volume of 10 mL/kg. The dose levels of pridopidine are presented as the amount of free base.

Y-maze: The Y-maze is a learning and memory test for rodents (van den Buuse 2005). Y-maze test is based on the innate curiosity of rodents to explore novel environments (Luszczki et al., 2005). It is used to assess exploratory behaviours, learning and memory function, short term memory, working memory, general locomotor activity, and stereotypic behavior in rodents (Hazim 2011, Onaolapo 2012, Detrait 2010).

Rodents exhibit a tendency to alternate between maze arms, thereby providing a measure of short term spatial memory. A high alternation rate is indicative of sustained cognition as the animals must remember which arm was entered last to not reenter it (Bryan 2009).

The Y-maze was made of gray vinyl chloride. Each arm was 40 cm long, 13 cm high, 3 cm wide at the bottom, and 10 cm wide at the top. All arms converged at equal angles.

Experimental Procedure: The present experiments were carried out according to the method established by Maurice et al. (1997). Pridopidine was administered, followed by MK-801 10 minutes later. Twenty minutes after administration of MK-801, each mouse was placed at the end of one arm and allowed to move freely through the maze during an 8-minute session. The series of arm entries were recorded. Alternation was defined as visits into all three arms on consecutive occasions. The number of maximum alternations was the total number of arm entries minus 2. The percentage of alternation was calculated as the number of alternations divided by maximum alternations and multiplied by 100.

Statistical Analysis: The percentage of alternation and total arm entries were expressed as the mean±SEM. The statistical significance between the normal group and the control group was calculated using the Student's t test. The statistical analysis for drug treatment versus the control group was conducted using Dunnett's multiple comparison test. The level of statistical significance was $p<0.05$.

Results

Figure 1B:
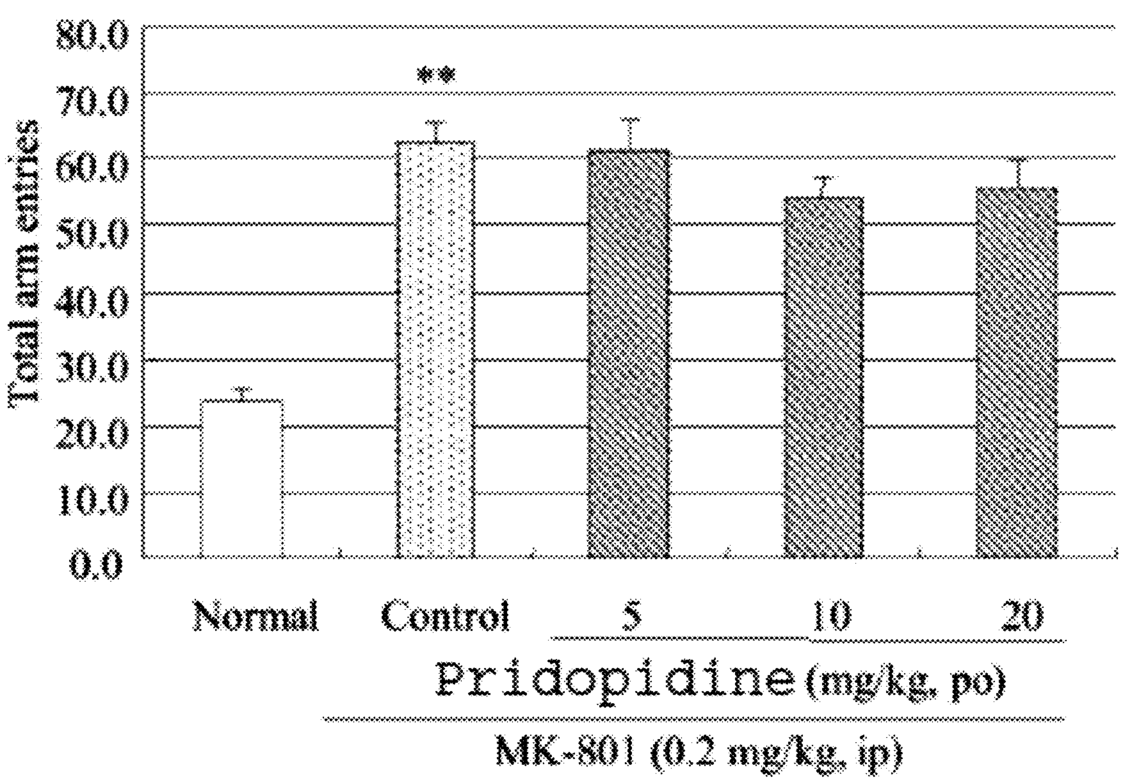
Figure 2:
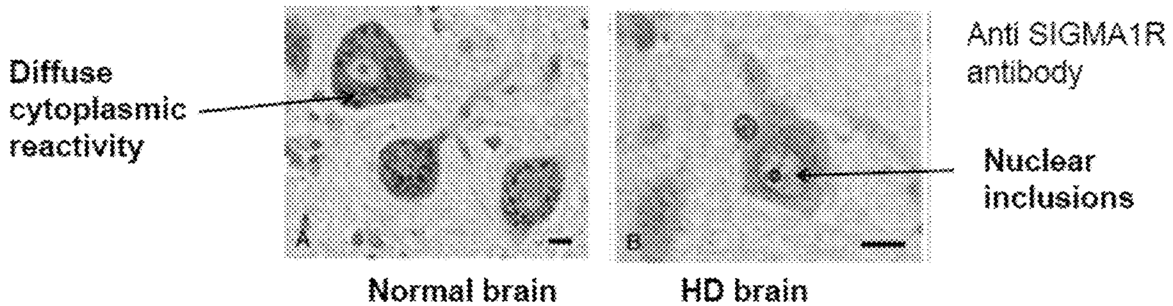
FIG. 2: Huntington's Disease S1R accumulates in neuronal nuclear inclusion (NNI).

Administration of MK-801 significantly ($P<0.01$, FIG. 1A, using the Student's t test) decreased the alternation percentage. Pridopidine restored the alternation percentage in the MK-801-treated mice with statistical significance at 10 and 20 mg/kg ($P<0.05$, FIG. 1A, by Dunnett's multiple comparison test). The total number of arm entries was significantly ($P<0.01$, FIG. 1B, using Student's t test) augmented by treatment with MK-801. Pridopidine showed no statistically significant change in the MK-801-induced increase in the total number of arm entries (FIG. 1B).

DISCUSSION

In the Y-maze, the non-competitive NMDA antagonist, MK-801 (dizocilpine), impairs spontaneous alternation behavior, which reflects working memory, and enhances the total number of arm entries, which represents locomotor activity (Parada-Turska and Turski, 1990).

Example 1 demonstrates the anti-amnesic effects of pridopidine on working memory impairment related to the NMDA receptor blockade. Pridopidine attenuated the MK-801-induced decrease in percent alternation with statistical significance at 10 and 20 mg/kg. These results demonstrate that pridopidine improves cognitive status and improves cognitive impairment (such as working memory) in patients, including patients with cognitive deficits.

Nilsson 2004 showed that pridopidine counteracted the behavioral primitivization induced by MK-801 in mice. However, the experiments completed in Nilsson 2004 are different from the experiment described in Example 1. Specifically, the experiments completed in Nilsson 2004 did not show that pridopidine can improve cognitive function or memory loss.

Example 1 uses a Y-maze which, as described above, is a commonly used experiment to measure cognitive and memory function. In the Y-maze experiment, the ability of the rodent to use its cognitive function to remember which arm of the Y-maze it traveled to previously is tested when measuring percentage of alternation. In comparison, the experiment in Nilsson 2004 (and further described in Nilsson 2001) does not contain such a memory component. The experiment in Nilsson 2004 placed rodents in a rectangle shaped arena and used a camera to measure the movements and behavior of the mice. The specific behaviors measured were forward locomotion, rearing with exploratory sniffing, grooming and digging. In Nilsson 2004 and Nilsson 2001 treating mice with MK-801 prior to the experiment causes mice that naturally alternate between the specific measured behaviors to mostly perform monotonous forward locomotion (Nilsson 2001). What Nilsson 2004 found was that pridopidine counteracted such effects of MK-801 on mice. However, there is no clear relationship between the measured behaviors and cognitive function in the experiment of Nilsson 2004. Thus, the experiments shown in Nilsson 2004 cannot show that pridopidine enhances cognitive function. This is likely why the authors of Nilsson 2004 state that additional tests are necessary to determine if pridopidine can enhance cognitive function.

Example 2

Alteration in the density of spines and abnormalities in the size and shape of spines was observed in the brains of HD patients (Graveland 1985).

Figure 3:
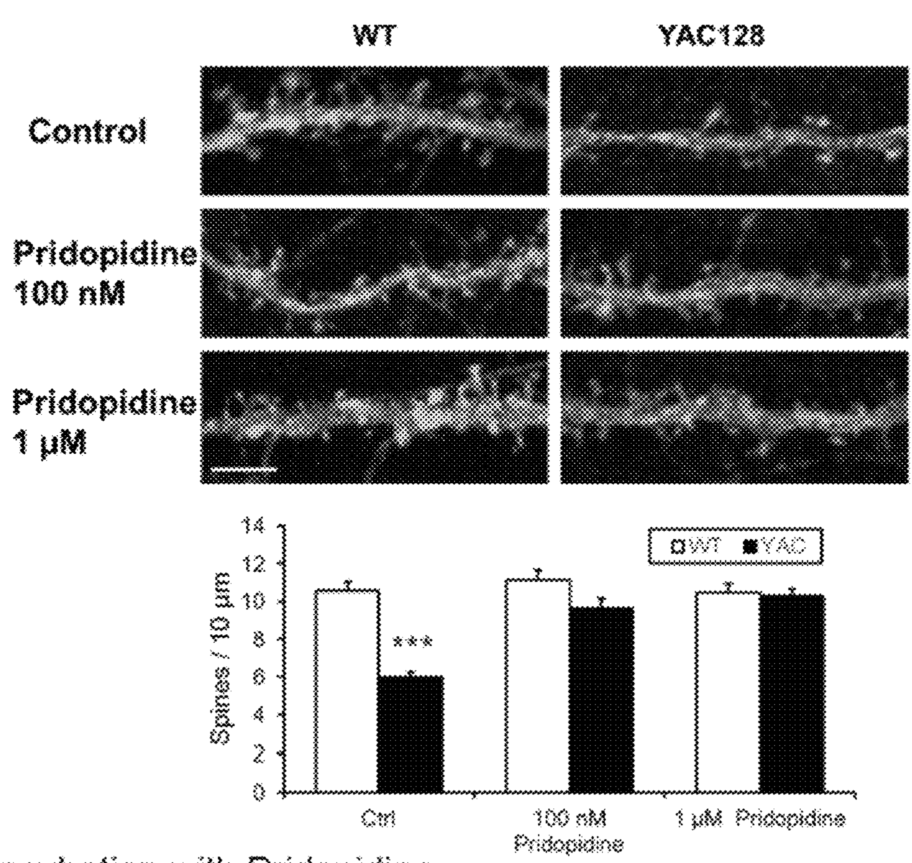
FIG. 3: Pridopidine rescues spine loss in YAC128 corticostriatal co-cultures.
Figure 4:
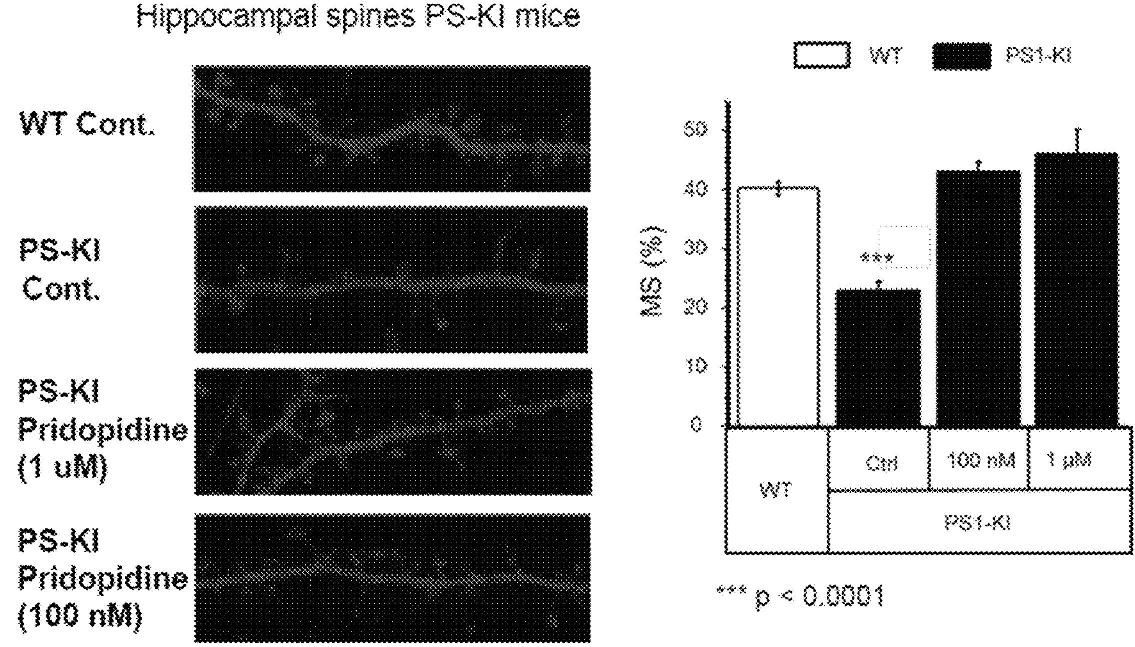
FIG. 4: Pridopidine rescues mushroom spine loss in PS-KI (AD) neurons.

FIG. 3 shows that pridopidine rescues spine loss in YAC128 corticostriatal co-cultures. FIG. 4 shows that pridopidine rescues mushroom spine loss in PS-KI (AD) neurons.

Dendritic spines are important in maintaining cognition and motor functions. Dendritic spine formation is critical for the establishment of excitatory synaptic networks. Spines show structural plasticity as the basis for the physiological changes in synaptic efficacy that underlie learning and memory. Motor control is regulated by cortical-medium spiny neurons synaptic connections. The spines are the basis for these connections (Kreitzer 2008 and Bourne 2008).

Example 3: Acetylcholine and Pridopidine

Animals: Eighteen adult male Sprague Dawley rats (Harlan, USA) were used. Before the experiment, rats were group housed in plastic cages (3-4 animals/cage) and had access to food and water ad libitum. Animals were kept on a 12/12 hour light/dark cycle. Experiments were conducted in accordance with the protocols approved by the Institutional Animal Care and Use Committee of Brains On-Line, LLC.

Microdialysis Experiment: Microdialyis experiments were performed one day after surgery. On the day of the experiment, the probes were connected with flexible PEEK tubing to a microperfusion pump (Harvard PHD 2000 Syringe pump, Holliston, MA or similar). Microdialysis probes were perfused with aCSF containing 147 mM NaCl, 3.0 mM KCl, 1.2 mM CaCl2 and 1.2 mM MgCl2, at a flow rate of 1.5 μL/min. Microdialysis samples were collected in 30 minute periods by an automated fraction collector (820 Microsampler, Univentor, Malta) into 300 μL polystryene mini-vials already containing 15 μL 0.02 M formic acid (FA) and 0.04% ascorbic acid in ultrapurified $H_2O$. Four basal samples were collected before pridopidine (15 or 60 mg/kg, PO) or vehicle was administered. Samples were collected.

Results: Acetylcholine (Ach) levels in dialysate

Figure 5:
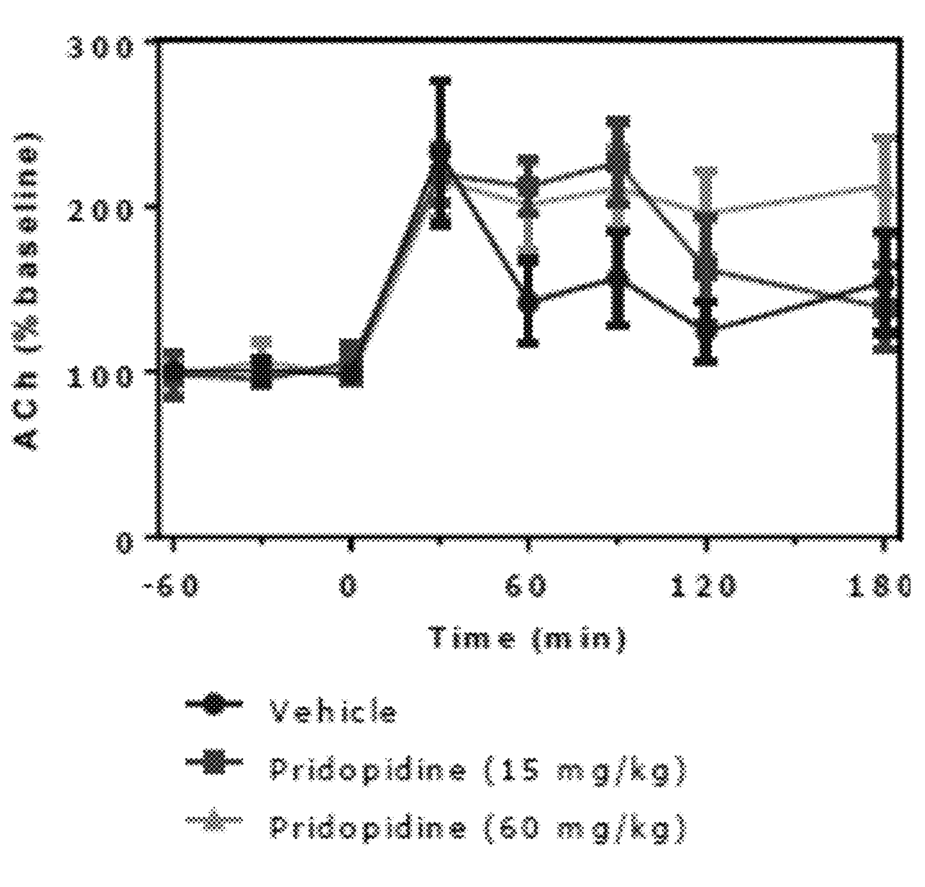
FIG. 5: Effect of pridopidine (15 and 60 mg/kg) on Acetylcholine (Ach) levels in the PFC of rats (data expressed as mean % baseline±SEM).
Figure 6:
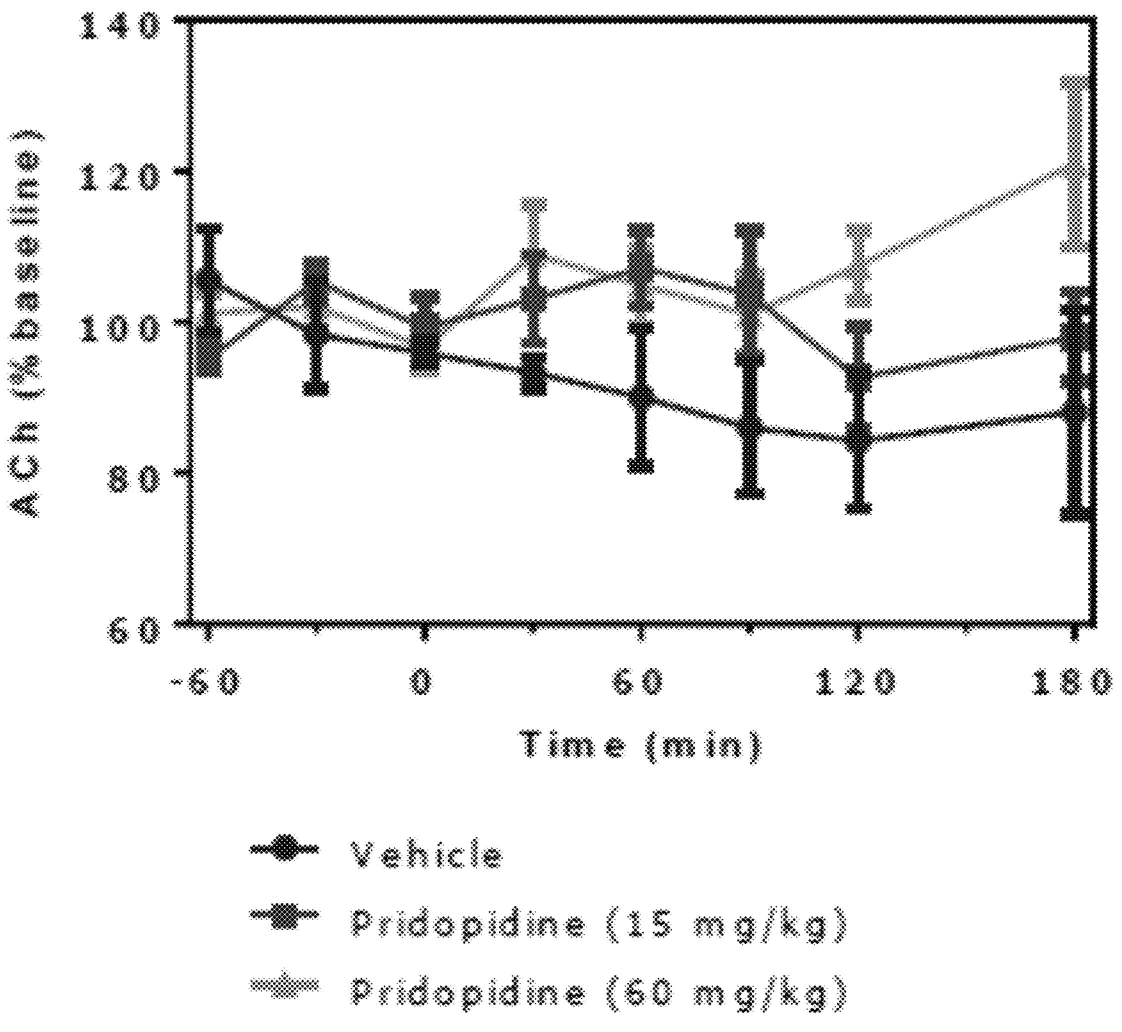
FIG. 6: Effect of Pridopidine (15 and 60 mg/kg) on ACh levels in the STR of rats (data expressed as mean % baseline±SEM).
Figure 7:
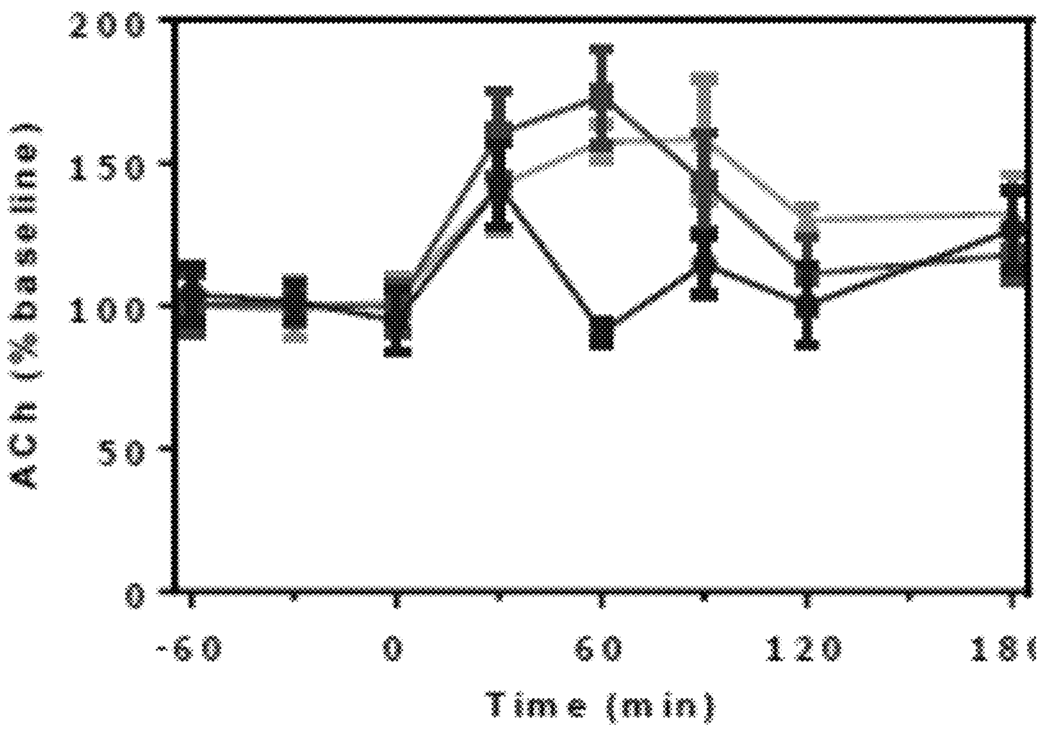
FIG. 7: Effect of pridopidine (15 and 60 mg/kg) on ACh levels in the Hipp of rats (data expressed as mean % baseline±SEM).

FIGS. 5, 6, and 7 show the levels of ACh in the prefrontal cortex (PFC), striatum (STR), and hippocampus (Hipp), respectively. Treatment with pridopidine resulted in significant increases in Ach in the prefrontal cortex following 15 mg/kg administration at 30 min after administration (219% change from baseline; $p<0.05$), at 60 min after administration (226% change from baseline; $p<0.05$) and at 90 min after administration (226% change from baseline; $p<0.05$), and following 60 mg/kg administration at 30 min after administration (215% change from baseline; $p<0.05$), at 60 min after administration (201% change from baseline; $p<0.05$), at 90 min after administration (211% change from baseline; $p<0.05$) and at 180 min after administration (212% change from baseline; $p<0.05$). Treatment with pridopidine resulted in significant increases in Ach in the hippocampus following 15 mg/kg administration at 30 min after administration (160% change from baseline; $p<0.05$) and at 60 min after administration (173% change from baseline; $p<0.05$), and following 60 mg/kg administration at 60 min after administration (157% change from baseline; $p<0.05$) and at 90 min after administration (158% change from baseline; $p<0.05$) Tables 1 and 2 present the Maximum % Change from baseline in Ach levels after 15 and 60 mg/kg administration, respectively.

TABLE 1

| Acetylcholine levels in dialysate (% Change from baseline. Single dose 15 mg/kg p.o) | | | |
|---|---|---|---|
| | Striatum | Prefrontal cortex | Hippocampus |
| Acetylcholine | 107 | 226* | 173* |

*statistically significant ($p < 0.05$)

TABLE 2

| Acetylcholine levels in dialysate (% Change from baseline. Single dose 60 mg/kg p.o) | | | |
|---|---|---|---|
| | Striatum | Prefrontal cortex | Hippocampus |
| Acetylcholine | 120 | 215* | 158* |

*statistically significant ($p < 0.05$)

Acetylcholine is an important neurotransmitter in the nervous system and is necessary for learning and memory function (Winkler 1995). Acetylcholine has been accorded an important role in supporting learning and memory processes in the hippocampus. Cholinergic activity in the hippocampus and prefrontal cortex is correlated with memory (Hironaka 2001). Additionally, restoration of ACh in the hippocampus after disruption of the septohippocampal pathway is sufficient to rescue memory (Parent 2004).

Example 4: Effect of Pridopidine in a Model of AD: Injury of Rat Primary Cortical Neurons by Human Amyloid Beta 1-42

AD is characterized by the progressive accumulation of intracellular neurofibrillary tangles, extracellular parenchymal senile plaques, and cerebrovascular deposits comprised of amyloid-β 1-42 peptides (Sakono et al, 2010).

A β peptide is a proteolytic product derived through sequential proteolysis of amyloid precursor protein (APP), which occurs as a result of cleavage by β-secretase and γ-secretase. Mutations at the cleavage sites in APP increase the production of A β oligomers. The progressive accumulation of AP in the form of senile plaques, which is one of the pathologic hallmarks of AD, had been recognized as one of the major causes of AD pathology (Kawahara and Kuroda, 2000) by triggering neurotoxicity, oxidative damage, and inflammation (Pike et al., 1991; Cummings et al., 1998; Combs et al., 2000). The most abundant AP peptide form found in AD brain senile plaques are the 40 and 42 amino acid forms (Sisodia et al., 1990).

However, the number of senile plaques in a particular region of the AD brain correlates poorly with the local extent of neuron death or synaptic loss, or with cognitive impairment. Recent studies show a robust correlation between the soluble Aβ oligomer (AβO) levels and the extent of synaptic loss and severity of cognitive impairment (for review see Sakono et al., 2010).

The study investigated the neuroprotective effect of pridopidine on cortical neurons incubated for 24 hours in the presence of AβO, an in vitro model of AD (Callizot et al., 2013). BDNF at 50 ng/ml was used as a positive control in this study.

EXPERIMENTAL PROTOCOL

Cortical Neurons Cell Culture

Rat cortical neurons were cultured as follows. Pregnant female rats of 15 days gestation were killed by cervical dislocation (Rats Wistar; Janvier Lab) and the fetuses were removed from the uterus. The cortexes were removed and placed in ice-cold medium of Leibovitz (L15, Panbiotech, ref: PO4-27055) containing 2% of Penicillin 10.000 U/ml and Streptomycin 10 mg/ml (PS, Panbiotech, ref: P06-07100) and 1% of Bovine Serum Albumin (BSA, Panbiotech, Ref: P06-1391100). Cortexes were dissociated by trypsin-EDTA (Panbiotech, Ref: P10-023100) for 20 min at 37° C. The reaction was stopped by the addition of Dulbecco's modified Eagle's Medium (DMEM, Panbiotech, Ref PO4-03600) containing DNase 1 grade II (0.1 mg/ml, Panbiotech, ref: P60-37780100) and 10% of Foetal Calf Serum (FCS, Invitrogen, ref: 10270-098). Cells were then mechanically dissociated by 3 serial passages through a 10 ml pipette. Cells were then centrifuged at 515×g for 10 min at 4° C. The supernatant was discarded and the pellet of cells was re-suspended in a defined culture medium consisting of Neurobasal (Nb, Invitrogen, ref: 21103) supplemented with B27 (2%, Invitrogen, ref: 17504), L-glutamine (2 mM, Panbiotech, ref: PO4-80100), 2% of PS solution and 10 ng/ml of of Brain-derived neurotrophic factor (BDNF, PanBiotech, Ref: CB-1115002). Viable cells were counted in a Neubauer cytometer using the trypan blue exclusion test. The cells were seeded at a density of 30,000 cells/well in 96 well-plates pre-coated with poly-L-lysine and were cultured at +37° C. in a humidified air (95%)/$CO_2$ (5%) atmosphere. After 11 days of culture, cortical neurons were intoxicated with human AP 1-42 at 10 μM for 24 hrs. One culture was performed per condition, 6 wells per condition.

Pridopidine and Human β Amyloid 1-42 Treatment

The human β amyloid 1-42 peptide preparation was done following an internal and original procedure validated by Neuron experts (Callizot et al., 2013). Briefly, on day 12 of culture, the supernatant was removed and fresh medium was added, with human amyloid β 1-42 (10 μM) and with pridopidine.

The following conditions were included:

a) Medium without Human β amyloid 1-42 (control) for 24 h
b) Human β amyloid 1-42 (10 μM) for 24 h
c) Human β amyloid 1-42 (10 μM) for 24 h with pridopidine (200, 50, 10, 1, 0.1 and 0.01 μM)
d) Human β amyloid 1-42 (10 μM) for 24 h with BDNF (50 ng/ml)

End Point Evaluation: Measure of Total Number of MAP 2 Neurons.

Neurons that survived after 24 h incubation were stained with MAP 2.

After 24 hours, cells were washed twice in Phosphate Buffered Saline (PBS, PanBiotech, ref: PO4-36500) and then fixed by a cold solution of ethanol (95%, Sigma, ref: 32221) and acetic acid (5%, Sigma, ref: 33209) for 5 min. The cells were then permeabilized and non-specific sites were blocked with a solution of PBS containing 0.1% of saponin (Sigma Aldrich, ref: 57900) and 1% FCS for 15 min at room temperature. Then, cells were incubated for 2 hours with mouse monoclonal primary Microtubule-associated protein 2 antibody (MAP-2, Sigma M4403) for 2 hours in the same solution at the dilution of 1/400. This antibody was revealed with Alexa Fluor 488 goat anti-mouse (Molecular probe, ref: A11001) for 1 hour in the same solution. Nuclei of cells were labelled by a fluorescent marker (Hoechst solution, SIGMA, ref: B1155).

For each condition, 20 pictures per well were taken using InCell Analyzer™ 2000 (GE Healthcare) with 20× magnification. All images were taken under the same conditions.

Statistics

The data were expressed as mean±s.e.mean (of 6 or 12 data per condition). A global analysis of the data was performed using a one-way analysis of variance (ANOVA). *$p<0.05$; $p<0.01$; *$p<0.005$.

Figure 8:
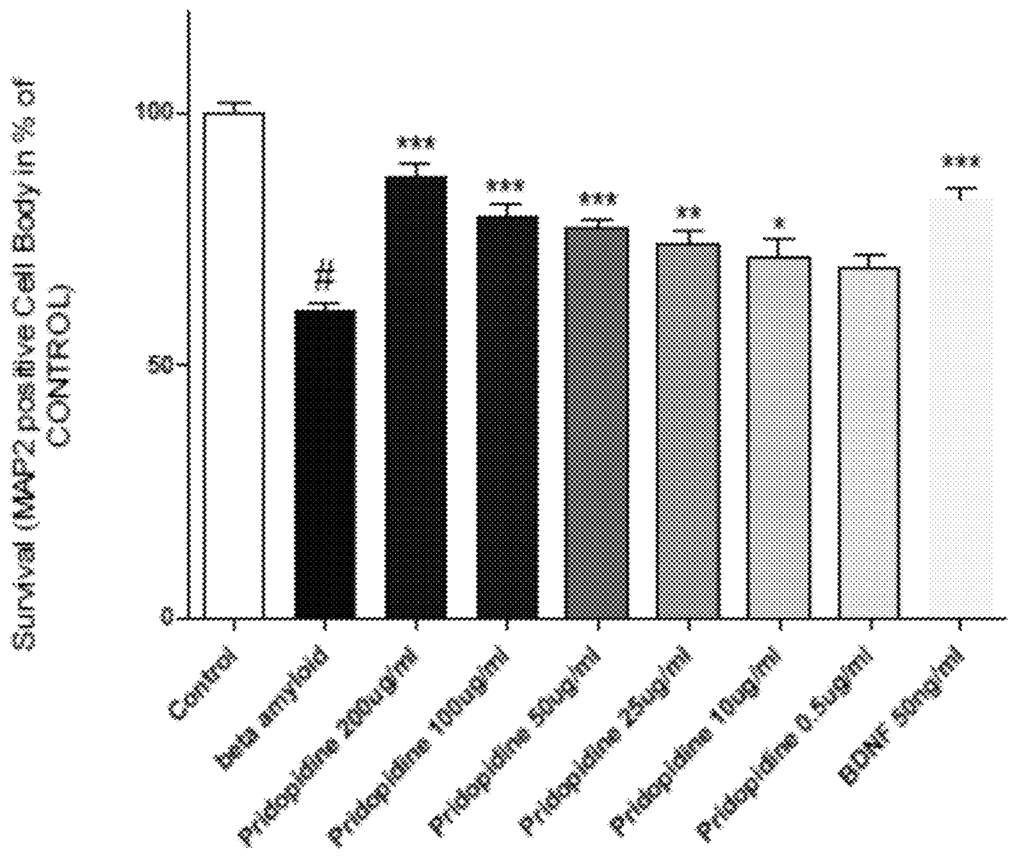
FIG. 8: Effect of pridopidine (6 concentrations) and BDNF (50 ng/ml) on survival of primary neuron cultured in the presence of β amyloid 1-42 (10 μM), expressed in percentage of control (mean±s.e.m; * $p<0.05$; $p<0.01$; * $p<0.005$; β amyloid 1-42 vs pridopidine/BDNF; one way Anova followed by Dunnett's test).

Results

β amyloid 1-42 injury applied at 10 μM for 24 h induced a large and significant decrease (−40%, $p<0.005$) in MAP 2 positive cells (FIG. 8).

Application of reference compound BDNF (50 ng/ml) inhibited cell death resulting from β amyloid 1-42 injury. These results validate the study.

Pridopidine reduced the toxic effect of β amyloid 1-42 in a dose dependent manner. The proportion of neuron survival was 87% of the medium control when incubated with pridopidine at 200 μg/ml ($p<0.005$). At 100, 50, 25 and 10 μg/ml pridopidine increased significantly neuron survival resulting from β amyloid 1-42 injury (79%, $p<0.005$; 77% $p<0.005$; 74% $p<0.01$ and 71%, $p<0.05$, respectively).

CONCLUSIONS

Pridopidine increased neuron survival resulting from β amyloid 1-42 injury significantly and with a dose dependent manner.

Figure 9:
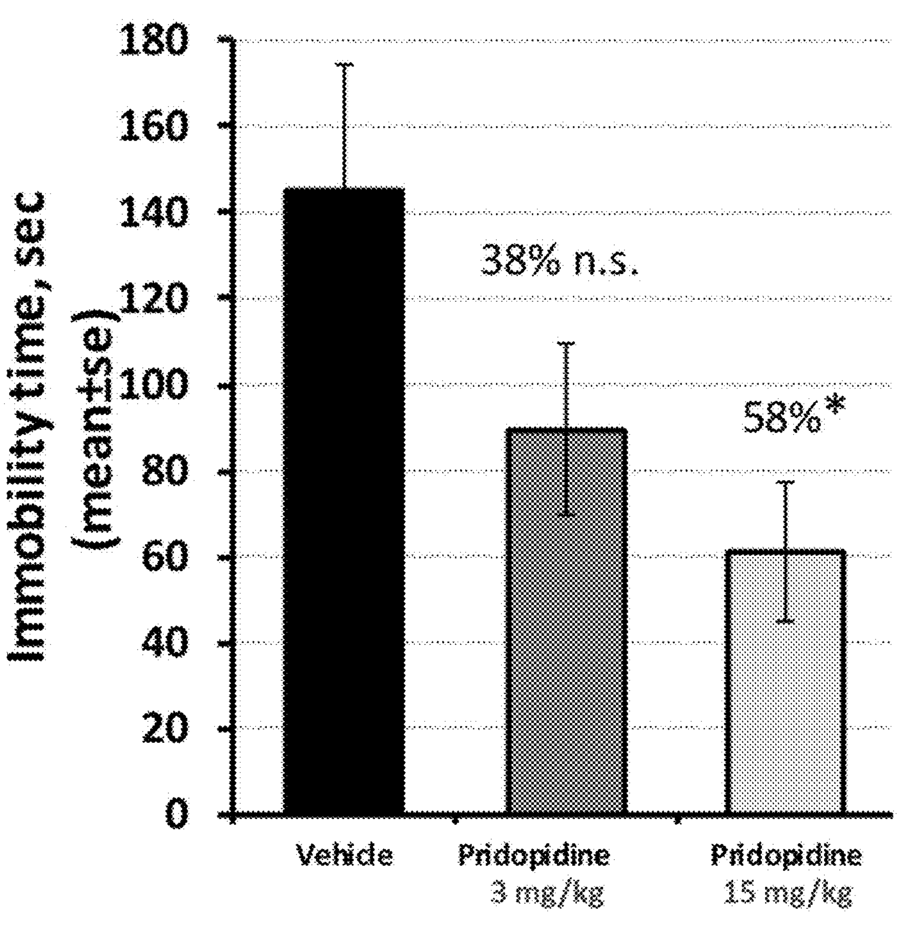
FIG. 9: Anti-depressant effect of pridopidine on depressive-like behavior in rats. Rats were treated with either vehicle, 3 mg/kg or 15 mg/kg of pridopidine by oral gavage for 7 days, then placed in individual cylinders filled with room-temperature water 15 cm deep for 6 minutes. Sessions were recorded by a video camera and analyzed blindly. At 3 mg/kg, pridopidine shows a positive effect towards reducing primary depression (38% reduction in immobility time vs vehicle). The 15 mg/kg dose shows a stronger and significant anti-depressive-like effect in the FST, reaching 58% reduction in immobility time N=10, *$p<0.05$. Pridopidine decreases immobility time in WT rats. N=10, *$p<0.05$

Example 5: Anti-Depressive Effect in the Rat Forced Swim Test Using Pridopidine (FIG. 9)

Sprague-Dawley male rats, 6 weeks old were used. Rats were pre-tested on day 1 to ensure stable and high duration of immobility during the 5-min test session. Rats were then treated daily with pridopidine at 3 or 15 mg/kg by oral gavage for 7 days. On day 8, rats were administered the FST 30 minutes after pridopidine administration. Pridopidine decreased immobility time in rats by 38% and 58% in the 3 and 15 mg/kg groups, respectively (FIG. 9). This indicates an anti-depressive effect of pridopidine in rats. This example demonstrates that pridopidine is a promising therapeutic target for depressive behavior.

Figure 10:
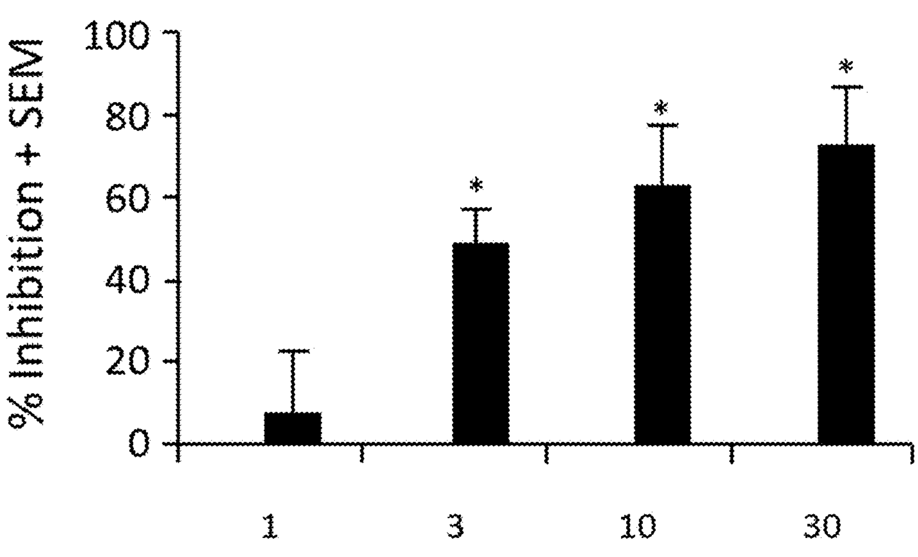
FIG. 10: Anxiolytic effect of pridopidine in the marble burying test in mice (NS). Object burying is indicative of anxiety in rodents. Inhibition of object-burying in rodents is an accepted model for measuring anxiolytic effects of a drug (Broekkamp et al, 1986; Treit, 1985; Treit et al, 1981). Marble burying activity was assessed in male NMRI mice, which were then treated with pridopidine 1, 3, 10 or 30 mg/kg for 30 minutes before being tested again for marble burying. Pridopidine shows a dose-dependent inhibition of marble burying, indicating an anxiolytic effect. Marble burying also represents an animal model for Obsessive-compulsive disorder. Data shown are mean percent of inhibition±SEM, *$p<0.05$ ANOVA.

Example 6: Pridopidine Shows an Anxiolytic Effect in the Marble Burying Test in Mice (NS) (FIG. 10)

Inhibition of object-burying in rodents is proposed as an animal model of anxiety because anxiolytic drugs reduce duration and extent of burying (Broekkamp et al, 1986; Treit, 1985; Treit et al, 1981).

Materials and Methods

Animals

Male NMRI mice (20-36 g body weight) were housed in groups of five in a temperature (20±2° C.) and humidity (50-60%) controlled colony room under a non-reversed 12 (6-18 on)/12 h light-dark cycle with food and water ad libitum except during the actual experiments. 8 mice were used for each drug dose and 16 mice for the vehicle-treated control group. Animals were assigned according to the experimental plan to one of the 4 test boxes run simultaneously.

Procedure 30 min after drug application (pridopidine), mice were individually placed for 30 min in an open box (L 44 cm, W 43 cm, H 52 cm) filled with 5 cm of sawdust bedding material. 25 clean glass marbles (2 cm in diameter) were evenly spaced on the sawdust. The number of marbles covered by sawdust were counted. The experimenter also observed the animals for obvious inhibition of general activity (locomotor activity). Experiments were done between 8:30 and 12.00 a.m.

Drugs

Pridopidine was suspended in 5% gum Arabic for p.o. application (application volume 1 ml/kg bodyweight).

Results

Pridopidine treatment resulted in inhibition of marble-burying at all doses tested, in a dose-dependent manner (FIG. 10). 1 mg/kg demonstrated 8% inhibition; 3 mg/kg demonstrated 49% inhibition; 10 mg/kg demonstrated 62% inhibition; and 30 mg/kg demonstrated 73% inhibition (FIG. 10).

Marble burying also represent an animal model for Obsessive-compulsive disorder.

Figure 11:
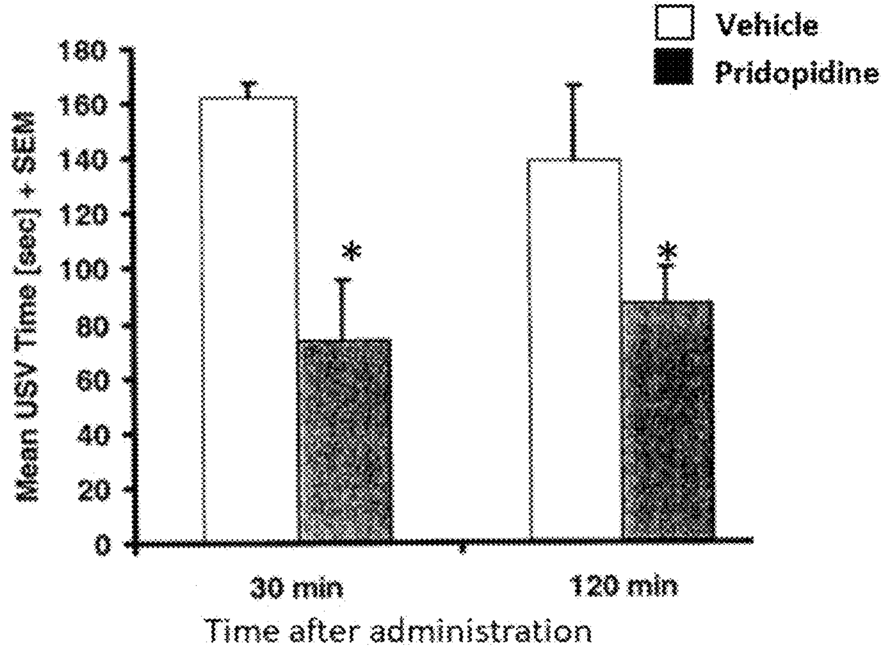
FIG. 11: Anxiolytic effects of pridopidine in the rat ultrasonic vocalization (USV). USVs are considered a measure of anxiety in rodents. Young adult rats were treated with 30 mg/kg pridopidine by oral gavage. Rats were first primed by a series of up to 10 electric shocks delivered to the feet by a grid in the floor, which was terminated in case of 3 consecutive and consistent USVs. The next day, each rat received 5 initial shocks, and USVs were recorded in the following 3-minute period. Animals were tested 30 and 120 minutes after pridopidine administration. Pridopidine significantly inhibited USV duration in rats. Data shown are mean USV time (sec)±SEM, N=4 rats per treatment group, *$p<0.05$.

Example 7: Pridopidine Shows Anxiolytic Effects in the Rat Ultrasonic Vocalization (USV) Test (FIG. 11)

The ultrasonic vocalization (USV) test in young adult rats is one of the most robust animal models of anxiety amongst the various animal models used to detect anxiolytic-like effects in animals.

Materials and Methods

Animals

Male Sprague-Dawley rats (270-400 g bodyweight) were housed in groups of two in a temperature (20±2° C.) and humidity (50-60%) controlled colony room under a non-reversed 12 (6-18 on)/12 h light-dark cycle with food and water ad libitum except during the actual experiments. 4 rats were used for each drug dose and the vehicle-treated control group.

Procedure

As described elsewhere (Bartoszyk G D (1998) Life Sci 22: 649-663; and Bartoszyk G D, (1997) Eur J Pharmacol 322: 147-153) USV was measured in a sound-attenuated test chamber (W 24 cm, L 22 cm, H 22 cm) with a grid floor for delivery of foot-shock (scrambled shock of 0.2 mA for 0.5 s). USV was recorded by a microphone and processed by an interface to select USV signals and to digitize the resulting signals for automatic processing. In the priming phase, each rat was placed in the test chamber. After a 2 min time period, a series of at most ten shocks (trials), 1.8 mA for 0.3 s, separated by 20 s shock-free intervals, was delivered via the grid floor of the test chamber. In the shock-free intervals the occurrence of ultrasonic vocalization (22±5 kHz) was automatically recorded, and the duration of ultrasonic vocalization was calculated immediately. The priming session was terminated either when the rat constantly vocalized at least for 10 s on three consecutive trials or after the tenth trial. Rats not responding with USV on three consecutive trials were excluded from the test. In the actual test performed on the next day, each rat received 5 initial shocks (1.8 mA for 0.3 s, separated by 20 s shock-free intervals) in the test chamber, and the duration of USV (22+4 kHz) was recorded during the following 3 min period. Animals were repeatedly tested 30 and 120 min after pridopidine administration.

Drugs

Pridopidine was suspended in gum Arabic for p.o. application (application volume 10 ml/kg bodyweight).

Results

Following oral administration, pridopidine 30 mg/kg significantly inhibited USV in young adult rats 30 min and 120 min after administration (FIG. 11).

Example 8: Pridopidine is Effective in Rodent Models of Anxiety

Pridopidine is administered periodically (e.g., daily or twice daily) to rodents exhibiting symptoms of anxiety. Examples of rodent models include the HAB rats, selected on the basis of their behavior in the elevated plus maze (EPM); the Syracuse High and Low Avoidance rats; the Maudsley reactive/nonreactive strains; the Tsukuba High and Low Emotional rats, and the Floripa H and L lines a rat model of anxiety and depression. The Roman Low-Avoidance (RLA) rats, selected on the basis of poor acquisition of a two-way avoidance response in the shuttle box, are considered as a model of high trait anxiety-emotionality. Selective breeding of rats and mice improves the probability of discovering anxiety-related neurobiological correlates, including genetic determinants, and allows the study of gene-environment interactions. (Steimer 2011).

Administering pridopidine is effective in treating anxiety. Administering pridopidine is effective in reducing symptoms of anxiety.

Figure 12:
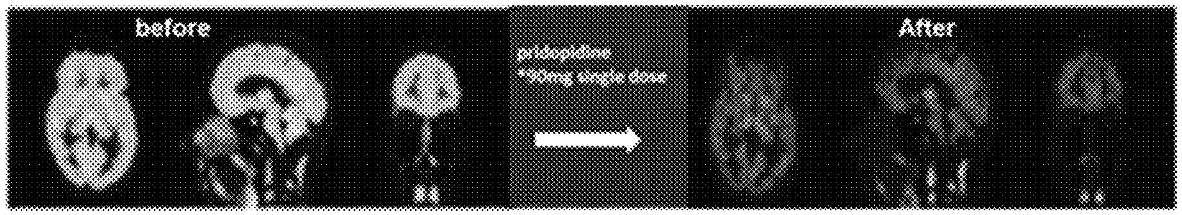
FIG. 12: Pridopidine low dose shows full S1R occupancy in a Human PET Study and complete 18F-Fluspidine displacement after single oral dose of 90 mg pridopidine.

Example 9: Pridopidine Selectively Occupies the S1R in Humans at Low Dose (FIG. 12)

Receptor Occupancy (RO) of pridopidine to the S1R and D2R was evaluated using Positron Emission Tomography (PET) imaging in the human brain (healthy volunteers and HD patients). The radio ligand (S)-(−)-[18F]fluspidine was used to image S1Rs, and the radio ligand [18F]fallypride was used to image D2Rs. The results of the imaging analysis show that at a plasma exposure correlating to the 45 mg bid dose steady state (ss) exposure, (90 mg single dose), pridopidine fully occupies the S1R (>90%) (FIG. 12).

Example 10: Pridopidine Increases Functional Capacity within the Default Mode Network (DMN)

Figure 13:
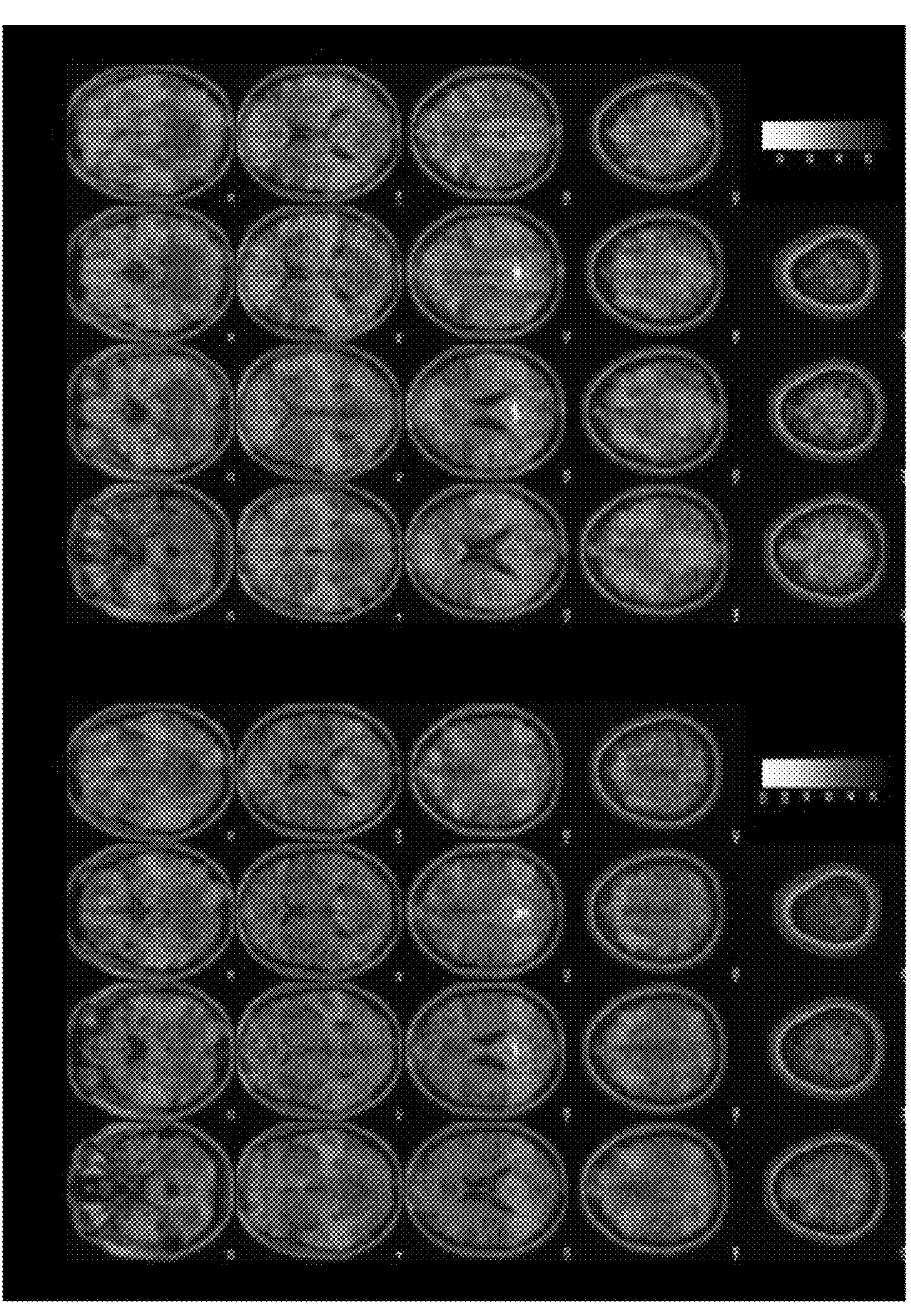
FIG. 13: The functional connectivity within the DMN with/without 90 mg pridopidine in HV (correlates with exposure at 45 mg bid at steady state). Upper panel: four individuals after 90 mg single dose pridopidine (post). Lower panel four individuals without pridopidine treatment (pre).
Figure 14:
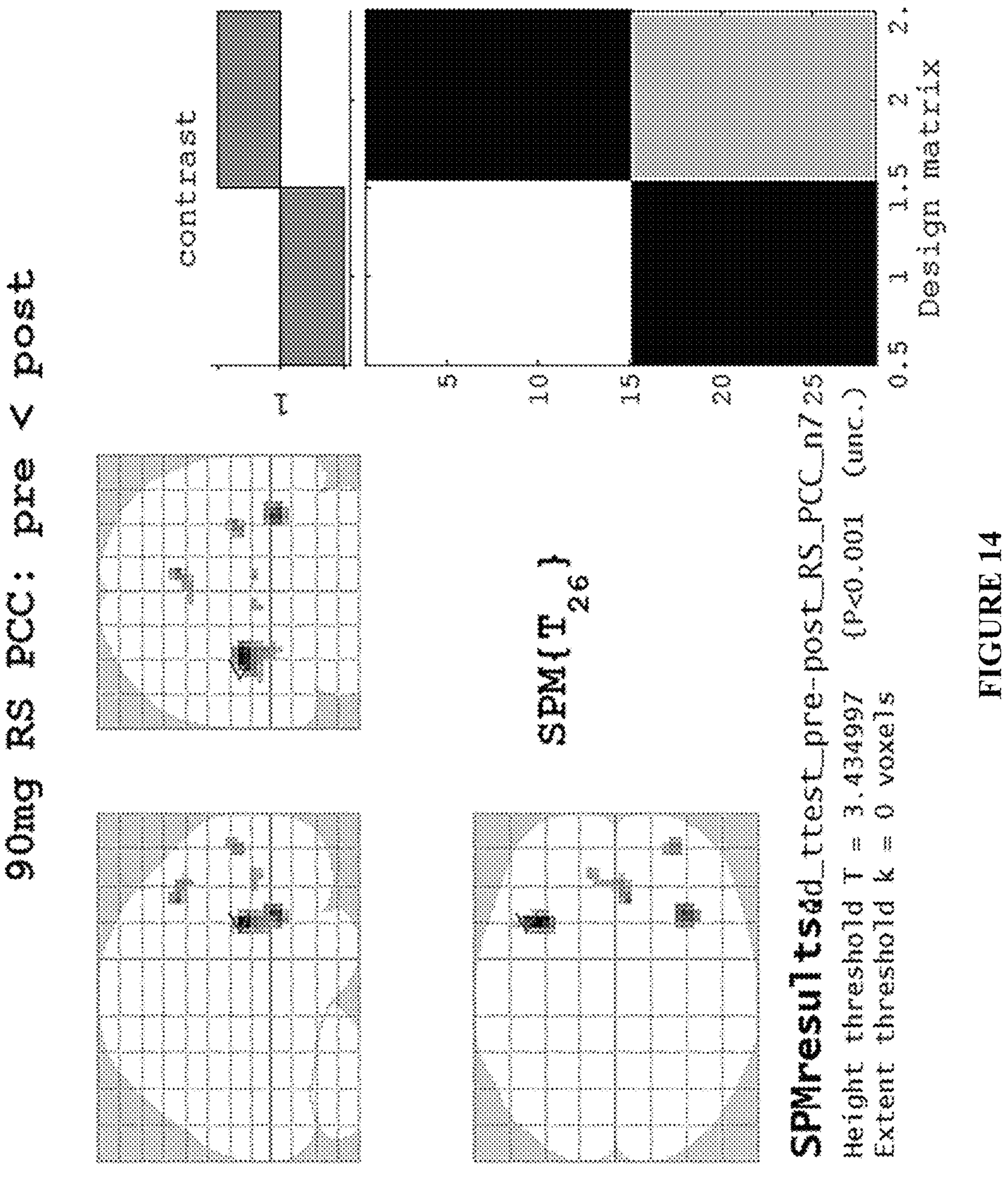
FIG. 14: SPM-based voxelwise group comparison (within the DMN) in HV before (pre) and after (post) 90 mg pridopidine (correlates with exposure at 45 mg bid at steady state) reveals pridopidine increased FC in the insula.
Figure 15:
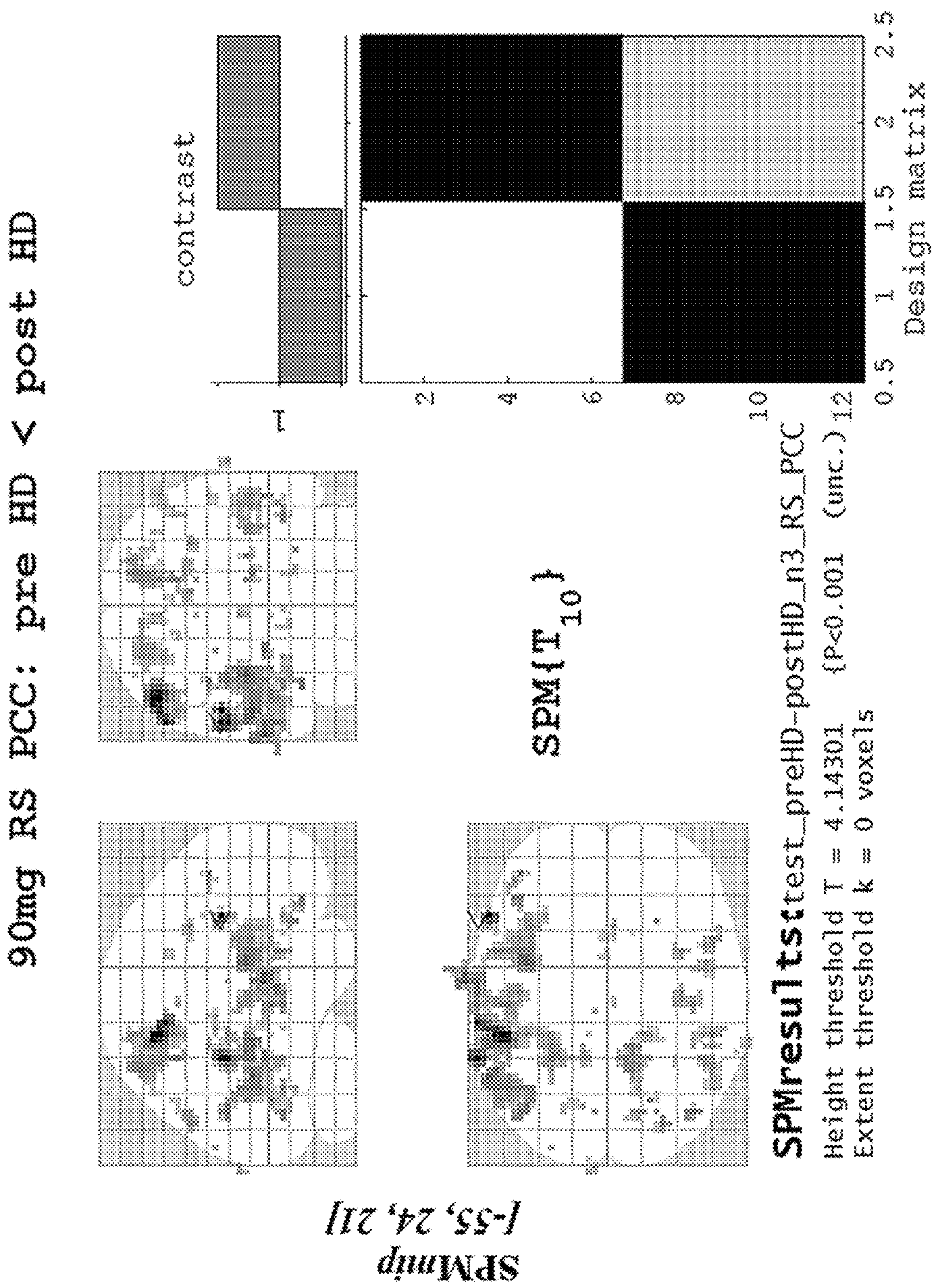
FIG. 15: SPM-based voxel wise group comparison (within the DMN) in HD patients before (pre) and after (post) 90 mg pridopidine (correlates with exposure at 45 mg bid at steady state) reveals pridopidine increased FC in the parietal and temporal cortex as well as precuneus and insula.

Correlation between S1R/D2R occupancy and brain network activity was evaluated using the functional resting-state MRI (rs-fMRI). Functional connectivity (FC) was calculated from rs-fMRI data sets. Pridopidine low dose (correlating to ss plasma exposure at 45 mg bid dose), shown by PET to selectively occupy only the S1R (no D2R binding), led to an increase in the DMN connectivity (increased activity) in healthy volunteers and in HD patients, as demonstrated in FIGS. 13-15. FIG. 13 shows pridopidine increases FC within the DMN in healthy volunteers (HVs). This visual inspection result is supported by the results of the SPM-based voxelwise group comparison: FIG. 14: SPM-based voxelwise group comparison (within the DMN) in HV before (pre) and after (post) 90 mg pridopidine reveals pridopidine increased FC in the insula. FIG. 15: SPM-based voxelwise group comparison (within the DMN) in HD patients before (pre) and after (post) 90 mg pridopidine reveals pridopidine increased FC in the parietal and temporal cortex as well as precuneus and insula.

Pridopidine showed an unexpected increase in DMN at low dose which selectively occupies the S1R.

Example 11: Pridopidine Reduces Anxiety and Depression in Parkinson's Disease Patients In an open label trial, seven patients with Parkinson's Disease received escalating doses (up to 100 mg/day) of pridopidine for two weeks. Depression and anxiety were assessed at baseline and week 2 using the Hamilton Depression (Ham-D) scale. The Ham-D scale is the most widely used clinician-administered depression assessment scale. It evaluates 17 items pertaining to symptoms of depression and anxiety. Higher values indicate more severe depression and anxiety. Ham-D scores 0-7 are considered normal, 8-13 mildly anxious or depressed, 14-18 moderate anxiety and depression, 19-22 severe anxiety and depression and >22 very severe (Hamilton; A rating scale for depression. J Neurol Neurosurg Psychiatry 1960; 23:56-62). At baseline, the average Ham-D score was 11.0±5.2, indicating patients were mildly anxious or depressed (Ham-D score >8 indicates anxiety and depression). After 2 weeks of treatment with pridopidine, the Ham-D score decreased to 4.4±3.9 (A from baseline −6.6 units, negative change indicates improvement, $p<0.05$). Thus, pridopidine significantly improves depression and anxiety in Parkinson's Disease (Source: Internal report ACR16IC005).

Example 12: Assessment of Efficacy of Pridopidine in Treating Patients Suffering from Anxiety or Depression Pridopidine is administered periodically (e.g., daily or twice daily) to a patient diagnosed with anxiety or depression. The patient is exhibiting symptoms of anxiety or depression. The pridopidine is administered intravenously or orally. Administering pridopidine is effective in treating the patient. Administering pridopidine is also effective in reducing one or more of the symptoms of anxiety or of depression. Administering pridopidine is effective in facilitating rehabilitation of the patient.

Administering pridopidine is effective in facilitating rehabilitation of affective functions of the patient. Administering pridopidine is also effective in facilitating rehabilitation of behavioral function of the patient. Administering pridopidine is also effective in facilitating rehabilitation of emotional function of the patient. Administering pridopidine is also effective in facilitating rehabilitation of psychiatric function of the patient. Administering pridopidine is also effective in facilitating rehabilitation of sensory function of the patient.

Example 13: Assessment of Efficacy of Pridopidine for Treating Patients Afflicted with Schizophrenia Periodic (e.g., daily or twice daily) oral administration of pridopidine is effective in treating human patients afflicted with schizophrenia. Periodic (e.g., daily or twice daily) oral administration of pridopidine is effective to reduce anxiety and depression associated with schizophrenia in the subject. Periodic (e.g., daily or twice daily) oral administration of pridopidine is effective to reduce cognitive deficits associated with schizophrenia in the subject.

A pridopidine composition as described herein is administered orally to a subject suffering from schizophrenia. The administration of the composition is effective to treat the subject suffering from schizophrenia. The administration of the composition is also effective to reduce anxiety and depression associated with schizophrenia in the subject. The administration of the composition is also effective to reduce cognitive deficits associated with schizophrenia in the subject.

Example 14: Assessment of Efficacy of Pridopidine for Treating Patients Afflicted with Autism Periodic (e.g., daily or twice daily) oral administration of pridopidine is effective in treating human patients afflicted with autism. Periodic (e.g., daily or twice daily) oral administration of pridopidine is effective to reduce anxiety and depression associated with autism in the subject. Periodic (e.g., daily or twice daily) oral administration of pridopidine is effective to reduce cognitive deficits associated with autism in the subject.

A pridopidine composition as described herein is administered orally to a subject suffering from autism. The administration of the composition is effective to treat the subject suffering from autism. The administration of the composition is also effective to reduce anxiety and depression associated with autism in the subject. The administration of the composition is also effective to reduce cognitive deficits associated with autism in the subject.

Example 15: Assessment of Efficacy of Pridopidine for Treating Patients Afflicted with Epilepsy Periodic (e.g., daily or twice daily) oral administration of pridopidine is effective in treating human patients afflicted with epilepsy. Periodic (e.g., daily or twice daily) oral administration of pridopidine is effective to reduce anxiety and depression associated with epilepsy in the subject. Periodic (e.g., daily or twice daily) oral administration of pridopidine is effective to reduce cognitive deficits associated with epilepsy in the subject.

A pridopidine composition as described herein is administered orally to a subject suffering from epilepsy. The administration of the composition is effective to treat the subject suffering from epilepsy. The administration of the composition is also effective to reduce anxiety and depression associated with epilepsy in the subject. The administration of the composition is also effective to reduce cognitive deficits associated with epilepsy in the subject.

Example 16: Assessment of Efficacy of Pridopidine for Treating Patients Afflicted with Anxiety Disorders Periodic (e.g., daily or twice daily) oral administration of pridopidine is effective in treating human patients afflicted with anxiety disorders. Periodic (e.g., daily or twice daily) oral administration of pridopidine is effective to reduce cognitive deficits associated with anxiety disorders in the subject. A pridopidine composition as described herein is administered orally to a subject suffering from an anxiety disorder. The administration of the composition is effective to treat the subject suffering from an anxiety disorder. The administration of the composition is also effective to reduce cognitive deficits associated with an anxiety disorder in the subject.

Example 17: Assessment of Efficacy of Pridopidine for Treating Patients Afflicted with Major Depressive Disorder Periodic (e.g., daily or twice daily) oral administration of pridopidine is effective in treating human patients afflicted with major depressive disorder. Periodic (e.g., daily or twice daily) oral administration of pridopidine is effective to reduce cognitive deficits associated with major depressive disorder in the subject.

A pridopidine composition as described herein is administered orally to a subject suffering from major depressive disorder. The administration of the composition is effective to treat the subject suffering from major depressive disorder. The administration of the composition is also effective to reduce cognitive deficits associated with an anxiety disorder in the subject.

Example 18: Assessment of Efficacy of Pridopidine for Treating Patients Afflicted with Parkinson's Disease Periodic (e.g., daily or twice daily) oral administration of pridopidine is effective in treating human patients afflicted with Parkinson's disease. Periodic (e.g., daily or twice daily) oral administration of pridopidine is effective to reduce anxiety and depression associated with Parkinson's disease in the subject. Periodic (e.g., daily or twice daily) oral administration of pridopidine is effective to reduce cognitive deficits associated with Parkinson's disease in the subject.

A pridopidine composition as described herein is administered orally to a subject suffering from Parkinson's disease. The administration of the composition is effective to treat the subject suffering from Parkinson's disease. The administration of the composition is also effective to reduce anxiety and depression associated with Parkinson's disease in the subject. The administration of the composition is also effective to reduce cognitive deficits associated with Parkinson's disease in the subject.

Example 19: Assessment of Efficacy of Pridopidine for Treating Patients Afflicted with Alzheimer's Disease Periodic (e.g., daily or twice daily) oral administration of pridopidine is effective in treating human patients afflicted with Alzheimer's disease. Periodic (e.g., daily or twice daily) oral administration of pridopidine is effective to reduce anxiety and depression associated with Alzheimer's disease in the subject. Periodic (e.g., daily or twice daily) oral administration of pridopidine is effective to reduce cognitive deficits associated with Alzheimer's disease in the subject.

A pridopidine composition as described herein is administered orally to a subject suffering from Alzheimer's disease. The administration of the composition is effective to treat the subject suffering from Alzheimer's disease. The administration of the composition is also effective to reduce anxiety and depression associated with Alzheimer's disease in the subject. The administration of the composition is also effective to reduce cognitive deficits associated with Alzheimer's disease in the subject.

Example 20: Assessment of Efficacy of Pridopidine for Treating Patients Afflicted with Tardive Dyskinesia Periodic (e.g., daily or twice daily) oral administration of pridopidine is effective in treating human patients afflicted with tardive dyskinesia. Periodic (e.g., daily or twice daily) oral administration of pridopidine is effective to reduce anxiety and depression associated with tardive dyskinesia in the subject. Periodic (e.g., daily or twice daily) oral administration of pridopidine is effective to reduce cognitive deficits associated with tardive dyskinesia in the subject.

A pridopidine composition as described herein is administered orally to a subject suffering from tardive dyskinesia. The administration of the composition is effective to treat the subject suffering from tardive dyskinesia. The administration of the composition is also effective to reduce anxiety and depression associated with tardive dyskinesia in the subject. The administration of the composition is also effective to reduce cognitive deficits associated with tardive dyskinesia in the subject.

Example 21: Assessment of Efficacy of Pridopidine for Treating Patients Afflicted with Depression Periodic (e.g., daily or twice daily) oral administration of pridopidine is effective in treating human patients afflicted with Depression. Periodic (e.g., daily or twice daily) oral administration of pridopidine is effective to reduce cognitive deficits associated with Depression in the subject.

A pridopidine composition as described herein is administered orally to a subject suffering from Depression. The administration of the composition is effective to treat the subject suffering from Depression. The administration of the composition is also effective to reduce cognitive deficits associated with Depression in the subject.

Example 22: Assessment of Efficacy of Pridopidine for Treating Patients Afflicted with Sickle Cell Anemia Periodic (e.g., daily or twice daily) oral administration of pridopidine is effective in treating human patients afflicted with sickle cell anemia. Periodic (e.g., daily or twice daily) oral administration of pridopidine is effective to reduce anxiety and depression associated with sickle cell anemia in the subject. Periodic (e.g., daily or twice daily) oral administration of pridopidine is effective to reduce cognitive deficits associated with sickle cell anemia in the subject.

A pridopidine composition as described herein is administered orally to a subject suffering from sickle cell anemia. The administration of the composition is effective to treat the subject suffering from sickle cell anemia. The administration of the composition is also effective to reduce anxiety and depression associated with sickle cell anemia in the subject. The administration of the composition is also effective to reduce cognitive deficits associated with sickle cell anemia in the subject.

Example 23: Assessment of Efficacy of Pridopidine for Treating Patients Afflicted with Stroke Periodic (e.g., daily or twice daily) oral administration of pridopidine is effective in treating human patients after having a stroke. Periodic (e.g., daily or twice daily) oral administration of pridopidine is effective to reduce anxiety and depression associated with stroke in the subject. Periodic (e.g., daily or twice daily) oral administration of pridopidine is effective to reduce cognitive deficits associated with stroke in the subject.

A pridopidine composition as described herein is administered orally to a subject after suffering from a stroke. The administration of the composition is effective to treat the subject after suffering from a stroke. The administration of the composition is also effective to reduce anxiety and depression associated with stroke in the subject. The administration of the composition is also effective to reduce cognitive deficits associated with stroke in the subject.

Example 24: Assessment of Efficacy of Pridopidine for Treating Patients Afflicted with Chronic Pain Syndrome Periodic (e.g., daily or twice daily) oral administration of pridopidine is effective in treating human patients afflicted with chronic pain syndrome. Periodic (e.g., daily or twice daily) oral administration of pridopidine is effective to reduce anxiety and depression associated with chronic pain syndrome in the subject. Periodic (e.g., daily or twice daily) oral administration of pridopidine is effective to reduce cognitive deficits associated with chronic pain syndrome in the subject.

A pridopidine composition as described herein is administered orally to a subject suffering from chronic pain syndrome. The administration of the composition is effective to treat the subject suffering from chronic pain syndrome. The administration of the composition is also effective to reduce anxiety and depression associated with chronic pain syndrome in the subject. The administration of the composition is also effective to reduce cognitive deficits associated with chronic pain syndrome in the subject.

Example 25: Assessment of Efficacy of Pridopidine for Treating Patients Afflicted with Addiction Periodic (e.g., daily or twice daily) oral administration of pridopidine is effective in treating human patients afflicted with addiction. Periodic (e.g., daily or twice daily) oral administration of pridopidine is effective to reduce anxiety and depression associated with addiction in the subject. Periodic (e.g., daily or twice daily) oral administration of pridopidine is effective to reduce cognitive deficits associated with addiction in the subject.

A pridopidine composition as described herein is administered orally to a subject suffering from addiction. The administration of the composition is effective to treat the subject suffering from addiction. The administration of the composition is also effective to reduce anxiety and depression associated with addiction in the subject. The administration of the composition is also effective to reduce cognitive deficits associated with addiction in the subject.

Example 26: Assessment of Efficacy of Pridopidine for Treating Patients Afflicted with Huntington's Disease Periodic (e.g., daily or twice daily) oral administration of pridopidine is effective in treating human patients afflicted with Huntington's disease. Periodic (e.g., daily or twice daily) oral administration of pridopidine is effective to reduce anxiety and depression associated with Huntington's disease in the subject. Periodic (e.g., daily or twice daily) oral administration of pridopidine is effective to reduce cognitive deficits associated with Huntington's disease in the subject.

A pridopidine composition as described herein is administered orally to a subject suffering from Huntington's disease. The administration of the composition is effective to treat the subject suffering from Huntington's disease. The administration of the composition is also effective to reduce anxiety and depression associated with Huntington's disease in the subject. The administration of the composition is also effective to reduce cognitive deficits associated with Huntington's disease in the subject.

REFERENCES

Agosta, F., Pievani, M., Geroldi, C., Copetti, M., Frisoni, G. B., & Filippi, M. (2012). Resting state fMRI in Alzheimer's disease: Beyond the default mode network. Neurobiology of Aging, 33(8), 1564-1578.

Ammar, I. H., Muzaimi, M., & Sharif, M. M. The effects on motor behaviour and short-term memory tasks in mice following an acute administration of Mitragyna *speciosa* alkaloid extract and mitragynine. Journal of Medicinal Plants Research Vol. 5(24), pp. 5810-5817, 30 October, 2011.

Ates-Alagoz, Z., & Adejare, A. NMDA Receptor Antagonists for Treatment of Depression. Pharmaceuticals 2013, 6, 480-499.

Austin Marie-Paule, Cognitive deficits in depression Possible implications for functional neuropathology. The British Journal of Psychiatry (2001) 178: 200-206.

Balthazar, M., Weiler, M., Campos, B., Rezende, T. J., Damasceno, B., & Cendes, F. (2014). Alzheimer'S As a Default Mode Network Disease: a Grey Matter, Functional, and Structural Connectivity Study. Alzheimer's & Dementia, 10(4), P391.

Bartoszyk, G. D. (1998). Anxiolytic effects of dopamine receptor ligands: I. Involvement of dopamine autoreceptors. Life Sciences, 62(7), 649-663.

Bartoszyk, G. D. et al. (1997). EMD 68843, a serotonin reuptake inhibitor with selective presynaptic 5-HT1A receptor agonistic properties. European Journal of Pharmacology, 322(2-3), 147-153.

Bech P, Rasmussen N A, Olsen L R, Noerholm V, Abildgaard W. The sensitivity and specificity of the Major Depression Inventory, using the Present State Examination as the index of diagnostic validity. J Affect Disord. 2001 October; 66(2-3):159-64. doi: 10.1016/s0165-0327(00)00309-8. PMID: 11578668.

Bech P. Rating scales in depression: limitations and pitfalls. Dialogues Clin Neurosci. 2006; 8(2):207-15. doi: 10.31887/DCNS 0.2006.8.2/pbech. PMID: 16889106; PMCID: PMC3181766.

Bonnelle, V., Ham, T. E., Leech, R., Kinnunen, K. M., Mehta, M. A., Greenwood, R. J., & Sharp, D. J. (2012). Salience network integrity predicts default mode network function after traumatic brain injury. Proceedings of the National Academy of Sciences of the United States of America, 109(12), 4690-4695.

Bourne J N, Harris K M. Balancing structure and function at hippocampal dendritic spines. Annu Rev Neurosci. 2008; 31:47-67. doi: 10.1146/annurev.neuro.31.060407.125646. PMID: 18284372; PMCID: PMC2561948.

Brier, M. R., Thomas, J. B., & Ances, B. M. (2014). Network dysfunction in Alzheimer's disease: refining the disconnection hypothesis. Brain Connectivity, 4(5), 299-311. https://doi.org/10.1089/brain.2014.0236

Broekkamp C L, Rijk H W, Joly-Gelouin D, Lloyd K L. Major tranquillizers can be distinguished from minor tranquillizers on the basis of effects on marble burying and swim-induced grooming in mice. Eur J Pharmacol. 1986 Jul. 31; 126(3):223-9. doi.: 10.1016/0014-2999(86) 90051-8. PMID: 2875886.

Bryan Kathryn J., Hyoung-gon Lee, George Perry, Mark A. Smith, and Gemma Casadesus. Chapter 1 Transgenic Mouse Models of Alzheimer's Disease: Behavioral Testing and Considerations. Methods of Behavior Analysis in Neuroscience. $2^{nd}$ edition. (2009).

Buckner, R. L., Andrews-Hanna, J. R., & Schacter, D. L. (2008). The brain's default network: Anatomy, function, and relevance to disease. Annals of the New York Academy of Sciences, 1124, 1-38. https://doi.org/10.1196/annals.1440.011

Callizot N, Combes M, Steinschneider R, Poindron P. Operational dissection of β-amyloid cytopathic effects on cultured neurons. J Neurosci Res. (2013); May; 91(5): 706-16.

Combs C K, Johnson D E, Karlo J C, Cannady S B, Landreth G E Inflammatory mechanisms in Alzheimer's disease: inhibition of beta-amyloid-stimulated pro-inflammatory responses and neurotoxicity by PPARgamma agonists. J Neurosci. (2000); 20(2):558-67.

Connor K M, Davidson J R, Churchill L E, Sherwood A, Foa E, Weisler R H. Psychometric properties of the Social Phobia Inventory (SPIN). New self-rating scale. Br J Psychiatry. 2000 April; 176:379-86. doi: 10.1192/bjp.176.4.379. PMID: 10827888.

Cumming T B, et al. Stroke, cognitive deficits, and rehabilitation: still an incomplete picture. Int J Stroke. 2013 January; 8(1):38-45.

Cummings J L, Vinters H V, Cole G M, Khachaturian Z S. Alzheimer's disease: etiologies, pathophysiology, cognitive reserve, and treatment opportunities. Neurology. (1998); 51(1 Suppl 1):S2-17; discussion S65-7.

David M Dietz et al., ΔFosB Induction in Prefrontal Cortex by Antipsychotic Drugs is Associated with Negative Behavioral Outcomes. Neuropsychopharmacology (2014) 39, 538-544.

Detrait E et al. Automation of continuous spontaneous alternation to increase the throughput for in vivo screening of cognitive enhancers. Optimization of the ethovision system for the Y-maze test in mice. Proceedings of Measuring Behavior 2010 (Eindhoven, The Netherlands, August 24-27, 2010).

Dubois B and Pillon B, Cognitive deficits in Parkinson's disease. J Neurol. 1997 January; 244(1):2-8.

Ferreri F et al. Current research on cognitive aspects of anxiety disorders. Current Opinion in Psychiatry 2011, 24:49-54

Fioravanti M. Cognitive deficits in schizophrenia: an updated metanalysis of the scientific evidence. Fioravanti et al. BMC Psychiatry 2012, 12:64

Foroud T et al. Cognitive scores in carriers of Huntington's disease gene compared to noncarriers. Ann Neurol. 1995 May; 37(5):657-64.

Francardo V, Bez F, Wieloch T, Nissbrandt H, Ruscher K, Cenci M A. Pharmacological stimulation of sigma-1 receptors has neurorestorative effects in experimental parkinsonism. Brain. 2014 July; 137(Pt 7):1998-2014. doi: 10.1093/brain/awu107. Epub 2014 Apr. 22. PMID: 24755275.

Geva M, Kusko R, Soares H, Fowler K D, Birnberg T, Barash S, Wagner A M, Fine T, Lysaght A, Weiner B, Cha Y, Kolitz S, Towfic F, Orbach A, Laufer R, Zeskind B, Grossman I, Hayden M R. Pridopidine activates neuroprotective pathways impaired in Huntington Disease. Hum Mol Genet. 2016 Sep. 15; 25(18):3975-3987. doi: 10.1093/hmg/ddw238. Epub 2016 Jul. 27. PMID: 27466197; PMCID: PMC5291233.

Ghosh, B. C. P., Calder, A. J., Peers, P. V., Lawrence, A. D., Acosta-Cabronero, J., Pereira, J. M., Rowe, J. B. (2012). Social cognitive deficits and their neural correlates in progressive supranuclear palsy. Brain, 135(7), 2089-2102. https://doi.org/10.1093/brain/aws128

Girardi, A., MacPherson, S. E., & Abrahams, S. (2011). Deficits in Emotional and Social Cognition in Amyotrophic Lateral Sclerosis. Neuropsychology, 25(1), 53-65.

Gould, T. J. (2010). Addiction and cognition. Addiction Science & Clinical Practice, 5(2), 4. Graveland, G A, et al. Evidence for degenerative and regenerative changes in neostriatal spiny neurons in Huntington's disease. Science. 1985 Feb. 15; 227(4688):770-3.

Guye, M., Bettus, G., Bartolomei, F., & Cozzone, P. J. (2010). Graph theoretical analysis of structural and functional connectivity MRI in normal and pathological brain networks. Magnetic Resonance Materials in Physics, Biology and Medicine, 23(5-6), 409-421. https://doi.org/10.1007/s10334-010-0205-z Hamilton M. The assessment of anxiety states by rating. Br J Med Psychol. 1959; 32(1):50-5. doi: 10.1111/j.2044-8341.1959.tb00467.x. PMID: 13638508.

Hart R et al., Cognitive Impairment in Patients With Chronic Pain: The Significance of Stress. Current Pain and Headache Reports 2003, 7:116-226.

Hironaka N, Tanaka K, Izaki Y, Hori K, Nomura M. Memory-related acetylcholine efflux from rat prefrontal cortex and hippocampus: a microdialysis study. Brain Res. 2001 May 18; 901(1-2):143-50. https://doi.org/10.1016/j.jalz.2014.05.476

Jonkers N, Sane S, Ebinger G, Michotte Y.; MK801 influences L-DOPA-induced dopamine release in intact and hemi-parkinson rats. Eur J Pharmacol. 2000 Nov. 3; 407(3):281-91. Julian L J. Measures of anxiety: State-Trait Anxiety Inventory (STAI), Beck Anxiety Inventory (BAI), and Hospital Anxiety and Depression Scale-Anxiety (HADS-A). Arthritis Care Res (Hoboken). 2011 November; 63 Suppl 11(0 11):5467-72. doi: 10.1002/acr.20561. PMID: 22588767; PMCID: PMC3879951.

Kawahara M, Kuroda Y. Molecular mechanism of neurodegeneration induced by Alzheimer's beta-amyloid protein: channel formation and disruption of calcium homeostasis. Brain Res Bull. (2000); 53(4):389-97.

Keefe R S et al., Cognitive effects of pharmacotherapy for major depressive disorder: a systematic review. J Clin Psychiatry. 2014 August; 75(8):864-76.

Kipps, C. M., & Hodges, J. R. (2006). Theory of mind in frontotemporal dementia. Social Neuroscience, 1(3-4), 235-244. https://doi.org/10.1080/17470910600989847

Krabbendam L et al., Tardive dyskinesia is associated with impaired retrieval from long-term memory: the Curacao Extrapyramidal Syndromes Study: IV. Schizophr Res. 2000 Mar. 16; 42(1):41-6.

Kreitzer A C, Malenka R C. Striatal plasticity and basal ganglia circuit function. Neuron. 2008 Nov. 26; 60(4): 543-54. doi: 10.1016/j.neuron.2008.11.005. PMID: 19038213; PMCID: PMC2724179.

Leary M R. Social anxiousness: the construct and its measurement. J Pers Assess. 1983 February; 47(1):66-75. doi: 10.1207/s15327752jpa4701 8. PMID: 6834234.

Lucas-Jimenez, O., Ojeda, N., Peña, J., Díez-Cirarda, M., Cabrera-Zubizarreta, A., Gomez-Esteban, J. C., . . . Ibarretxe-Bilbao, N. (2016). Altered functional connectivity in the default mode network is associated with cognitive impairment and brain anatomical changes in Parkinson's disease. Parkinsonism and Related Disorders, 33, 58-64. https://doi.org/10.1016/j.parkreldis. 2016.09.012

Luszczki J, Wojcik-Cwikla J, Andres M J, Czuczwar S (2005). Pharmacological and Behavioral Characteristics of Interactions between Vigabatrin and Conventional Antiepileptic Drugs in Pentylenetetrazole-Induced Seizures in Mice: An Isobolographic Analysis. Neuropsychopharmacology, 30: 958-973.

Maurice T. & Privat, A. SA4503, a novel cognitive enhancer with sigma 1 receptor agonist properties, facilitates NMDA receptor-dependent learning in mice. Eur J Pharmacol 1997; 328(1):9-18.

McKhann G, Drachman D, Folstein M, Katzman R, Price D, Stadlan E M. Clinical diagnosis of Alzheimer's disease: report of the NINCDS-ADRDA Work Group under the auspices of Department of Health and Human Services Task Force on Alzheimer's Disease. Neurology (1984); 34 (7): 939-44

McKhann G M., Knopman D S., Chertkow H., Hyman B T., Jack C R. Jr., Kawas C H, Klunk W E, Koroshetz W J, Manly J, Mayeux R, Mohs R C, Morris J C, Rossor M N, Scheltens P, Carrillo M C., Thies B., Weintraub S., Phelps C H. The diagnosis of dementia due to Alzheimer's disease: Recommendations from the National Institute on Aging-Alzheimer's Association workgroups on diagnostic guidelines for Alzheimer's disease. Alzheimer's & Dementia (2011); 7(3):263-269 Alzheimer's Association, www.alz.org Mevel, K., Chételat, G., Eustache, F., & Desgranges, B. (2011). The default mode network in healthy aging and Alzheimer's disease. International Journal of Alzheimer's Disease, 2011. https://doi.org/10.4061/2011/535816

Mohan A, Roberto A J, Mohan A, Lorenzo A, Jones K, Carney M J, Liogier-Weyback L, Hwang S, Lapidus K A. The Significance of the Default Mode Network (DMN) in Neurological and Neuropsychiatric Disorders: A Review. Yale J Biol Med. 2016 Mar. 24; 89(1):49-57. PMID: 27505016; PMCID: PMC4797836.

Nilsson M, Carlsson A, Markinhuhta K R, Sonesson C, Pettersson F, Gullme M, et al. The dopaminergic 56 tabilizer ACR16 counteracts the behavioural primitivization induced by the NMDA receptor antagonist MK-801 in mice: implications for cognition. Prog Neuropsychopharmacol Biol Psychiatry 2004; 28:677-85.

Onaolapo O et al. Elevated Plus Maze and Y-Maze Behavioral Effects of Subchronic, Oral Low Dose Monosodium Glutamate in Swiss Albino Mice IOSR Journal of Pharmacy and Biological Sciences, Volume 3, Issue 4 (September-October 2012), PP 21-27.

Parada-Turska J, Turski W A. Excitatory amino acid antagonists and memory: effect of drugs acting at N-methyl-D-aspartate receptors in learning and memory tasks. Neuropharmacology 1990; 29(12): 1111-6.

Parent Manse B. et al. Septohippocampal Acetylcholine: Involved in but not Necessary for Learning and Memory? Learn. Mem. 2004. 11: 9-20

Petrella, J. R., Sheldon, F. C., Prince, S. E., Calhoun, V. D., & Doraiswamy, P. M. (2011). Default mode network connectivity in stable vs progressive mild cognitive impairment. Neurology, 76(6), 511-517. https://doi.org/10.1212/WNL.0b013e31820af94e Pike C J, Walencewicz A J, Glabe C G, Cotman C W. In vitro aging of beta-amyloid protein causes peptide aggregation and neurotoxicity. Brain Res. (1991); 563(1-2):311-4.

Rapaport Mark, Future Drugs for the Treatment of Depression: The Need to Look Beyond Monoamine Systems. Primary Psychiatry. 2009; 16:3(Suppl 3):14-16.

Remington's Pharmaceutical Sciences, 17th ed. (1985). Journal of Pharmaceutical Sciences, 74(10), 1143-1144. doi:10.1002/jps.2600741047

Sakono M1, Zako T. Amyloid oligomers: formation and toxicity of Abeta oligomers. FEBS J. (2010) March; 277(6):1348-58.

Sambataro, F., Murty, V. P., Callicott, J. H., Tan, H. Y., Das, S., Weinberger, D. R., & Mattay, V. S. (2010). Age-related alterations in default mode network: Impact on working memory performance. Neurobiology of Aging, 31(5), 839-852.

Saunders J A, Gandal M J, Roberts T P, Siegel S J. NMDA antagonist MK801 recreates auditory electrophysiology disruption present in autism and other neurodevelopmental disorders. Behavioural brain research 2012; 234(2): 233-237.

Selkoe D J. Alzheimer's disease: genes, proteins, and therapy. Physiol Rev (2001); 81: 741-766.

Seo, J. S., Chung, Y. C., Park, K. Y., Eun, H. B., & Kim, Y. H. Effect of MK-801 on the Prevention and Treatment of Tardive Dyskinesia. Korean Journal of Biological Psychiatry. Volume 4, Number 2 (February 1997).

Sisodia S S, Koo E H, Beyreuther K, Unterbeck A, Price D L. Evidence that beta-amyloid protein in Alzheimer's disease is not derived by normal processing. Science. (1990); 248(4954):492-5.

Stafstrom C E, Tandon P, Hori A, Liu Z, Mikati M A, Holmes G L., Acute effects of MK801 on kainic acid-induced seizures in neonatal rats. Epilepsy Res. 1997 January; 26(2):335-44.

Steen R G et al., Cognitive deficits in children with sickle cell disease. J Child Neurol. 2005 February; 20(2):102-7.

Steimer T. Animal models of anxiety disorders in rats and mice: some conceptual issues. Dialogues Clin Neurosci. 2011; 13(4):495-506. doi: 10.31887/DCNS.2011.13.4/tsteimer. PMID: 22275854; PMCID: PMC3263396.

Strik J J, Honig A, Lousberg R, Denollet J. Sensitivity and specificity of observer and self-report questionnaires in major and minor depression following myocardial infarction. Psychosomatics. 2001 September-October; 42(5): 423-8. doi: 10.1176/appi.psy.42.5.423. PMID: 11739910.

Treit D, Pinel J P, Fibiger H C. Conditioned defensive burying: a new paradigm for the study of anxiolytic agents, Pharmacol Biochem Behav. 1981 October; 15(4): 619-26. doi: 10.1016/0091-3057(81)90219-7. PMID: 6117086.

Treit D. Animal models for the study of anti-anxiety agents: a review. Neurosci Biobehav Rev. 1985 Summer; 9(2) 03-22. doi: 10.1016/0149-7634(85)90046-6. PMID: 2861589.

Van den Buuse M, Garner B, Gogos A, and Kusljic S. Importance of animal models in schizophrenia research. Aust N Z J Psychiatry 2005 July; 39(7):550-7.

Van Rijckevorsel K, Cognitive problems related to epilepsy syndromes, especially malignant epilepsies. (2006) Seizure, 15 (4), pp. 227-234.

Winkler J, et al., Essential role of neocortical acetylcholine in spatial memory. Nature 375, 484-487 (8 Jun. 1995).

Zhou, J., Greicius, M. D., Gennatas, E. D., Growdon, M. E., Jang, J. Y., Rabinovici, G. D., . . . Seeley, W. W. (2010). Divergent network connectivity changes in behavioural variant frontotemporal dementia and Alzheimer's disease. Brain, 133(5), 1352-1367. https://doi.org/10.1093/brain/awq075

What is claimed is:

1. A method of treating depression or anxiety in a human subject by administering a composition comprising an amount of pridopidine, or a pharmaceutically acceptable salt thereof.

2. The method of claim 1, wherein the depression or anxiety is not caused by Huntington's Disease.

3. The method of claim 1, wherein the depression or anxiety is associated with cognitive deficits.

4. The method of claim 2, wherein the depression or anxiety is associated with cognitive deficits.

5. The method of claim 3, wherein the cognitive deficits comprise memory loss, loss of higher reasoning, forgetfulness, learning disabilities, concentration difficulties, or decreased intelligence.

6. The method of claim 4, wherein the cognitive deficits comprise memory loss, loss of higher reasoning, forgetfulness, learning disabilities, concentration difficulties, or decreased intelligence.

7. The method of claim 1, wherein the composition comprises between 22.5 mg/day and 315 mg/day of pridopidine or pharmaceutically acceptable salt thereof.

8. The method of claim 1, wherein the composition is administered once daily or twice daily.

9. The method of claim 1, wherein the composition is administered orally.

10. The method of claim 1, wherein the pharmaceutically acceptable salt of pridopidine comprises pridopidine hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, salicylate, sorbate, stearate, succinate, tartrate or toluene-p-sulphonate salt.

11. The method of claim 10, wherein the salt comprises hydrochloride salt.

12. The method of claim 1, wherein the composition comprises an amount of pridopidine base.

* * * * *